(12) United States Patent
Fischer et al.

(10) Patent No.: US 6,251,830 B1
(45) Date of Patent: Jun. 26, 2001

(54) DIALKYL-HALOGENOPHENYL-SUBSTITUTED KETOENOLS

(75) Inventors: Reiner Fischer, Monheim; Thomas Bretschneider, Lohmar; Hermann Hagemann; Folker Lieb, both of Leverkusen; Michael Ruther, Monheim; Arno Widdig, Odenthal; Peter Dahmen, Neuss; Markus Dollinger, Leverkusen; Christoph Erdelen, Leichlingen; Hans-Joachim Santel, Leverkusen; Ulrike Wachendorff-Neumann, Neuwied; Alan Graff, Köln; Wolfram Andersch, Bergisch Gladbach, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/360,510

(22) Filed: Jul. 26, 1999

Related U.S. Application Data

(62) Division of application No. 08/981,610, filed as application No. PCT/EP96/02601 on Jun. 17, 1996, now Pat. No. 5,994,274.

(30) Foreign Application Priority Data

Jun. 30, 1995 (DE) ............................................. 195 23 850
Jan. 31, 1996 (DE) ............................................. 196 03 332

(51) Int. Cl.[7] ..................... A01N 43/08; A01N 43/10; A01N 43/16; C07D 207/38; C07D 307/60
(52) U.S. Cl. ..................... 504/251; 504/266; 504/288; 504/292; 504/299; 514/346; 514/365; 514/444; 514/445; 514/456; 514/460; 514/473; 546/282.1; 548/203; 549/60; 549/62; 549/265; 549/285; 549/292; 549/313; 549/319; 549/417
(58) Field of Search ........................ 546/282.1; 548/203; 549/60, 62, 265, 285, 292, 313, 319, 417; 504/251, 266, 289, 292, 299; 514/346, 365, 444, 445, 456, 460, 473

(56) References Cited

U.S. PATENT DOCUMENTS 5,142,065   8/1992   Fischer et al. ..................... 548/533

(List continued on next page.)

FOREIGN PATENT DOCUMENTS 0 456 063   11/1991   (EP) .

(List continued on next page.)

*Primary Examiner*—Richard L. Raymond
(74) *Attorney, Agent, or Firm*—Norris McLaughlin & Marcus

(57) ABSTRACT

The present invention relates to new compounds of the formula (I)

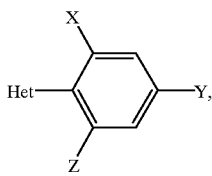

in which
X represents alkyl,
Y represents halogen or alkyl and
Z represents halogen or alkyl,
with the proviso that one of the radicals Y and Z always represents halogen and the other alkyl,
Het represents one of the groups

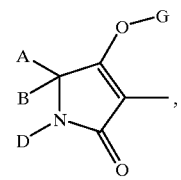

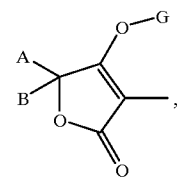

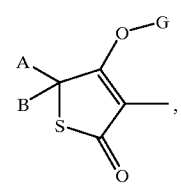

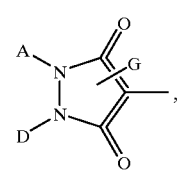

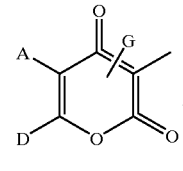

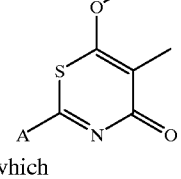

in which
A, B, D and G have the meanings given in the description, a plurality of processes for their preparation and their use as pesticides and herbicides.

9 Claims, No Drawings

U.S. PATENT DOCUMENTS

| | | | |
|---|---|---|---|
| 5,258,527 | 11/1993 | Krauskoph et al. | 548/543 |
| 5,262,383 | 11/1993 | Fischer et al. | 504/195 |
| 5,393,729 | 2/1995 | Fischer et al. | 504/128 |
| 5,462,913 | 10/1995 | Fischer et al. | 504/138 |
| 5,508,436 | 4/1996 | Fischer et al. | 548/544 |
| 5,565,450 | 10/1996 | Fischer et al. | 514/227.2 |
| 5,567,671 | 10/1996 | Fischer et al. | 504/283 |
| 5,683,965 * | 11/1997 | Bachmann et al. | 504/238 |
| 5,981,567 * | 11/1999 | Fischer et al. | 514/409 |

FOREIGN PATENT DOCUMENTS

| | | |
|---|---|---|
| 0 528 156 | 2/1993 | (EP) . |
| 0 588 137 | 3/1994 | (EP) . |
| 0 595 130 | 5/1994 | (EP) . |
| 0 596 298 | 5/1994 | (EP) . |
| WO 95/01971 | 1/1995 | (WO) . |

* cited by examiner

DIALKYL-HALOGENOPHENYL-SUBSTITUTED KETOENOLS

This application is a division of application Ser. No. 08/981,610, filed on Dec. 23, 1997, now U.S. Pat. No. 5,994,274, which is a 371 of PCT/EP96/02601, filed on Jun. 17, 1996.

The invention relates to new phenyl-substituted cyclic ketoenols, a plurality of processes and intermediates for their preparation and their use as pesticides and herbicides.

It has already been disclosed that certain phenyl-substituted cyclic ketoenols are effective as insecticides, acaricides and/or herbicides.

Pharmaceutical properties of 3-acyl-pyrrolidine-2,4-diones have previously been described (S. Suzuki et al. Chem. Pharm. Bull. 15 1120 (1967)). Furthermore, N-phenylpyrrolidine-2,4-diones have been synthesized by R. Schmierer and H. Mildenberger (Liebigs Ann. Chem. 1985, 1095). A biological activity of these compounds has not been described.

EP-A-0262399 and GB-A-2266888 disclose compounds (3-aryl-pyrrolidine-2,4-diones) of similar structure, of which, however, no herbicidal, insecticidal or acaricidal action has been disclosed. Unsubstituted, bicyclic 3-aryl-pyrrolidine-2,4-dione derivatives (EP-A-355599 and EP-A-415211) and substituted monocyclic 3-aryl-pyrrolidine-2,4-dione derivatives (EP-A-377893 and EP-A-442077) with herbicidal, insecticidal or acaricidal action are known.

Polycyclic 3-arylpyrrolidine-2,4-dione derivatives (EP-A-442073) and 1H-arylpyrrolidine-dione derivatives (EP-A-456063, EP-A-521334, EP-A-596298, EP-A-613884, DE 4440594, EP-A-613885, WO 94/01997 and WO 95/01358) are furthermore known.

It is known that certain substituted $\Delta^3$-dihydrofuran-2-one derivatives have herbicidal properties (cf. DE-A-4014420). The synthesis of the tetronic acid derivatives used as starting compounds (e.g. 3-(2-methyl-phenyl)-4-hydroxy-5-(4-fluorophenyl)-$\Delta^3$-dihydrofuran-2-one) is likewise described in DE-A-4014420. Compounds of similar structure without details of an insecticidal and/or acaricidal activity are known from the publication Campbell et al., J. Chem. Soc., Perkin Trans. 1, 1985, (8) 1567–76. Furthermore, 3-aryl-$\Delta^3$-dihydrofuranone derivatives having herbicidal, acaricidal and insecticidal properties are disclosed in EP-A-528156, but the action described there is not always adequate. 3-Aryl-4-hydroxy-$\Delta^3$-dihydrofuranone derivatives are disclosed in EP-A-647637. Thiotetronic acids are disclosed in WO 95/26345.

The literature further discloses certain 3H-pyrazol-3-one derivatives, for example 1,2-diethyl-1,2-dihydro-5-hydroxy-4-phenyl-3H-pyrazol-3-one or {[5-oxo-1,2-diphenyl-4-(p-sulphophenyl)-3-pyrazolin-3-yl]-oxy} [lacuna] disodium salt or p-(3-hydroxy-5-oxo-1,2-diphenyl-3-pyrazolin-4-yl)-benzenesulphonic acid (cf J. Heterocycl. Chem., 25(5), 1301–1305, 1988 or J. Heterocycl. Chem., 25(5), 1307–1310, 1988 or Zh. Obshch. Khim., 34(7), 2397–2402, 1964). A biological action of these compounds, however, is not described.

It is furthermore known that the trisodium salt of 4,4',4"-(5-hydroxy-3-oxo-1H-pyrazole-1,2,4(3H)-triyl)-tris-benzenesulphonic acid has pharmacological properties (cf. Farmakol. Toksikol. (Moscow), 38(2), 180–186, 1976). Its use in plant protection, however, is not known.

In addition, EP-A-508126 and WO 92/16510 describe 4-arylpyrazolidine-3,5-dione derivatives having herbicidal, acaricidal and insecticidal properties.

Certain phenyl-pyrone derivatives unsubstituted in the phenyl ring have already been disclosed (cf. A. M. Chirazi, T. Kappe and E. Ziegler, Arch. Pharm. 309, 558 (1976) and K.-H. Boltze and K. Heidenbluth, Chem. Ber. 91, 2849), a possible utility for these compounds as pesticides not being indicated. Phenyl-pyrone derivatives substituted in the phenyl ring and having herbicidal, acaricidal and insecticidal properties are described in EP-A-588137.

Certain 5-phenyl-1,3-thiazine derivatives unsubstituted in the phenyl ring have already been described (cf. E. Ziegler and E. Steiner, Monatsh. 95, 147 (1964), R. Ketcham, T. Kappe and E. Ziegler, J. Heterocycl. Chem. 10, 223 (1973)), a possible application as pesticides not being indicated for these compounds. 5-Phenyl-1,3-thiazine derivatives substituted in the phenyl ring and having herbicidal, acaricidal and insecticidal action are described in WO 94/14785.

The activity and spectrum of action of these compounds, however, is not always completely satisfactory, in particular at low application rates and concentrations.

New compounds of the formula (I)

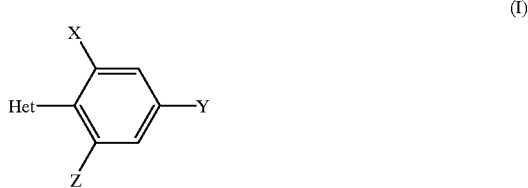

have now been found, in which

X represents alkyl,

Y represents halogen or alkyl and

Z represents halogen or alkyl, with the proviso that one of the radicals Y and Z always represents halogen and the other alkyl, Het represents one of the groups

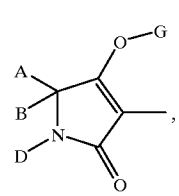

(1)

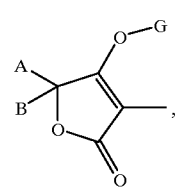

(2)

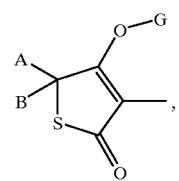

(3)

-continued

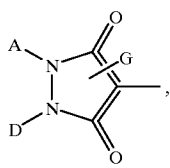
(4)

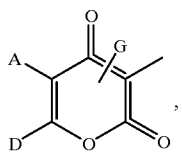
(5)

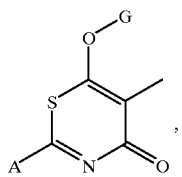
(6)

in which

- A represents hydrogen or alkyl, alkenyl, alkoxyalkyl, polyalkoxyalkyl or alkylthioalkyl, each of which is optionally substituted by halogen or cycloalkyl or heterocyclyl, each of which is saturated or unsaturated and optionally substituted, or aryl, arylalkyl or hetaryl, each of which is optionally substituted by halogen, alkyl, halogenoalkyl, alkoxy, halogenoalkoxy, cyano or nitro,
- B represents hydrogen, alkyl or alkoxyalkyl, or
- A and B, together with the carbon atom to which they are bonded, represent a saturated or unsaturated, optionally substituted carbocycle or heterocycle,
- D represents hydrogen or an optionally substituted radical of the series alkyl, alkenyl, alkinyl, alkoxyalkyl, polyalkoxyalkyl, alkylthioalkyl, saturated or unsaturated cycloalkyl, saturated or unsaturated heterocyclyl, arylalkyl, aryl, hetarylalkyl or hetaryl, or
- A and D, together with the atoms to which they are bonded, represent a saturated or unsaturated and optionally substituted carbocycle or heterocycle,
- G, in the case in which Het represents one of the radicals (1), (2), (3), (5) or (6), represents hydrogen (a) or, in the case in which Het represents one of the radicals (1), (2), (3), (4), (5) or (6), represents one of the groups

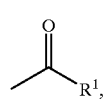
(b)

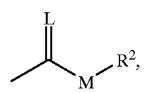
(c)

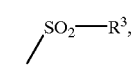
(d)

(e)

E or
(f)

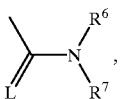
(g)

in which

- E represents a metal ion equivalent or an ammonium ion,
- L represents oxygen or sulphur,
- M represents oxygen or sulphur,
- $R^1$ represents alkyl, alkenyl, alkoxyalkyl, alkylthioalkyl or polyalkoxyalkyl, each of which is optionally substituted by halogen, or cycloalkyl or heterocyclyl, each of which is optionally substituted by halogen, alkyl or alkoxy, or phenyl, phenylalkyl, hetaryl, phenoxyalkyl or hetaryloxyalkyl, each of which is optionally substituted,
- $R^2$ represents alkyl, alkenyl, alkoxyalkyl or polyalkoxyalkyl, each of which is optionally substituted by halogen, or cycloalkyl, phenyl or benzyl, each of which is optionally substituted,
- $R^3$, $R^4$ and $R^5$ independently of one another represent alkyl, alkoxy, alkylamino, dialkylamino, alkylthio, alkenylthio or cycloalkylthio, each of which is optionally substituted by halogen, or phenyl, phenoxy or phenylthio, each of which is optionally substituted,
- $R^6$ and $R^7$ independently of one another represent hydrogen, or alkyl, cycloalkyl, alkenyl, alkoxy, alkoxyalkyl, each of which is optionally substituted by halogen, or phenyl or benzyl, each of which is optionally substituted, or, together with the N atom to which they are bonded, form an optionally substituted cyclic system optionally containing oxygen or sulphur.

The compounds of the formula (I) can also be present, depending on the nature of the substituents, as geometric and/or optical isomers or isomer mixtures of differing composition which, if appropriate, can be separated in a customary manner. Both the pure isomers and the isomer mixtures, their preparation and use, and compositions containing these are a subject of the present invention. In the following, for the sake of simplicity, however, compounds of the formula (I) are always referred to, although both the pure compounds and, if appropriate, mixtures of different proportions of isomeric compounds are intended.

Including the meanings (1) to (6) of the group Het, the following principle structures (I-1) to (I-6) result:

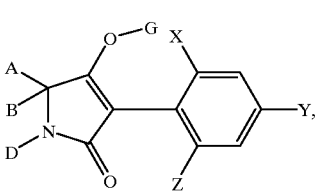
(I-1)

(I-2)
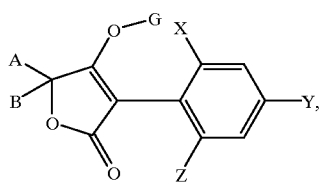
(I-3)
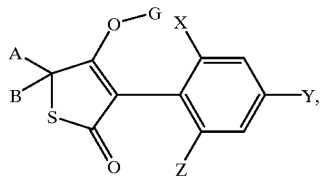
(I-4)
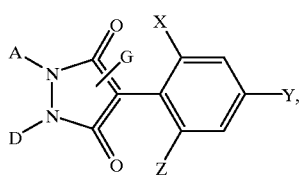
(I-5)
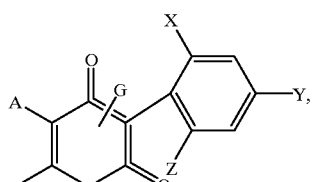
(I-6)
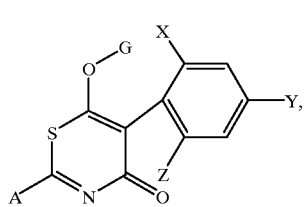
in which
A, B, D, G, X, Y and Z have the meanings given above.
Including the various meanings (a), (b), (c), (d), (e), (f) and (g) of the group G, the following principle structures (I-1-a) to (I-1-g) result if Het represents the group (1)
(I-1-c):
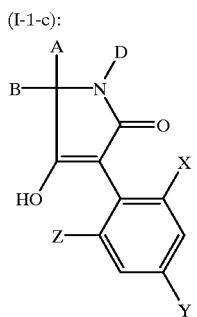
(I-1-b):
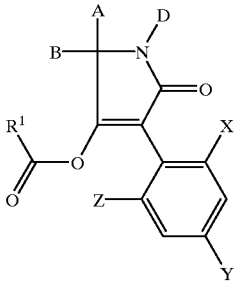
(I-1-c):
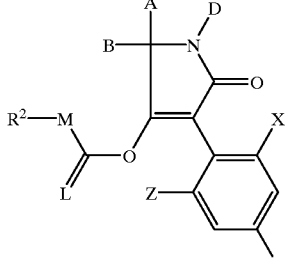
(I-1-d):
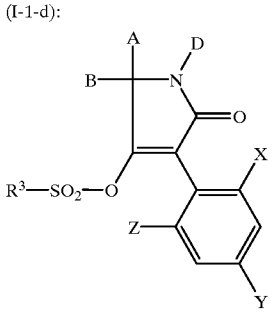
(I-1-e):
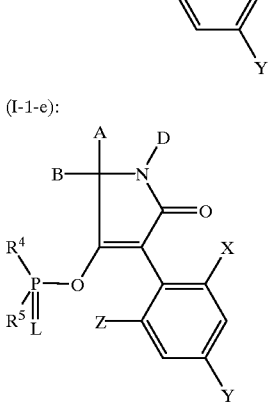
(I-1-f):
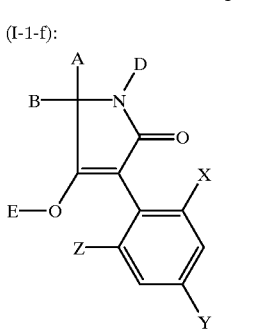

-continued (I-1-g):

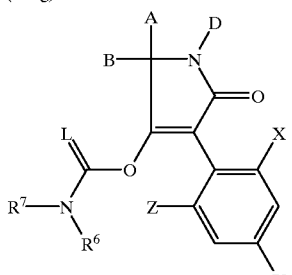

in which

A, B, D, E, L, M, X, Y, Z, $R^1$, $R^2$, $R^3$, $R^4$, $R^5$, $R^6$ and $R^7$ have the meanings given above.

Including the various meanings (a), (b), (c), (d), (e), (f) and (g) of the group G, the following principle structures (I-2-a) to (I-2-g) result if Het is the group (2)

(I-2-a):

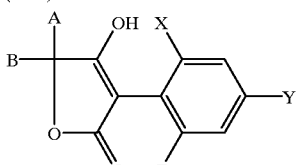

(I-2-b):

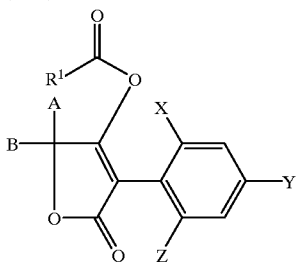

(I-2-c):

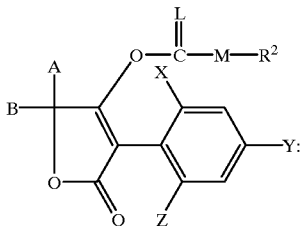

(I-2-d):

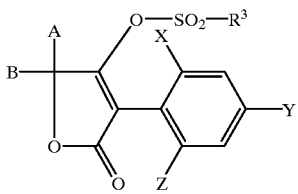

-continued (I-2-e):

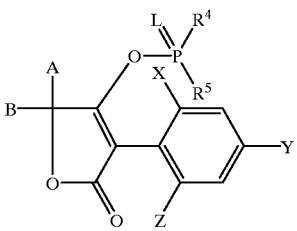

(I-2-f):

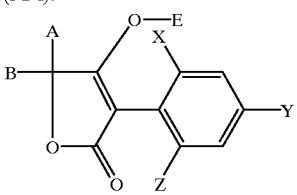

(I-2-g):

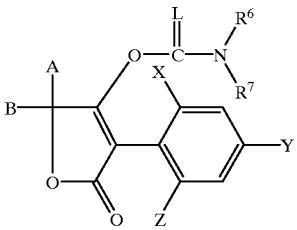

in which

A, B, E, L, M, X, Y, Z, $R^1$, $R^2$, $R^3$, $R^4$, $R^5$, $R^6$ and $R^7$ have the meanings given above.

Including the various meanings (a), (b), (c), (d), (e), (f) and (g) of the group G, the following principle structures (I-3-a) to (I-3-g) result if Het represents the group (3)

(I-3-a):

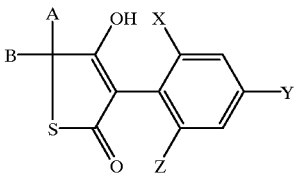

(I-3-b):

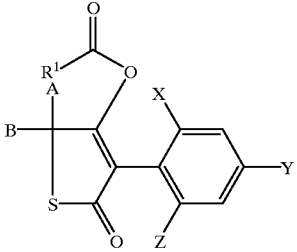

(I-3-c):

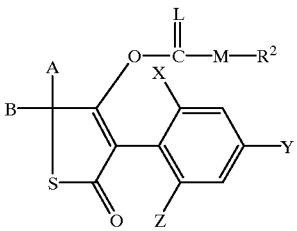

-continued (I-3-d):
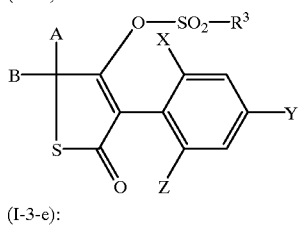

(I-3-e):
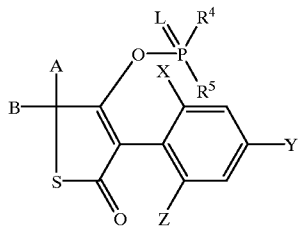

(I-3-f):
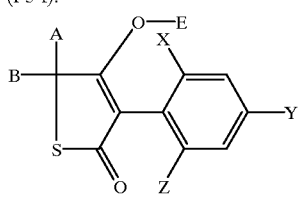

(I-3-g)
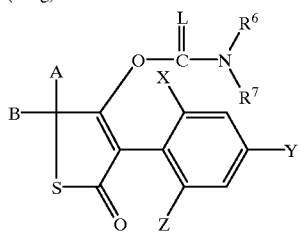

in which
A, B, E, L, M, X, Y, Z, $R^1$, $R^2$, $R^3$, $R^4$, $R^5$, $R^6$ and $R^7$ have the meanings given above.

Depending on the position of the substituent G, the compounds of the formula (I-4) can be present in the two isomeric formulae (I-4)$_a$ and (I-4)$_b$ (I-4)$_a$
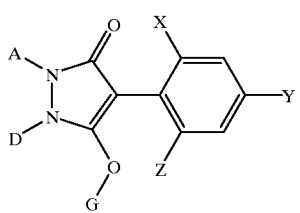

(I-4)$_b$
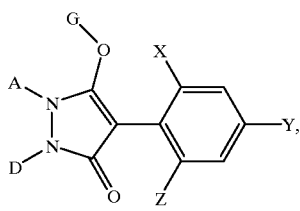

which is intended to be expressed by the dashed line in the formula (I-4):

The compounds of the formulae (I-4)$_a$ and (I-4)$_b$ can be present both as mixtures and in the form of their pure isomers. Mixtures of the compounds of the formula (I-4)$_a$ and (I-4)$_b$ can optionally be separated by physical methods in a manner known per se, for example by chromatographic methods.

For reasons of better clarity, in the following in each case only one of the possible isomers is shown. This does not exclude the fact that the compounds can optionally be present in the form of the isomer mixtures or in the other isomeric form in each case.

Including the various meanings (b), (c), (d), (e), (f) and (g) of the group G, the following principle structures (I-4-b) to (I-4-g) result if Het represents the group (4)

(I-4-b):
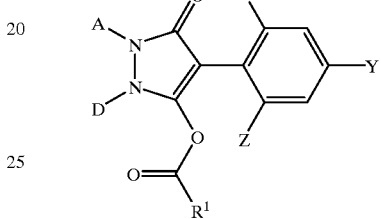

(I-4-c):
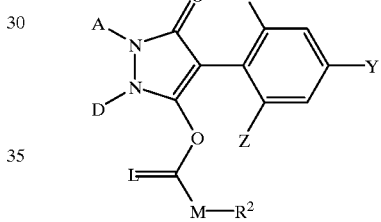

(I-4-d):
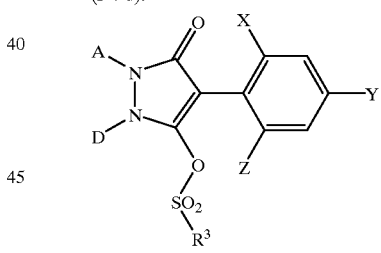

(I-4-e):
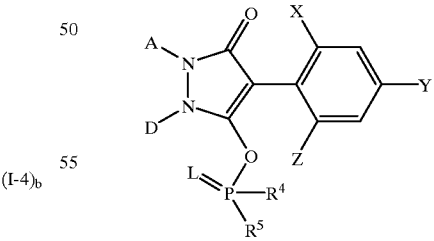

(I-4-f):
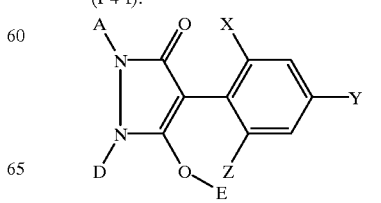

-continued (I-4-g):

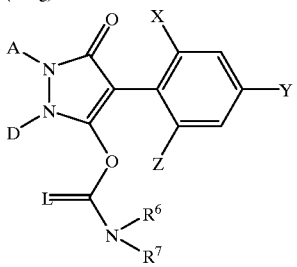

in which

A, D, E, L, M, X, Y, Z, $R^1$, $R^2$, $R^3$, $R^4$, $R^5$, $R^6$ and $R^7$ have the meanings given above.

Depending on the position of the substituent G, the compounds of the formula (I-5) can be present in the two isomeric forms of the formulae $(I-5)_a$ and $(I-5)_b$ $(I-5)_a$

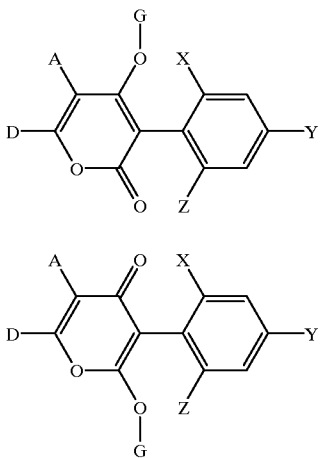

$(I-5)_b$ which is intended to be expressed by the dashed line in the formula (I-5).

The compounds of the formulae $(I-5)_a$ and $(I-5)_b$ can be present both as mixtures and in the form of their pure isomers. Mixtures of the compounds of the formulae $(I-5)_a$ and $(I-5)_b$ can optionally be separated by physical methods in a manner known per se, for example by chromatographic methods.

For reasons of better clarity, in the following in each case only one of the possible isomers is shown. This does not exclude the fact that the compounds can optionally be present in the form of the isomer mixtures or in the other isomeric form in each case.

Including the various meanings (a), (b), (c), (d), (e), (f) and (g) of the group G, the following principle structures (I-5-a) to (I-5-g) result if Het represents the group (5)

(I-5-a):

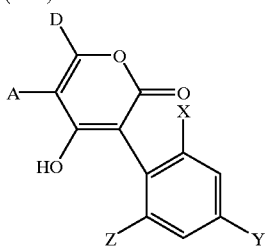

-continued (I-5-b):

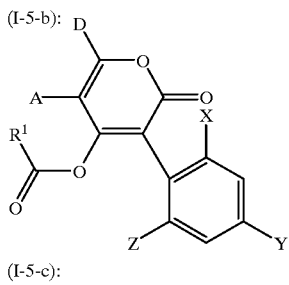

(I-5-c):

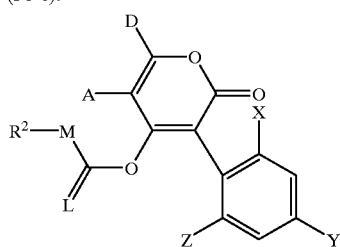

(I-5-d):

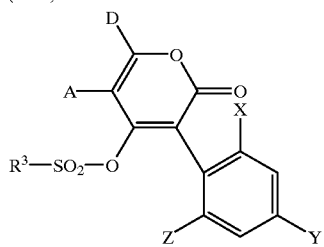

(I-5-e):

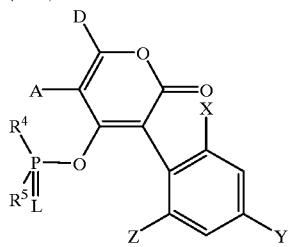

(I-5-f)

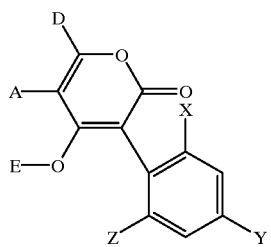

(I-5-g)

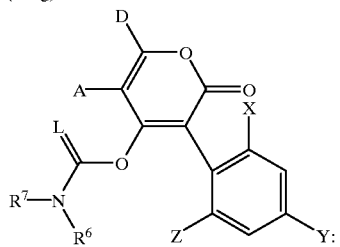

in which

A, D, E, L, M, X, Y, Z, $R^1$, $R^2$, $R^3$, $R^4$, $R^5$, $R^6$ and $R^7$ have the meanings given above.

Including the various meanings (a), (b), (c), (d), (e), (f) and (g) of the group G, the following principle structures (I-6-a) to (I-6-g) result if Het represents the group (6)

(I-6-a):
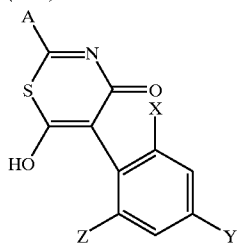

(I-6-b):
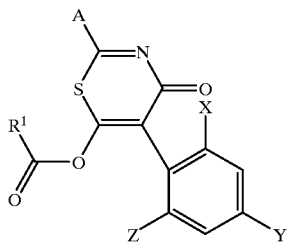

(I-6-c):
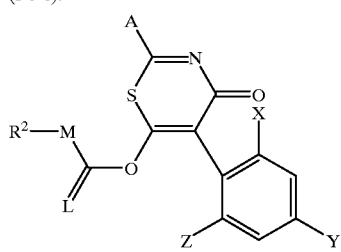

(I-6-d):
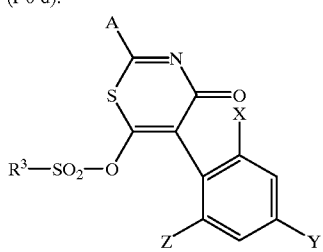

(I-6-e):
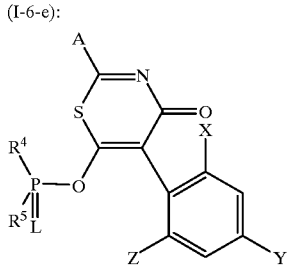

(I-6-f):
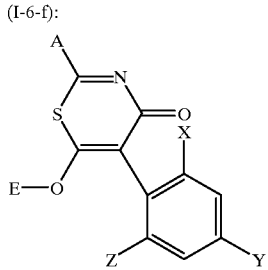

-continued (I-6-g):
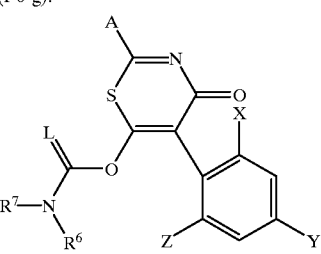

in which

A, E, L, M, X, Y, Z, $R^1$, $R^2$, $R^3$, $R^4$, $R^5$, $R^6$ and $R^7$ have the meanings given above.

It has furthermore been found that the new compounds of the formula (I) are obtained by one of the processes described in the following:

(A) Compounds of the formula (I-1-a)

(I-1-a)

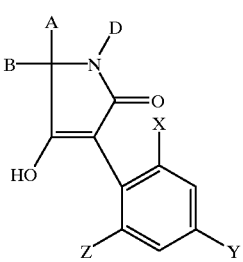

in which

A, B, D, X, Y and Z have the meanings given above, are obtained when compounds of the formula (II)

(II)

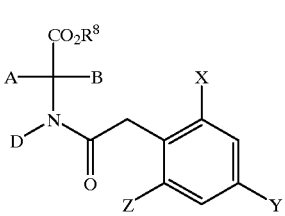

in which

A, B, D, X, Y and Z have the meanings given above, and $R^8$ represents alkyl preferably $C_1$–$C_6$-alkyl), are intramolecularly condensed in the presence of a diluent and in the presence of a base.

(B) It has additionally been found that compounds of the formula (I-2-a)

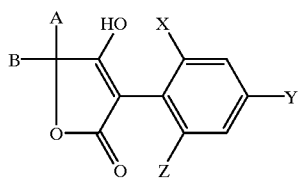
(I-2-a)

in which
A, B, X, Y and Z have the meanings given above,
are obtained when
compounds of the formula (III)

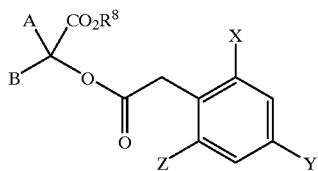
(III)

in which
A, B, X, Y, Z and $R^8$ have the meanings given above,
are intramolecularly condensed in the presence of a diluent and in the presence of a base.

(C) It has furthermore been found that compounds of the formula (I-3-a)

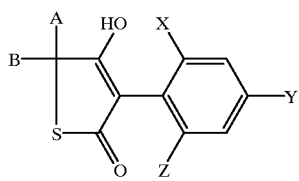
(I-3-a)

in which
A, B, X, Y and Z have the meanings given above,
are obtained when
compounds of the formula (IV)

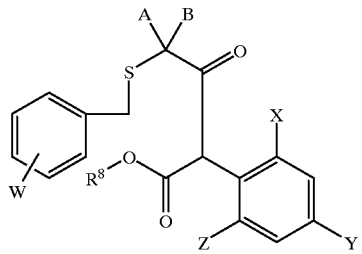
(IV)

in which
A, B, X, Y, Z and $R^8$ have the meanings given above and
W represents hydrogen, halogen, alkyl (preferably $C_1$–$C_6$-alkyl) or alkoxy (preferably $C_1$–$C_8$-alkoxy),
are cyclized, if appropriate in the presence of a diluent and in the presence of an acid.

(E) It has furthermore been found that the compounds of the formula (I-5-a)

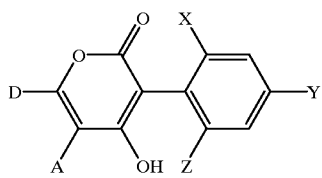
(I-5-a)

in which
A, D, X, Y and Z have the meanings given above,
are obtained when
compounds of the formula (VIII)

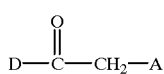
(VIII)

in which
A and D have the meanings given above,
or their silyl enol ethers of the formula (VIIIa)

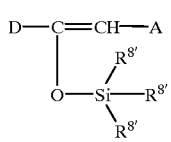
(VIIIa)

in which
A and D have the meanings mentioned above and
$R^{8'}$ represents alkyl (preferably methyl),
are reacted with compounds of the formula (V)

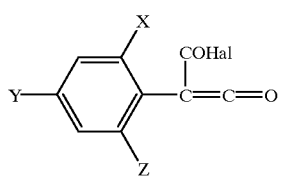
(V)

in which
X, Y and Z have the meanings given above and
Hal represents halogen (preferably chlorine or bromine),
if appropriate in the presence of a diluent and if appropriate in the presence of an acid acceptor.

(F) It has furthermore been found that the compounds of the formula (I-6-a)

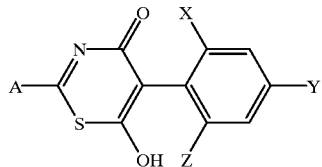
(I-6-a)

in which
A, X, Y and Z have the meanings given above, are obtained when compounds of the formula (IX)

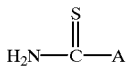  (IX)

in which

A has the meaning given above, are reacted with compounds of the formula (V)

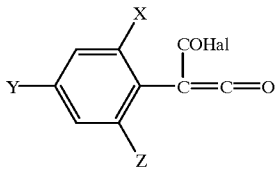  (V)

in which

Hal, X, Y and Z have the meanings given above, if appropriate in the presence of a diluent and if appropriate in the presence of an acid acceptor.

It has additionally been found (G) that the compounds of the formulae (I-1-b) to (I-3-b), (I-5-b) and (I-6-b) shown above, in which A, B, D, $R^1$, X, Y and Z have the meanings given above, are obtained when compounds of the formulae (I-1-a) to (I-3-a), (I-5-a) and (I-6-a) shown above, in which A, B, D, X, Y and Z have the meanings given above, and that compounds of the formula (I-4-b) shown above, in which A, D, $R^1$, X, Y and Z have the meanings given above, are obtained when compounds of the formula (I-4-a)

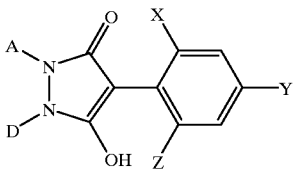  (I-4-a)

in which

A, D, X, Y and Z have the meaning given above, in each case are reacted

α) with acid halides of the formula (X)

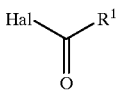  (X)

in which $R^1$ has the meaning given above and

Hal represents halogen (in particular chlorine or bromine)

or

β) with carboxylic anhydrides of the formula (XI)

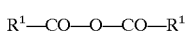  (XI)

in which $R^1$ has the meaning given above, if appropriate in the presence of a diluent and if appropriate in the presence of an acid-binding agent;

(H) that the compounds of the formulae (I-1-c) to (I-6-c) shown above, in which A, B, D, $R^2$, M, X, Y and Z have the meanings given above and L represents oxygen, are obtained when compounds of the formulae (I-1-a) to (I-6-a) shown above, in which A, B, D, X, Y and Z have the meanings given above, in each case are reacted with chloroformic acid esters or chloroformic acid thioesters of the formula (XII)

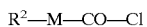  (XII)

in which $R^2$ and M have the meanings given above, if appropriate in the presence of a diluent and if appropriate in the presence of an acid-binding agent;

(I) that compounds of the formulae (I-1-c) to (I-6-c) shown above, in which A, B, D, $R^2$, M, X, Y and Z have the meanings given above and L represents sulphur, are obtained when compounds of the formulae (I-1-a) to (I-6-a) shown above, in which A, B, D, X, Y and Z have the meanings given above, in each case are reacted α) with chloromonothioformic acid esters or chlorodithioformic acid esters of the formula (XIII)

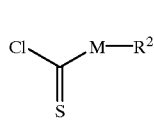  (XIII)

in which

M and $R^2$ have the meanings given above, if appropriate in the presence of a diluent and if appropriate in the presence of an acid-binding agent or β) with carbon disulphide and then with compounds of the formula (XIV)

  (XIV)

in which $R^2$ has the meaning given above and

Hal represents chlorine, bromine or iodine, if appropriate in the presence of a diluent and if appropriate in the presence of a base, (J) that compounds of the formulae (I-1-d) to (I-6-d) shown above, in which A, B, D, $R^3$, X, Y and Z have the meanings given above, are obtained when compounds of the formulae (I-1-a) to (I-6-a) shown above, in which A, B, D, X, Y and Z have the meanings given above, in each case are reacted with sulphonyl chlorides of the formula (XV)

  (XV)

in which $R^3$ has the meaning given above, if appropriate in the presence of a diluent and if appropriate in the presence of an acid-binding agent, (K) that compounds of the formulae (I-1-e) to (I-6-e) shown above, in which A, B, D, L, $R^4$, $R^5$, X, Y and Z have the meanings given above, are obtained when compounds of the formulae (I-1-a) to (I-6-a) shown above, in which A, B, D, X, Y and Z have the meanings given above, in each case are reacted with phosphorus compounds of the formula (XVI)

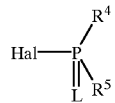

(XVI)

in which

L, $R^4$ and $R^5$ have the meanings given above and

Hal represents halogen (in particular chlorine or bromine), if appropriate in the presence of a diluent and if appropriate in the presence of an acid-binding agent, (L) that compounds of the formulae (I-1-f) to (I-6-f) shown above, in which A, B, D, E, X, Y and Z have the meanings given above, are obtained when compounds of the formulae (I-1-a) to (I-6-a), in which A, B, D, X, Y and Z have the meanings given above, in each case are reacted with metal compounds or amines of the formulae (XVII) or (XVIII)

(XVII)

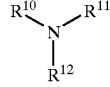

(XVIII)

in which

Me represents a mono- or divalent metal (preferably an alkali metal or alkaline earth metal such as lithium, sodium, potassium, magnesium or calcium), t represents the number 1 or 2 and $R^{10}$, $R^{11}$, $R^{12}$ independently of one another represent hydrogen or alkyl (preferably $C_1$–$C_8$-alkyl), if appropriate in the presence of a diluent, (M) that compounds of the formulae (I-1-g) to (I-6-g) shown above, in which A, B, D, L, $R^6$, $R^7$, X, Y and Z have the meanings given above, are obtained when compounds of the formulae (I-1-a) to (I-6-a) shown above, in which A, B, D, X, Y and Z have the meanings given above, in each case are reacted α) with isocyanates or isothiocyanates of the formula (XIX)

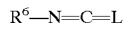

(XIX)

in which $R^6$ and L have the meanings given above, if appropriate in the presence of a diluent and if appropriate in the presence of a catalyst or β) with carbamoyl chlorides or thiocarbamoyl chlorides of the formula (XX)

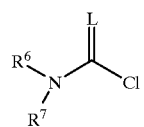

(XX)

in which

L, $R^6$ and $R^7$ have the meanings given above, if appropriate in the presence of a diluent and if appropriate in the presence of an acid-binding agent.

It has furthermore been found that the new compounds of the formula (I) have a very good activity as pesticides, preferably as insecticides, acaricides and herbicides.

Formula (I) provides a general definition of the compounds according to the invention. Preferred substituents or ranges of the radicals shown in the formulae mentioned above and below are illustrated in the following:

X preferably represents $C_1$–$C_6$-alkyl.

Y preferably represents halogen or $C_1$–$C_6$-alkyl.

Z preferably represents halogen or $C_1$–$C_6$-alkyl.

In this case, one of the substituents Y and Z always represents halogen and the other alkyl.

Het preferably represents one of the groups

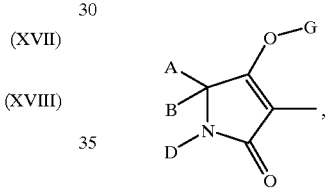

(1)

(2)

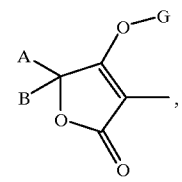

(3)

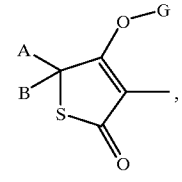

(4)

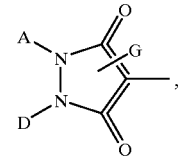

(5)

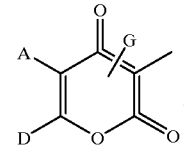

(6)

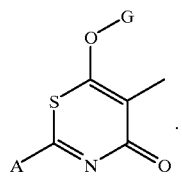

A preferably represents hydrogen, or $C_1$–$C_{12}$-alkyl, $C_2$–$C_8$-alkenyl, $C_1$–$C_{10}$-alkoxy-$C_1$–$C_8$-alkyl, poly-$C_1$–$C_8$-alkoxy-$C_1$–$C_8$-alkyl or $C_1$–$C_{10}$-alkylthio-$C_1$–$C_6$-alkyl, each of which is optionally substituted by halogen, or $C_3$–$C_8$-cycloalkyl which is optionally substituted by halogen, $C_1$–$C_6$-alkyl or $C_1$–$C_6$-alkoxy and in which one or two methylene groups are optionally replaced by oxygen and/or sulphur, or phenyl, naphthyl, phenyl-$C_1$–$C_6$-alkyl, naphthyl-$C_1$–$C_6$-alkyl or hetaryl having 5 or 6 ring atoms and one to three heteroatoms from the series oxygen, sulphur and nitrogen, each of which is optionally substituted by halogen, $C_1$–$C_6$-alkyl, $C_1$–$C_6$-halogenoalkyl, $C_1$–$C_6$-alkoxy, $C_1$–$C_6$-halogenoalkoxy, cyano or nitro, B preferably represents hydrogen, $C_1$–$C_{12}$-alkyl or $C_1$–$C_8$-alkoxy-$C_1$–$C_6$-alkyl, or A, B and the carbon atom to which they are bonded preferably represent $C_3$–$C_{10}$-cycloalkyl or $C_5$–$C_{10}$-cycloalkenyl, in which one methylene group is optionally replaced by oxygen or sulphur and each of which is optionally substituted by $C_1$–$C_8$-alkyl, $C_3$–$C_{10}$-cycloalkyl, $C_1$–$C_8$-halogenoalkyl, $C_1$–$C_8$-alkoxy, $C_1$–$C_8$-alkylthio, halogen or phenyl or A, B and the carbon atom to which they are bonded preferably represent $C_5$–$C_6$-cycloalkyl which is substituted by an alkylenediyl group optionally containing one or two oxygen and/or sulphur atoms, or by an alkylenedioxyl group or by an alkylenedithioyl group which, with the carbon atom to which it is bonded, forms a further five- to eight-membered ring, or A, B and the carbon atom to which they are bonded preferably represent $C_3$–$C_8$-cycloalkyl or $C_5$–$C_8$-cycloalkenyl, in which two substituents, together with the carbon atoms to which they are bonded, represent $C_3$–$C_6$-alkanediyl, $C_3$–$C_6$-alkenediyl or $C_4$–$C_6$-alkanedienediyl, each of which is optionally substituted by $C_1$–$C_6$-alkyl, $C_1$–$C_6$-alkoxy or halogen and in which one methylene group is optionally replaced by oxygen or sulphur in each case.

D preferably represents hydrogen, or $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, poly-$C_1$–$C_8$-alkoxy-$C_2$–$C_8$-alkyl or $C_1$–$C_{10}$-alkylthio-$C_2$–$C_8$-alkyl, each of which is optionally substituted by halogen, or $C_3$–$C_8$-cycloalkyl which is optionally substituted by halogen, $C_1$–$C_4$-alkyl, $C_1$–$C_4$-alkoxy or $C_1$–$C_4$-halogenoalkyl and in which one or two non-directly adjacent methylene groups are optionally replaced by oxygen and/or sulphur, or phenyl, hetaryl having 5 to 6 ring atoms and one or two heteroatoms from the series oxygen, sulphur and nitrogen, phenyl-$C_1$–$C_6$-alkyl or hetaryl-$C_1$–$C_6$-alkyl having 5 to 6 ring atoms and one or two heteroatoms from the series oxygen, sulphur and nitrogen, each of which is optionally substituted by halogen, $C_1$–$C_6$-alkyl, $C_1$–$C_6$-halogenoalkyl, $C_1$–$C_6$-alkoxy, $C_1$–$C_6$-halogenoalkoxy, cyano or nitro, or A and D together preferably represent a $C_3$–$C_6$-alkanediyl, $C_3$–$C_6$-alkenediyl or $C_4$–$C_6$-alkadienediyl group, in which one methylene group in each case is optionally replaced by oxygen or sulphur and each of which is optionally substituted by halogen, hydroxyl, mercapto or $C_1$–$C_{10}$-alkyl, $C_1$–$C_6$-alkoxy, $C_1$–$C_6$-alkylthio, $C_3$–$C_7$-cycloalkyl, phenyl or benzyloxy, each of which is optionally substituted by halogen, or by a further $C_3$–$C_6$-alkanediyl, $C_3$–$C_6$-alkenediyl or $C_4$–$C_6$-alkadienediyl group forming a fused ring and in which one methylene group in each case is optionally replaced by oxygen or sulphur and which is optionally substituted by $C_1$–$C_6$-alkyl or in which two adjacent substituents, together with the carbon atoms to which they are bonded, optionally form a further saturated or unsaturated carbocycle having 5 or 6 ring atoms, or A and D together represent a $C_3$–$C_6$-alkanediyl or $C_3$–$C_6$-alkenediyl group which in each case optionally contains one of the following groups

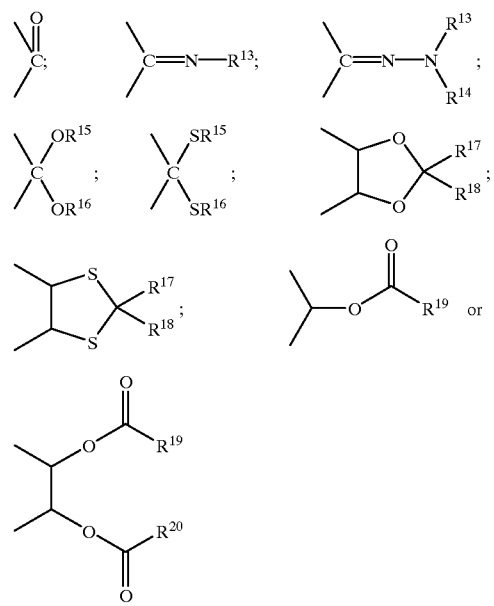

G preferably represents, in the case in which Het represents one of the radicals (1), (2), (3), (5) or (6), hydrogen (a) or, in the case in which Het represents one of the radicals (1), (2), (3), (4), (5) or (6), one of the groups (b)

(c)

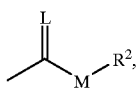

(d)

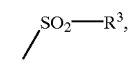

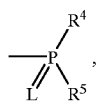
(e)

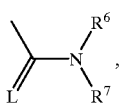
(f) E or (g)

in which
E represents a metal ion equivalent or an ammonium ion,
L represents oxygen or sulphur and
M represents oxygen or sulphur.

$R^1$ preferably represents $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl, each of which is optionally substituted by halogen, or $C_3$–$C_8$-cycloalkyl which is optionally substituted by halogen, $C_1$–$C_6$-alkyl or $C_1$–$C_6$-alkoxy and in which one or two methylene groups are optionally replaced by oxygen and/or sulphur,
  phenyl which is optionally substituted by halogen, cyano, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio or $C_1$–$C_6$-alkylsulphonyl,
  phenyl-$C_1$–$C_6$-alkyl which is optionally substituted by halogen, nitro, cyano, $C_1$–$C_6$-alkyl, $C_1$–$C_6$-alkoxy, $C_1$–$C_6$-halogenoalkyl or $C_1$–$C_6$-halogenoalkoxy,
  5- or 6-membered hetaryl having one or two heteroatoms from the series oxygen, sulphur and nitrogen and which is optionally substituted by halogen or $C_1$–$C_6$-alkyl,
  phenoxy-$C_1$–$C_6$-alkyl which is optionally substituted by halogen or $C_1$–$C_6$-alkyl, or
  5- or 6-membered hetaryloxy-$C_1$–$C_6$-alkyl having one or two heteroatoms from the series oxygen, sulphur and nitrogen and which is optionally substituted by halogen, amino or $C_1$–$C_6$-alkyl.

$R^2$ preferably represents $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, each of which is optionally substituted by halogen,
  $C_3$–$C_8$-cycloalkyl which is optionally substituted by halogen, $C_1$–$C_6$-alkyl or $C_1$–$C_6$-alkoxy, or
    phenyl or benzyl, each of which is optionally substituted by halogen, cyano, nitro, $C_1$–$C_6$-alkyl, $C_1$–$C_6$-alkoxy, $C_1$–$C_6$-halogenoalkyl or $C_1$–$C_6$-halogenoalkoxy.

$R^3$ preferably represents $C_1$–$C_8$-alkyl which is optionally substituted by halogen, or phenyl or benzyl, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

$R^4$ and $R^5$ independently of one another preferably represent $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio or $C_2$–$C_8$-alkenylthio, each of which is optionally substituted by halogen, or phenyl, phenoxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl.

$R^6$ and $R^7$ independently of one another preferably represent hydrogen, or $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_2$–$C_8$-alkyl, each of which is optionally substituted by halogen, or phenyl or benzyl, each of which is optionally substituted by halogen, $C_1$–$C_8$-alkyl, $C_1$–$C_8$-halogenoalkyl or $C_1$–$C_8$-alkoxy or together represent a $C_3$–$C_6$-alkylene radical which is optionally substituted by $C_1$–$C_6$-alkyl and in which a methylene group is optionally replaced by oxygen or sulphur.

$R^{13}$ preferably represents hydrogen or $C_1$–$C_8$-alkyl or $C_1$–$C_8$-alkoxy, each of which is optionally substituted by halogen, or $C_3$–$C_8$-cycloalkyl which is optionally substituted by halogen, $C_1$–$C_4$-alkyl or $C_1$–$C_4$-alkoxy and in which a methylene group is optionally replaced by oxygen or sulphur, or phenyl, phenyl-$C_1$–$C_4$-alkyl or phenyl-$C_1$–$C_4$-alkoxy, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano.

$R^{14}$ preferably represents hydrogen or $C_1$–$C_8$-alkyl, or $R^{13}$ and $R^{14}$ together preferably represent $C_4$–$C_6$-alkanediyl.

$R^{15}$ and $R^{16}$ are identical or different and preferably represent $C_1$–$C_6$-alkyl, or $R^{15}$ and $R^{16}$ together preferably represent a $C_2$–$C_4$-alkanediyl radical which is optionally substituted by $C_1$–$C_6$-alkyl, $C_1$–$C_6$-halogenoalkyl or by phenyl which is optionally substituted by halogen, $C_1$–$C_6$-alkyl, $C_1$–$C_4$-halogenoalkyl, $C_1$–$C_6$-alkoxy, $C_1$–$C_4$-halogenoalkoxy, nitro or cyano.

$R^{17}$ and $R^{18}$ independently of one another preferably represent hydrogen, or $C_1$–$C_8$-alkyl which is optionally substituted by halogen or phenyl which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, or $R^{17}$ and $R^{18}$, together with the carbon atom to which they are bonded, represent a carbonyl group, or $C_5$–$C_7$-cycloalkyl which is optionally substituted by $C_1$–$C_4$-alkyl or $C_1$–$C_4$-alkoxy and in which a methylene group is optionally replaced by oxygen or sulphur.

$R^{19}$ and $R^{20}$ independently of one another preferably represent $C_1$–$C_{10}$-alkyl, $C_2$–$C_{10}$-alkenyl, $C_1$–$C_{10}$-alkoxy, $C_1$–$C_{10}$-alkylamino, $C_3$–$C_{10}$-alkenylamino, di-($C_1$–$C_{10}$-alkyl)amino or di-($C_3$–$C_{10}$-alkenyl)amino.

X particularly preferably represents $C_1$–$C_4$-alkyl.

Y particularly preferably represents fluorine, chlorine, bromine or $C_1$–$C_4$-alkyl.

Z particularly preferably represents fluorine, chlorine, bromine or $C_1$–$C_4$-alkyl.

In this case one of the radicals Y and Z always represents halogen and the other alkyl.

Het particularly preferably represents one of the groups (1)

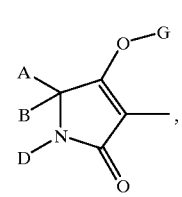

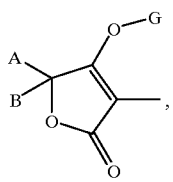 (2)

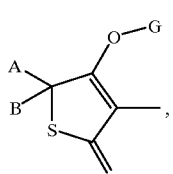 (3)

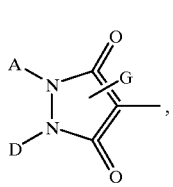 (4)

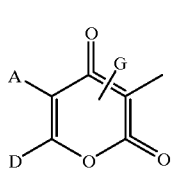 (5)

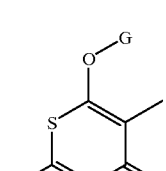 (6)

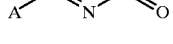

A particularly Preferably represents hydrogen, or $C_1$–$C_{10}$-alkyl, $C_2$–$C_6$-alkenyl, $C_1$–$C_8$-alkoxy-$C_1$–$C_6$-alkyl, poly-$C_1$–$C_6$-alkoxy-$C_1$–$C_6$-alkyl or $C_1$–$C_8$-alkylthio-$C_1$–$C_6$-alkyl, each of which is optionally substituted by fluorine or chlorine, or $C_3$–$C_7$-cycloalkyl which is optionally substituted by fluorine, chlorine, $C_1$–$C_4$-alkyl or $C_1$–$C_4$-alkoxy and in which one or two methylene groups are optionally replaced by oxygen and/or sulphur, or phenyl, furanyl, pyridyl, imidazolyl, triazolyl, pyrazolyl, indolyl, thiazolyl, thienyl or phenyl-$C_1$–$C_4$-alkyl, each of which is optionally substituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano or nitro.

B particularly preferably represents hydrogen, $C_1$–$C_{10}$-alkyl or $C_1$–$C_6$-alkoxy-$C_1$–$C_4$-alkyl or A, B and the carbon atom to which they are bonded particularly preferably represent $C_3$–$C_8$-cycloalkyl or $C_5$–$C_8$-cycloalkenyl, in which in each case a methylene group is optionally replaced by oxygen or sulphur and each of which is optionally substituted by $C_1$–$C_6$-alkyl, $C_3$–$C_8$-cycloalkyl, $C_1$–$C_3$-halogenoalkyl, $C_1$–$C_6$-alkoxy, $C_1$–$C_6$-alkylthio, fluorine, chlorine or phenyl, or A, B and the carbon atom to which they are bonded particularly preferably represent $C_5$–$C_6$-cycloalkyl which is substituted by an alkylenediyl group optionally containing one or two oxygen or sulphur atoms or by an alkylenedioxyl group or by an alkylenedithioyl group and which, with the carbon atom to which it is bonded, forms a further 5- to 7-membered ring, or A, B and the carbon atom to which they are bonded particularly preferably represent $C_3$–$C_6$-cycloalkyl or $C_5$–$C_6$-cycloalkenyl, in which two substituents, together with the carbon atoms to which they are bonded, represent $C_3$–$C_5$-alkanediyl, $C_3$–$C_5$-alkenediyl or butadienediyl, each of which is optionally substituted by $C_1$–$C_5$-alkyl, $C_1$–$C_5$-alkoxy, fluorine, chlorine or bromine, and in which in each case a methylene group is optionally replaced by oxygen or sulphur.

D particularly preferably represents hydrogen, or $C_1$–$C_{10}$-alkyl, $C_3$–$C_6$-alkenyl, $C_3$–$C_6$-alkinyl, $C_1$–$C_8$-alkoxy-$C_2$–$C_6$-alkyl, poly-$C_1$–$C_6$-alkoxy-$C_2$–$C_6$-alkyl or $C_1$–$C_8$-alkylthio-$C_2$–$C_6$-alkyl, each of which is optionally substituted by fluorine or chlorine, $C_3$–$C_7$-cycloalkyl which is optionally substituted by fluorine, chlorine, $C_1$–$C_4$-alkyl, $C_1$–$C_4$-alkoxy or $C_1$–$C_2$-halogenoalkyl and in which one or two non-directly adjacent methylene groups are optionally replaced by oxygen and/or sulphur, or phenyl, furanyl, imidazolyl, pyridyl, thiazolyl, pyrazolyl, pyrimidyl, pyrrolyl, thienyl, triazolyl or phenyl-$C_1$–$C_4$-alkyl, each of which is optionally substituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano or nitro, or A and D together particularly preferably represent a $C_3$–$C_5$-alkanediyl or $C_3$–$C_5$-alkenediyl group, in which in each case a carbon atom is optionally replaced by oxygen or sulphur and each of which is optionally substituted by fluorine, chlorine, hydroxyl, mercapto or by $C_1$–$C_6$-alkyl, $C_1$–$C_4$-alkoxy, $C_1$–$C_4$-alkylthio, $C_3$–$C_6$-cycloalkyl, phenyl or benzoyloxy, each of which is optionally substituted by fluorine or chlorine, or which in each case optionally contains one of the following groups:

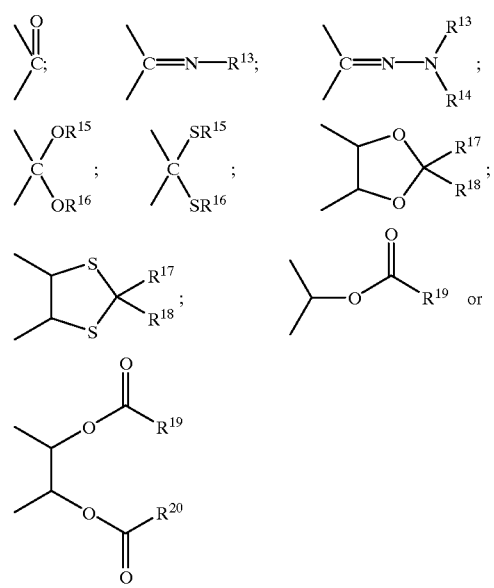

or A and D represent (in the case of the compounds of the formula (I-1)), together with the atoms to which they are bonded, one of the groups AD-1 to AD-27

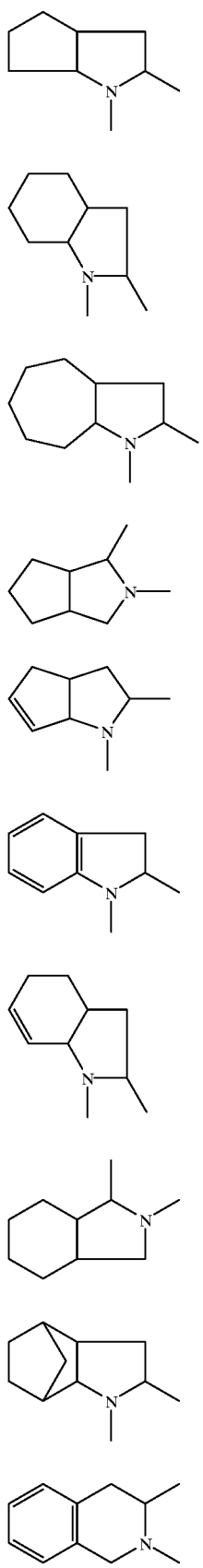
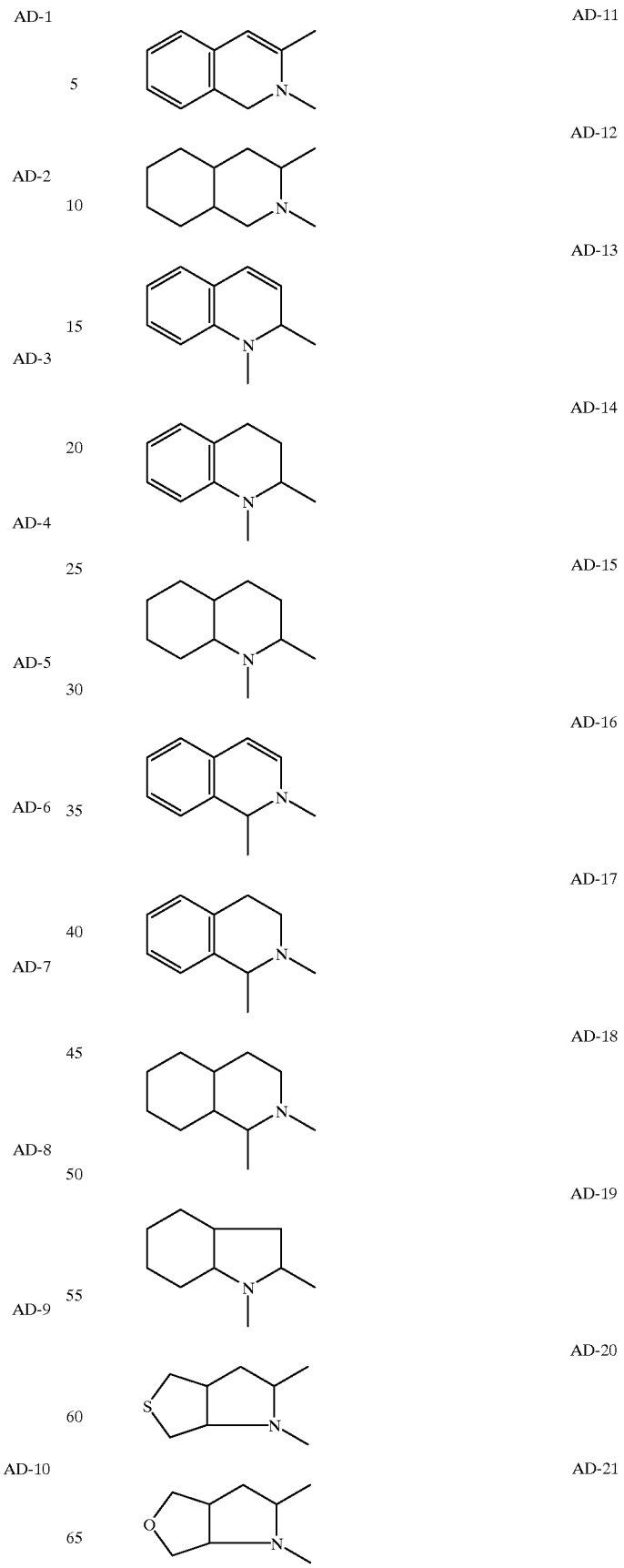

-continued

AD-22 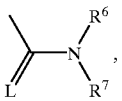
(g)

in which
E represents a metal ion equivalent or an ammonium ion,
L represents oxygen or sulphur and
M represents oxygen or sulphur.

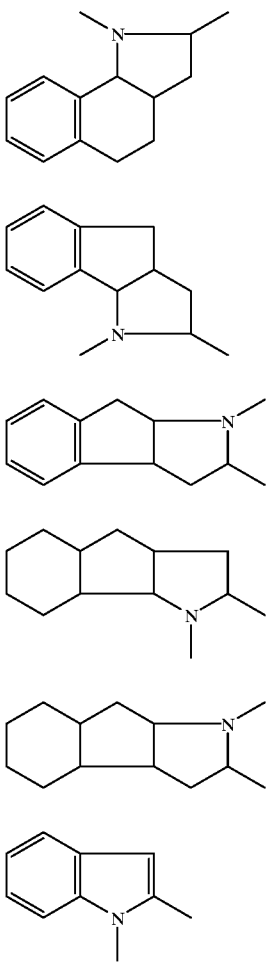

$R^1$ particularly preferably represents $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl, each of which is optionally substituted by fluorine or chlorine, or $C_3$–$C_7$-cycloalkyl which is optionally substituted by fluorine, chlorine, $C_1$–$C_5$-alkyl or $C_1$–$C_5$-alkoxy and in which one or two methylene groups are optionally replaced by oxygen and/or sulphur, phenyl which is optionally substituted by fluorine, chlorine, bromine, cyano, nitro, $C_1$–$C_4$-alkyl, $C_1$–$C_4$-alkoxy, $C_1$–$C_3$-halogenoalkyl, $C_1$–$C_3$-halogenoalkoxy, $C_1$–$C_4$-alkylthio or $C_1$–$C_4$-alkylsulphonyl, phenyl-$C_1$–$C_4$-alkyl which is optionally substituted by fluorine, chlorine, bromine, $C_1$–$C_4$-alkyl, $C_1$–$C_4$-alkoxy, $C_1$–$C_3$-halogenoalkyl or $C_1$–$C_3$-halogenoalkoxy, pyrazolyl, thiazolyl, pyridyl, pyrimidyl, furanyl or thienyl, each of which is optionally substituted by fluorine, chlorine, bromine or $C_1$–$C_4$-alkyl, phenoxy-$C_1$–$C_5$-alkyl which is optionally substituted by fluorine, chlorine, bromine or $C_1$–$C_4$-alkyl, or pyridyloxy-$C_1$–$C_5$-alkyl, pyrimidyloxy-$C_1$–$C_5$-alkyl or thiazolyloxy-$C_1$–$C_5$-alkyl, each of which is optionally substituted by fluorine, chlorine, bromine, amino or $C_1$–$C_4$-alkyl.

$R^2$ particularly preferably represents $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, each of which is optionally substituted by fluorine or chlorine, $C_3$–$C_7$-cycloalkyl which is optionally substituted by fluorine, chlorine, $C_1$–$C_4$-alkyl or $C_1$–$C_4$-alkoxy, or phenyl or benzyl, each of which is optionally substituted by fluorine, chlorine, bromine, cyano, nitro, $C_1$–$C_4$-alkyl, $C_1$–$C_3$-alkoxy, $C_1$–$C_3$-halogenoalkyl or $C_1$–$C_3$-halogenoalkoxy.

$R^3$ particularly preferably represents $C_1$–$C_6$-alkyl which is optionally substituted by fluorine or chlorine, or phenyl or benzyl, each of which is optionally substituted by fluorine, chlorine, bromine, $C_1$–$C_5$-alkyl, $C_1$–$C_5$-alkoxy, $C_1$–$C_3$-halogenoalkyl, $C_1$–$C_3$-halogenoalkoxy, cyano or nitro.

$R^4$ and $R^5$ independently of one another particularly preferably represent $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio or $C_3$–$C_4$-alkenylthio, each of which is optionally substituted by fluorine or chlorine, or phenyl, phenoxy or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl.

$R^6$ and $R^7$ independently of one another particularly preferably represent hydrogen, or $C_1$–$C_6$-alkyl, $C_3$–$C_6$-

G particularly preferably represents, in the case in which Het represents one of the radicals (1), (2), (3), (5) or (6), hydrogen (a) or, in the case in which Het represents one of the radicals (1), (2), (3), (4), (5) or (6), one of the groups

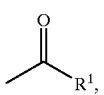
(b)

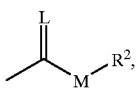
(c)

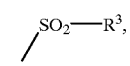
(d)

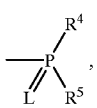
(e)

E (f)

or cycloalkyl, $C_1$–$C_6$-alkoxy, $C_3$–$C_6$-alkenyl or $C_1$–$C_6$-alkoxy-$C_2$–$C_6$-alkyl, each of which is optionally substituted by fluorine or chlorine, or phenyl or benzyl, each of which is optionally substituted by fluorine, chlorine, bromine, $C_1$–$C_5$-halogenoalkyl, $C_1$–$C_5$-alkyl or $C_1$–$C_5$-alkoxy, or together represent a $C_3$–$C_6$-alkylene radical which is optionally substituted by $C_1$–$C_4$-alkyl and in which a methylene group is optionally replaced by oxygen or sulphur.

$R^{13}$ particularly preferably represents hydrogen or $C_1$–$C_6$-alkyl or $C_1$–$C_6$-alkoxy, each of which is optionally substituted by fluorine or chlorine, or $C_3$–$C_7$-cycloalkyl which is optionally substituted by fluorine, $C_1$–$C_2$-alkyl or $C_1$–$C_2$-alkoxy and in which a methylene group is optionally replaced by oxygen or sulphur, or phenyl, phenyl-$C_1$–$C_3$-alkyl or phenyl-$C_1$–$C_2$-alkyloxy, each of which is optionally substituted by fluorine, chlorine, bromine, $C_1$–$C_5$-alkyl, $C_1$–$C_5$-alkoxy, $C_1$–$C_2$-halogenoalkyl, $C_1$–$C_2$-halogenoalkoxy, nitro or cyano.

$R^{14}$ particularly preferably represents hydrogen or $C_1$–$C_6$-alkyl, or $R^{13}$ and $R^{14}$ together particularly preferably represent $C_4$–$C_6$-alkanediyl.

$R^{15}$ and $R^{16}$ are identical or different and particularly preferably represent $C_1$–$C_4$-alkyl, or $R^{15}$ and $R^{16}$ together particularly preferably represent a $C_2$–$C_3$-alkanediyl radical which is optionally substituted by $C_1$–$C_4$-alkyl, $C_1$–$C_4$-halogenoalkyl or by phenyl which is optionally substituted by fluorine, chlorine, bromine, $C_1$–$C_4$-alkyl, $C_1$–$C_2$-halogenoalkyl, $C_1$–$C_4$-alkoxy, $C_1$–$C_2$-halogenoalkoxy, nitro or cyano.

$R^{17}$ and $R^{18}$ independently of one another particularly preferably represent hydrogen, or $C_1$–$C_8$-alkyl which is optionally substituted by fluorine or chlorine, or phenyl which is optionally substituted by fluorine, chlorine, $C_1$–$C_4$-alkyl, $C_1$–$C_4$-alkoxy, $C_1$–$C_2$-halogenoalkyl, $C_1$–$C_2$-halogenoalkoxy, nitro or cyano, or $R^{17}$ and $R^{18}$, together with the carbon atom to which they are bonded, particularly preferably represent $C_5$–$C_6$-cycloalkyl which is optionally substituted by $C_1$–$C_3$-alkyl or $C_1$–$C_3$-alkoxy and in which a methylene group is optionally replaced by oxygen or sulphur.

$R^{19}$ and $R^{20}$ independently of one another particularly preferably represent $C_1$–$C_6$-alkyl, $C_2$–$C_6$-alkenyl, $C_1$–$C_6$-alkoxy, $C_1$–$C_6$-alkylamino, $C_3$–$C_6$-alkenylamino, di-($C_1$–$C_6$-alkyl)amino or di-($C_3$–$C_6$-alkenyl)amino.

X very particularly preferably represents methyl, ethyl, n-propyl or iso-propyl.

Y very particularly preferably represents fluorine, chlorine, bromine, methyl, ethyl, n-propyl or iso-propyl.

Z very particularly preferably represents fluorine, chlorine, bromine, methyl, ethyl, n-propyl or iso-propyl.

In this case one of the radicals Y and Z always represents halogen and the other alkyl.

Het very particularly preferably represents one of the groups

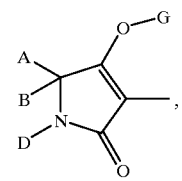 (1)

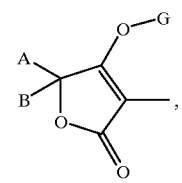 (2)

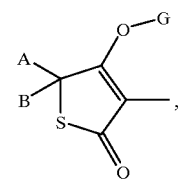 (3)

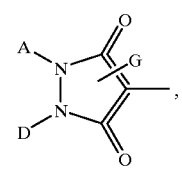 (4)

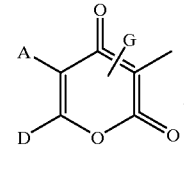 (5)

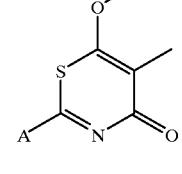 (6)

A very particularly preferably represents hydrogen, or $C_1$–$C_8$-alkyl, $C_2$–$C_4$-alkenyl, $C_1$–$C_6$-alkoxy-$C_1$–$C_4$-alkyl, poly-$C_1$–$C_4$-alkoxy-$C_1$–$C_4$-alkyl or $C_1$–$C_6$-alkylthio-$C_1$–$C_4$-alkyl, each of which is optionally substituted by fluorine or chlorine, or $C_3$–$C_6$-cycloalkyl which is optionally substituted by fluorine, chlorine, methyl or methoxy and in which one or two methylene groups are optionally replaced by oxygen and/or sulphur, or phenyl, furanyl, thienyl, pyridyl or benzyl, each of which is optionally substituted by fluorine, chlorine, bromine, methyl, ethyl, n-propyl, iso-propyl, methoxy, ethoxy, trifluoromethyl, trifluoromethoxy, cyano or nitro.

B very particularly preferably represents hydrogen, $C_1$–$C_8$-alkyl or $C_1$–$C_4$-alkoxy-$C_1$–$C_2$-alkyl, or A, B and the carbon atom to which they are bonded very particularly preferably represent $C_3$–$C_8$-cycloalkyl or $C_5$–$C_8$-cycloalkenyl, in which in each case a methylene group is optionally replaced by oxygen or sulphur and each of which is optionally substituted by methyl, ethyl, n-propyl, iso-propyl, butyl, iso-butyl, sec-butyl, tert-butyl, cyclohexyl, trifluoromethyl, methoxy, ethoxy, n-propoxy, iso-propoxy, butoxy, iso-butoxy, sec-butoxy, tert-butoxy, methylthio, ethylthio, fluorine, chlorine or phenyl, or A, B and the carbon atom to which they are bonded very particularly preferably represent $C_5$–$C_6$-cycloalkyl which is substituted by an alkylenediyl group optionally containing an oxygen or sulphur atom or by an alkylenedioxyl group which, with the carbon atom to which it is bonded, forms a further five- or six-membered ring, or A, B and the carbon atom to which they are bonded very particularly preferably represent $C_3$–$C_6$-cycloalkyl or $C_5$–$C_6$-cycloalkenyl, in which two substituents, together with the carbon atoms to which they are bonded, represent $C_3$–$C_4$-alkanediyl, $C_3$–$C_4$-alkenediyl or butadienediyl, in which in each case a methylene group is optionally replaced by oxygen or sulphur.

D very particularly preferably represents hydrogen, or $C_1$–$C_8$-alkyl, $C_3$–$C_4$-alkenyl, $C_3$–$C_4$-alkinyl, $C_1$–$C_6$-alkoxy-$C_2$–$C_4$-alkyl, poly-$C_1$–$C_4$-alkoxy-$C_2$–$C_4$-alkyl, $C_1$–$C_4$-alkylthio-$C_2$–$C_4$-alkyl or $C_3$–$C_6$-cycloalkyl, each of which is optionally substituted by fluorine or chlorine, and in which one or two non-directly adjacent methylene groups are optionally replaced by oxygen and/or sulphur or phenyl, furanyl, pyridyl, thienyl or benzyl, each of which is optionally substituted by fluorine, chlorine, bromine, methyl, ethyl, n-propyl, iso-propyl, methoxy, ethoxy, trifluoromethyl, trifluoromethoxy, cyano or nitro, or A and D together very particularly preferably represent a $C_3$–$C_5$-alkanediyl or $C_3$–$C_5$-alkenediyl group, in which in each case a methylene group is optionally replaced by oxygen or sulphur and each of which is optionally substituted by fluorine, chlorine, hydroxyl, mercapto or by $C_1$–$C_6$-alkyl, $C_1$–$C_4$-alkoxy, $C_1$–$C_4$-alkylthio, $C_3$–$C_6$-cycloalkyl, phenyl or benzyloxy, each of which is optionally substituted by fluorine or chlorine, or which optionally contains one of the following groups

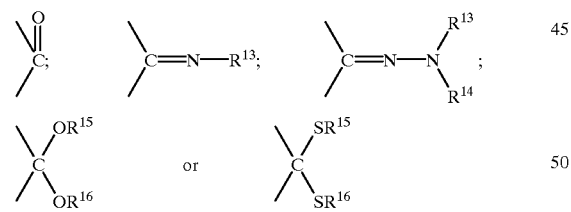

or A and D represent, in the case of the compounds of the formula (I-1), together with the atoms to which they are bonded, one of the following groups:

AD-1

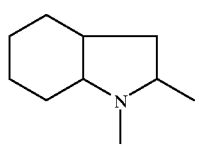

AD-2

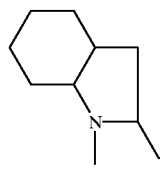

AD-4

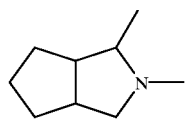

AD-6

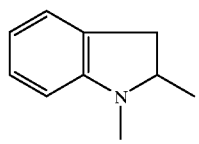

AD-8

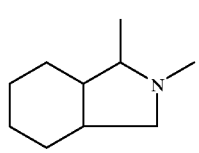

AD-10

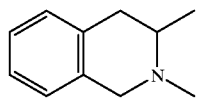

AD-12

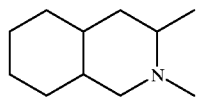

AD-14

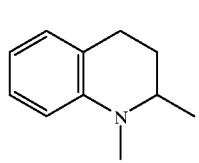

AD-15

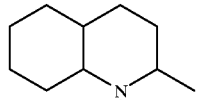

AD-17

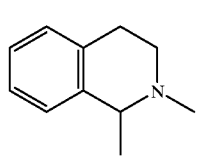

AD-18

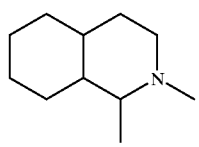

-continued

AD-27

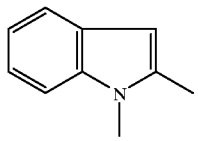

G very particularly preferably represents, in the case in which Het represents one of the radicals (1), (2), (3), (5) or (6), hydrogen (a) or, in the case in which Het represents one of the radicals (1), (2), (3), (4), (5) or (6), one of the groups (b)

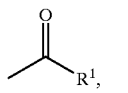

(c)

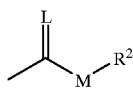

(d)

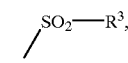

(e)

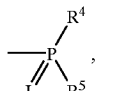

(f)

E or (g)

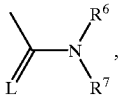

in which
E represents a metal ion equivalent or an ammonium ion,
L represents oxygen or sulphur and
M represents oxygen or sulphur.

$R^1$ very particularly preferably represents $C_1$–$C_4$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl, each of which is optionally substituted by fluorine or chlorine, or $C_3$–$C_6$-cycloalkyl which is optionally substituted by fluorine, chlorine, methyl, ethyl, n-propyl, i-propyl, n-butyl, i-butyl, tert-butyl, methoxy, ethoxy, n-propoxy or iso-propoxy and in which one or two methylene groups are optionally replaced by oxygen and/or sulphur,
phenyl which is optionally substituted by fluorine, chlorine, bromine, cyano, nitro, methyl, ethyl, n-propyl, i-propyl, methoxy, ethoxy, trifluoromethyl, trifluoromhethoxy, methylthio, ethylthio, methylsulphonyl or ethylsulphonyl,
benzyl which is optionally substituted by fluorine, chlorine, bromine, methyl, ethyl, n-propyl, i-propyl, methoxy, ethoxy, trifluoromethyl or trifluoromethoxy,
furanyl, thienyl or pyridyl, each of which is optionally substituted by fluorine, chlorine, bromine, methyl or ethyl,
phenoxy-$C_1$–$C_4$-alkyl which is optionally substituted by fluorine, chlorine, methyl or ethyl, or
pyridyloxy-$C_1$–$C_4$-alkyl, pyrimidyloxy-$C_1$–$C_4$-alkyl or thiazolyloxy-$C_1$–$C_4$-alkyl, each of which is optionally substituted by fluorine, chlorine, amino, methyl or ethyl.

$R^2$ very particularly preferably represents $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, each of which is optionally substituted by fluorine or chlorine,
$C_3$–$C_6$-cycloalkyl which is optionally substituted by fluorine, chlorine, methyl, ethyl, n-propyl, iso-propyl or methoxy,
or phenyl or benzyl, each of which is optionally substituted by fluorine, chlorine, cyano, nitro, methyl, ethyl, n-propyl, i-propyl, methoxy, ethoxy, trifluoromethyl or trifluoromethoxy.

$R^3$ very particularly preferably represents methyl, ethyl, propyl, isopropyl, each of which is optionally substituted by fluorine or chlorine, or phenyl or benzyl, each of which is optionally substituted by fluorine, chlorine, bromine, methyl, ethyl, propyl, iso-propyl, tert-butyl, methoxy, ethoxy, isopropoxy, tert-butoxy, trifluoromethyl, trifluoromethoxy, cyano or nitro.

$R^4$ and $R^5$ independently of one another very particularly preferably represent $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio, each of which is optionally substituted by fluorine or chlorine, or phenyl, phenoxy or phenylthio, each of which is optionally substituted by fluorine, chlorine, bromine, nitro, cyano, methyl, methoxy, trifluoromethyl or trifluoromethoxy.

$R^6$ and $R^7$ independently of one another very particularly preferable represent hydrogen, or $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, each of which is optionally substituted by fluorine or chlorine, or phenyl or benzyl, each of which is optionally substituted by fluorine, chlorine, bromine, methyl, methoxy or trifluoromethyl, or together represent a $C_5$–$C_6$-alkylene radical which is optionally substituted by methyl or ethyl and in which a methylene group is optionally replaced by oxygen or sulphur.

$R^{13}$ very particularly preferably represents hydrogen or $C_1$–$C_4$-alkyl or $C_1$–$C_4$-alkoxy, each of which is optionally substituted by fluorine or chlorine, or $C_3$–$C_6$-cycloalkyl, or phenyl, phenyl-$C_1$–$C_2$-alkyl or benzyloxy, each of which is optionally substituted by fluorine, chlorine, bromine, methyl, ethyl, iso-propyl, tert-butyl, methoxy, ethoxy, iso-propoxy, tert-butoxy, trifluoromethyl, trifluoromethoxy, nitro or cyano.

$R^{14}$ very particularly preferably represents hydrogen or $C_1$–$C_4$-alkyl or $R^{13}$ and $R^{14}$ together very particularly preferably represent $C_4$–$C_6$-alkanediyl.

$R^{15}$ and $R^{16}$ are identical or different and very particularly preferably represent methyl or ethyl or $R^{15}$ and $R^{16}$ together very particularly preferably represent a $C_2$–$C_3$-alkanediyl radical which is optionally substituted by methyl, ethyl, n-propyl, iso-propyl, n-butyl, iso-butyl, sec-butyl, tert-butyl or by phenyl which is optionally substituted by fluorine, chlorine, methoxy, trifluoromethyl, trifluoromethoxy, nitro or cyano.

The abovementioned definitions or explanations of radicals mentioned generally or in preferred ranges can be combined with one another as desired, i.e. also between the respective ranges and preferred ranges. They apply correspondingly to the final products and to the precursors and intermediates.

Preferred compounds of the formula (I) according to the invention are those in which a combination of the meanings (preferably) mentioned above as preferred is present.

Particularly preferred compounds of the formula (I) according to the invention are those in which a combination of the meanings mentioned above as particularly preferred is present.

Very particularly preferred compounds of the formula (I) according to the invention are those in which a combination of the meanings mentioned above as very particularly preferred is present.

Saturated or unsaturated hydrocarbon radicals such as alkyl or alkenyl can, as far as possible, in each case be straight-chain or branched, even in combination with heteroatoms, e.g. in alkoxy.

Optionally substituted radicals can be mono- or polysubstituted, it being possible in the case of polysubstitution for the substituents to be identical or different.

In addition to the compounds mentioned in the Preparation Examples, the following compounds of the formula (I-1-a) may be specifically mentioned:

TABLE 1

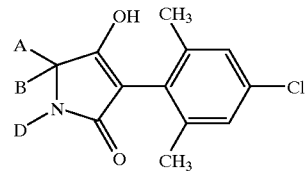

| A | B | D |
|---|---|---|
| $CH_3$ | H | H |
| $C_2H_5$ | H | H |
| $C_3H_7$ | H | H |
| $i-C_3H_7$ | H | H |
| $C_4H_9$ | H | H |
| $i-C_4H_9$ | H | H |
| $s-C_4H_9$ | H | H |
| $t-C_4H_9$ | H | H |
| $CH_3$ | $CH_3$ | H |
| $C_2H_5$ | $CH_3$ | H |
| $C_3H_7$ | $CH_3$ | H |
| $i-C_3H_7$ | $CH_3$ | H |
| $C_4H_9$ | $CH_3$ | H |
| $i-C_4H_9$ | $CH_3$ | H |
| $s-C_4H_9$ | $CH_3$ | H |
| $t-C_4H_9$ | $CH_3$ | H |
| $C_2H_5$ | $C_2H_5$ | H |
| $C_3H_7$ | $C_3H_7$ | H |
| cyclopropyl | $CH_3$ | H |
| cyclopentyl | $CH_3$ | H |
| cyclohexyl | $CH_3$ | H |
| $-(CH_2)_2-$ | | H |
| $-(CH_2)_4-$ | | H |
| $-(CH_2)_5-$ | | H |

TABLE 1-continued

| A | B | D |
|---|---|---|
| | $-(CH_2)_6-$ | H |
| | $-(CH_2)_7-$ | H |
| | $-(CH_2)_2-O-(CH_2)_2-$ | H |
| | $-(CH_2)_2-S-(CH_2)_2-$ | H |
| | $-CH_2-CHCH_3-(CH_2)_3-$ | H |
| | $-(CH_2)_2-CHCH_3-(CH_2)_2-$ | H |
| | $-(CH_2)_2-CHC_2H_5-(CH_2)_2-$ | H |
| | $-(CH_2)_2-CHC_3H_7-(CH_2)_2-$ | H |
| | $-(CH_2)_2-CHi-C_3H_7-(CH_2)_2-$ | H |
| | $-(CH_2)_2-CHOCH_3-(CH_2)_2-$ | H |
| | $-(CH_2)_2-CHOC_2H_5-(CH_2)_2-$ | H |
| | $-(CH_2)_2-CHOC_3H_7-(CH_2)_2-$ | H |
| | $-(CH_2)_2-CHi-OC_3H_7-(CH_2)_2-$ | H |
| | $-(CH_2)_2-C(CH_3)_2-(CH_2)_2-$ | H |
| | $-CH_2-(CHCH_3)_2-(CH_2)_2-$ | H |
| | $-CH_2-CH-(CH_2)_2-CH-$ with $-CH_2-$ bridge | H |
| | $-CH_2-CH-\ldots-CH-CH_2-$ with $-(CH_2)_4-$ bridge | H |
| | $-CH_2-CH-\ldots-CH-(CH_2)_2-$ with $-(CH_2)_3-$ bridge | H |
| | indanyl | H |
| | tetrahydronaphthyl | H |
| | $-(CH_2)_3-$ | H |
| | $-(CH_2)_4-$ | H |
| | $-CH_2-CHCH_3-CH_2-$ | H |
| | $-CH_2-CH_2-CHCH_3-$ | H |
| | $-CH_2-CHCH_3-CHCH_3-$ | H |
| | $-CH_2-S-CH_2-$ | H |
| | $-CH_2-S-(CH_2)_2-$ | H |
| | $-(CH_2)_2-S-CH_2-$ | H |
| | $-CH_2-CH-\ldots-CH-$ with $-(CH_2)_3-$ bridge | H |
| H | $CH_3$ | H |
| H | $C_2H_5$ | H |
| H | $C_3H_7$ | H |
| H | $i-C_3H_7$ | H |
| H | cyclopropyl | H |

TABLE 1-continued

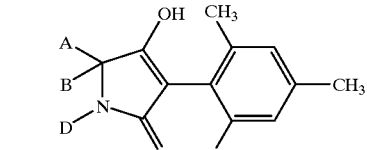

| A | B | D |
|---|---|---|
| H | 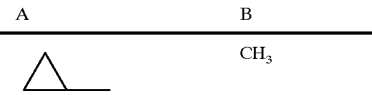 | H |
| H |  | H |
| CH₃ | CH₃ | H |
| CH₃ | C₂H₅ | H |
| CH₃ | C₃H₇ | H |
| CH₃ | i-C₃H₇ | H |
| CH₃ | 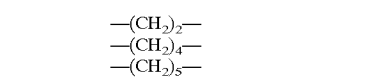 | H |
| CH₃ | 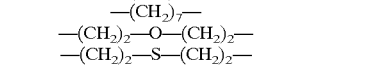 | H |
| CH₃ | 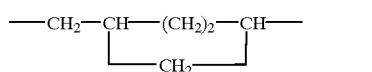 | H |
| C₂H₅ | CH₃ | H |
| C₂H₅ | C₂H₅ | H |

TABLE 2

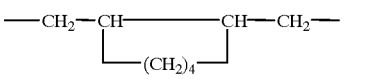

| A | B | D |
|---|---|---|
| CH₃ | H | H |
| C₂H₅ | H | H |
| C₃H₇ | H | H |
| i-C₃H₇ | H | H |
| C₄H₉ | H | H |
| i-C₄H₉ | H | H |
| s-C₄H₉ | H | H |
| t-C₄H₉ | H | H |
| CH₃ | CH₃ | H |
| C₂H₅ | CH₃ | H |
| C₃H₇ | CH₃ | H |
| i-C₃H₇ | CH₃ | H |
| C₄H₉ | CH₃ | H |
| i-C₄H₉ | CH₃ | H |
| s-C₄H₉ | CH₃ | H |
| t-C₄H₉ | CH₃ | H |
| C₂H₅ | C₂H₅ | H |
| C₃H₇ | C₃H₇ | H |

TABLE 2-continued

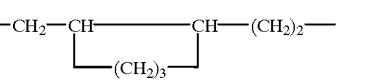

| A | B | D |
|---|---|---|
| 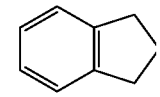 | CH₃ | H |
| 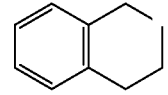 | CH₃ | H |
| 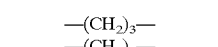 | CH₃ | H |
| —(CH₂)₂— | | H |
| —(CH₂)₄— | | H |
| —(CH₂)₅— | | H |
| —(CH₂)₆— | | H |
| —(CH₂)₇— | | H |
| —(CH₂)₂—O—(CH₂)₂— | | H |
| —(CH₂)₂—S—(CH₂)₂— | | H |
| —CH₂—CHCH₃—(CH₂)₃— | | H |
| —(CH₂)₂—CHCH₃—(CH₂)₂— | | H |
| —(CH₂)₂—CHC₂H₅—(CH₂)₂— | | H |
| —(CH₂)₂—CHC₃H₇—(CH₂)₂— | | H |
| —(CH₂)₂—CHi-C₃H₇—(CH₂)₂— | | H |
| —(CH₂)₂—CHOCH₃—(CH₂)₂— | | H |
| —(CH₂)₂—CHOC₂H₅—(CH₂)₂— | | H |
| —(CH₂)₂—CHOC₃H₇—(CH₂)₂— | | H |
| —(CH₂)₂—CHi-OC₃H₇—(CH₂)₂— | | H |
| —(CH₂)₂—C(CH₃)₂—(CH₂)₂— | | H |
| —CH₂—(CHCH₃)₂—(CH₂)₂— | | H |
| 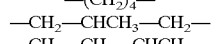 | | H |
| 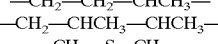 | | H |
| 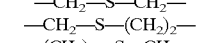 | | H |
| 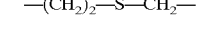 | | H |
|  | | H |
| —(CH₂)₃— | | H |
| —(CH₂)₄— | | H |
| —CH₂—CHCH₃—CH₂— | | H |
| —CH₂—CH₂—CHCH₃— | | H |
| —CH₂—CHCH₃—CHCH₃— | | H |
| —CH₂—S—CH₂— | | H |
| —CH₂—S—(CH₂)₂— | | H |
| —(CH₂)₂—S—CH₂— | | H |

TABLE 2-continued

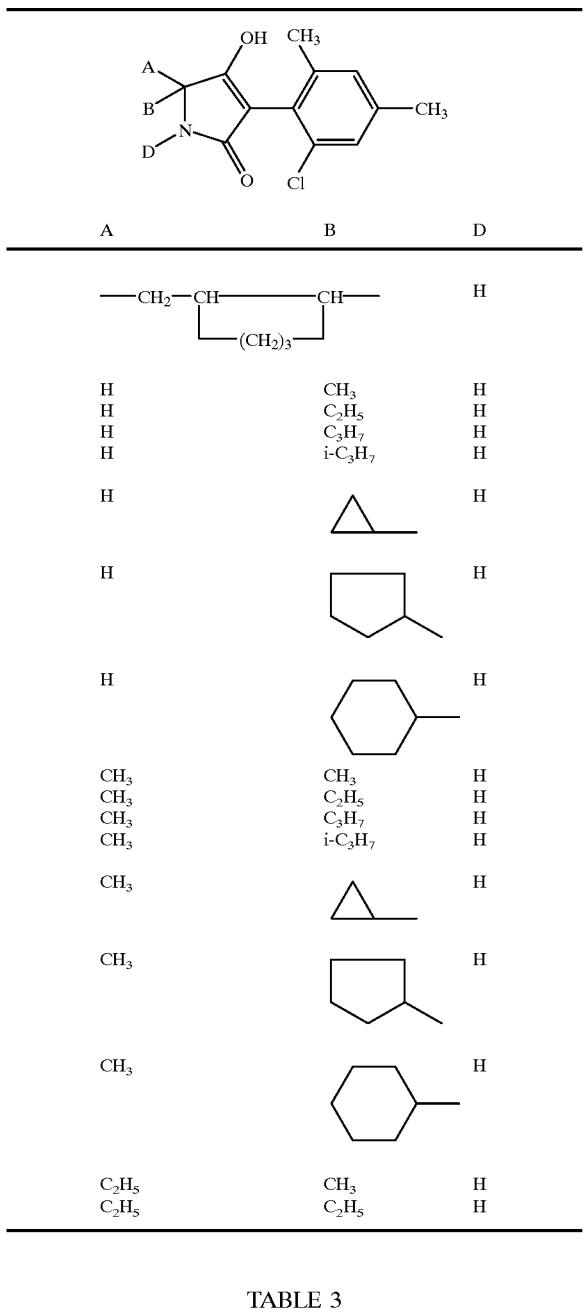

| A | B | D |
|---|---|---|
| —CH₂—CH—(CH₂)₃—CH— (bridged) | | H |
| H | CH₃ | H |
| H | C₂H₅ | H |
| H | C₃H₇ | H |
| H | i-C₃H₇ | H |
| H | cyclopropyl | H |
| H | cyclopentyl | H |
| H | cyclohexyl | H |
| CH₃ | CH₃ | H |
| CH₃ | C₂H₅ | H |
| CH₃ | C₃H₇ | H |
| CH₃ | i-C₃H₇ | H |
| CH₃ | cyclopropyl | H |
| CH₃ | cyclopentyl | H |
| CH₃ | cyclohexyl | H |
| C₂H₅ | CH₃ | H |
| C₂H₅ | C₂H₅ | H |

TABLE 3

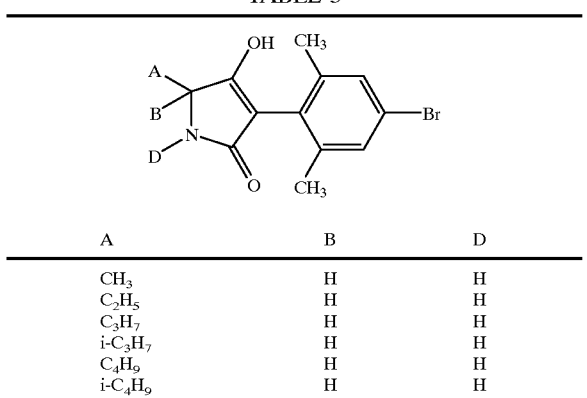

| A | B | D |
|---|---|---|
| CH₃ | H | H |
| C₂H₅ | H | H |
| C₃H₇ | H | H |
| i-C₃H₇ | H | H |
| C₄H₉ | H | H |
| i-C₄H₉ | H | H |

TABLE 3-continued

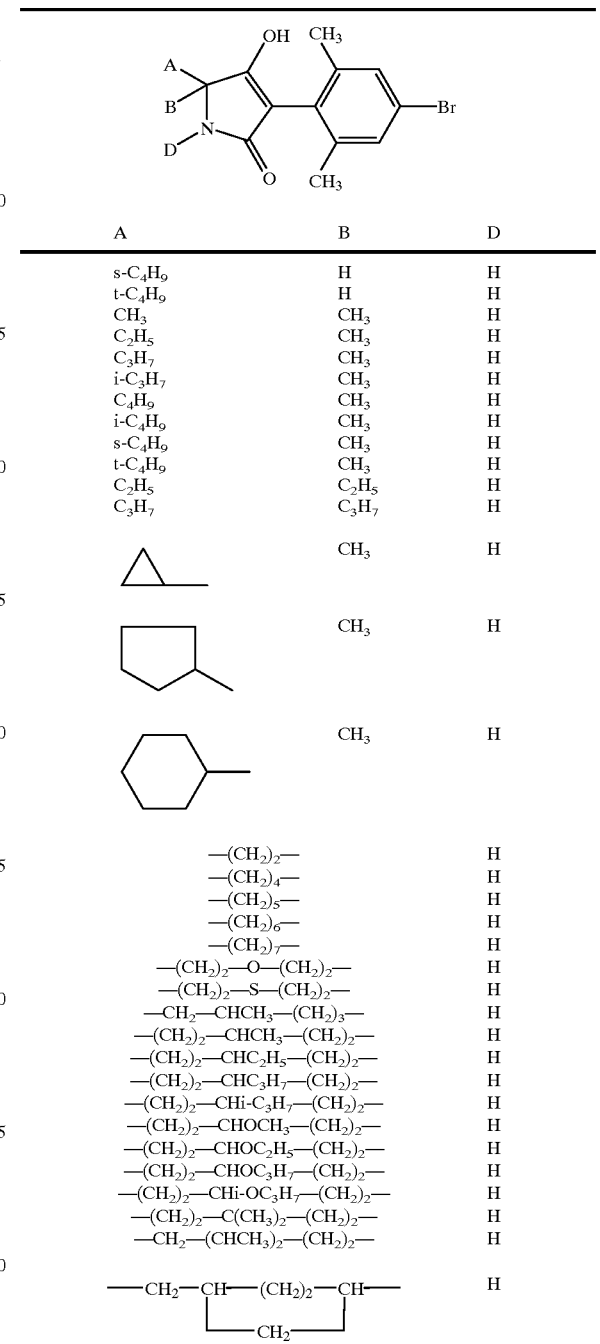

| A | B | D |
|---|---|---|
| s-C₄H₉ | H | H |
| t-C₄H₉ | H | H |
| CH₃ | CH₃ | H |
| C₂H₅ | CH₃ | H |
| C₃H₇ | CH₃ | H |
| i-C₃H₇ | CH₃ | H |
| C₄H₉ | CH₃ | H |
| i-C₄H₉ | CH₃ | H |
| s-C₄H₉ | CH₃ | H |
| t-C₄H₉ | CH₃ | H |
| C₂H₅ | C₂H₅ | H |
| C₃H₇ | C₃H₇ | H |
| cyclopropyl | CH₃ | H |
| cyclopentyl | CH₃ | H |
| cyclohexyl | CH₃ | H |
| —(CH₂)₂— | | H |
| —(CH₂)₄— | | H |
| —(CH₂)₅— | | H |
| —(CH₂)₆— | | H |
| —(CH₂)₇— | | H |
| —(CH₂)₂—O—(CH₂)₂— | | H |
| —(CH₂)₂—S—(CH₂)₂— | | H |
| —CH₂—CHCH₃—(CH₂)₃— | | H |
| —(CH₂)₂—CHCH₃—(CH₂)₂— | | H |
| —(CH₂)₂—CHC₂H₅—(CH₂)₂— | | H |
| —(CH₂)₂—CHC₃H₇—(CH₂)₂— | | H |
| —(CH₂)₂—CHi-C₃H₇—(CH₂)₂— | | H |
| —(CH₂)₂—CHOCH₃—(CH₂)₂— | | H |
| —(CH₂)₂—CHOC₂H₅—(CH₂)₂— | | H |
| —(CH₂)₂—CHOC₃H₇—(CH₂)₂— | | H |
| —(CH₂)₂—CHi-OC₃H₇—(CH₂)₂— | | H |
| —(CH₂)₂—C(CH₃)₂—(CH₂)₂— | | H |
| —CH₂—(CHCH₃)₂—(CH₂)₂— | | H |
| —CH₂—CH—(CH₂)₂—CH—CH₂— (bridged) | | H |
| —CH₂—CH—(CH₂)₄—CH—CH₂— (bridged) | | H |
| —CH₂—CH—CH—(CH₂)₂—(CH₂)₃— (bridged) | | H |
| indanyl | | H |

TABLE 3-continued

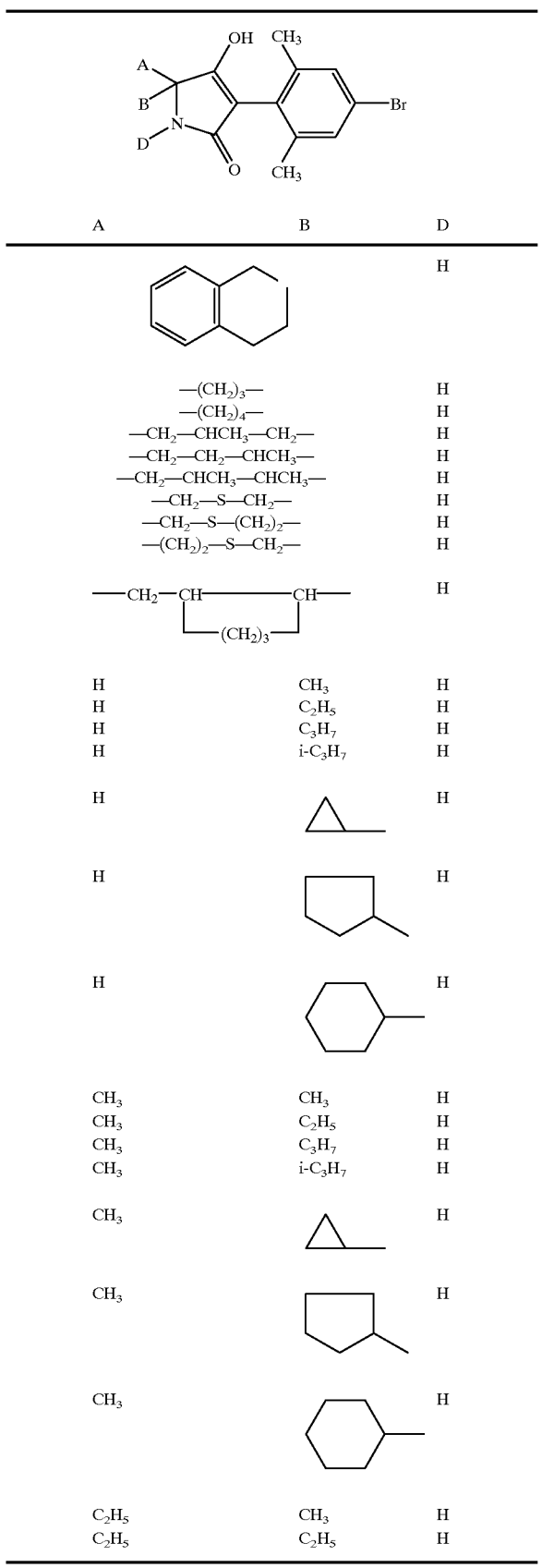

| A | B | D |
|---|---|---|
| (tetrahydronaphthyl group) | | H |
| —(CH₂)₃— | | H |
| —(CH₂)₄— | | H |
| —CH₂—CHCH₃—CH₂— | | H |
| —CH₂—CH₂—CHCH₃— | | H |
| —CH₂—CHCH₃—CHCH₃— | | H |
| —CH₂—S—CH₂— | | H |
| —CH₂—S—(CH₂)₂— | | H |
| —(CH₂)₂—S—CH₂— | | H |
| —CH₂—CH—CH— with (CH₂)₃ bridge | | H |
| H | CH₃ | H |
| H | C₂H₅ | H |
| H | C₃H₇ | H |
| H | i-C₃H₇ | H |
| H | cyclopropyl | H |
| H | cyclopentyl | H |
| H | cyclohexyl | H |
| CH₃ | CH₃ | H |
| CH₃ | C₂H₅ | H |
| CH₃ | C₃H₇ | H |
| CH₃ | i-C₃H₇ | H |
| CH₃ | cyclopropyl | H |
| CH₃ | cyclopentyl | H |
| CH₃ | cyclohexyl | H |
| C₂H₅ | CH₃ | H |
| C₂H₅ | C₂H₅ | H |

TABLE 4

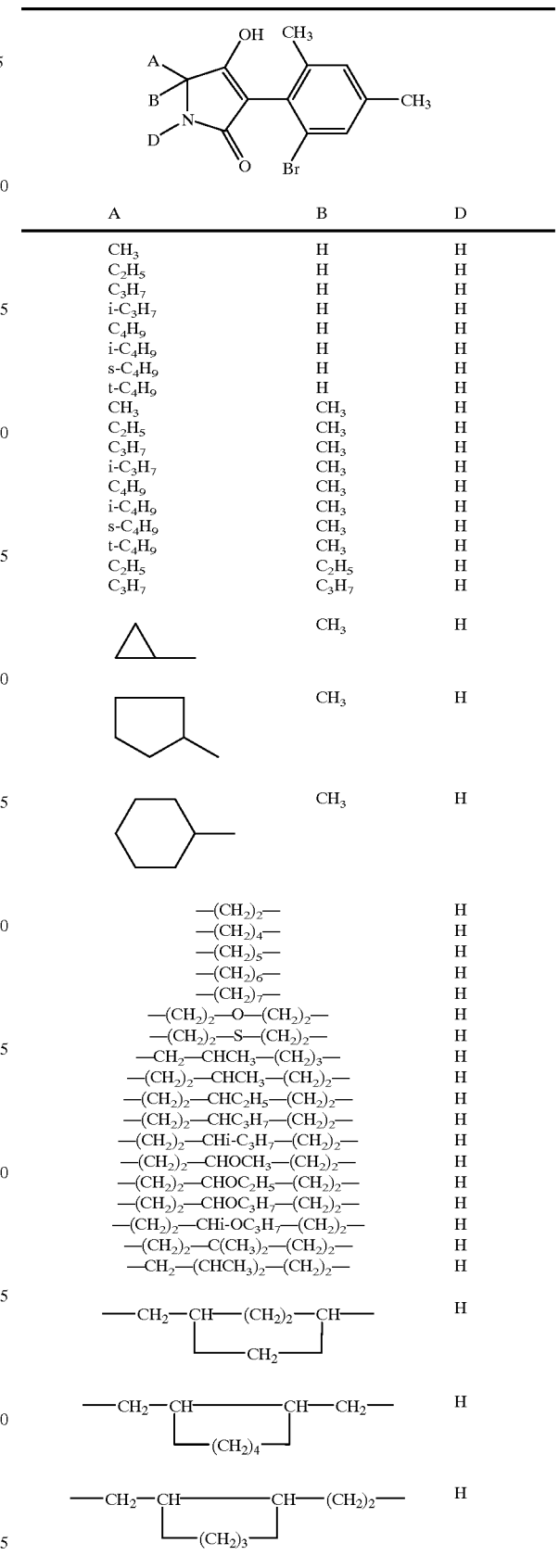

| A | B | D |
|---|---|---|
| CH₃ | H | H |
| C₂H₅ | H | H |
| C₃H₇ | H | H |
| i-C₃H₇ | H | H |
| C₄H₉ | H | H |
| i-C₄H₉ | H | H |
| s-C₄H₉ | H | H |
| t-C₄H₉ | H | H |
| CH₃ | CH₃ | H |
| C₂H₅ | CH₃ | H |
| C₃H₇ | CH₃ | H |
| i-C₃H₇ | CH₃ | H |
| C₄H₉ | CH₃ | H |
| i-C₄H₉ | CH₃ | H |
| s-C₄H₉ | CH₃ | H |
| t-C₄H₉ | CH₃ | H |
| C₂H₅ | C₂H₅ | H |
| C₃H₇ | C₃H₇ | H |
| cyclopropyl | CH₃ | H |
| cyclopentyl | CH₃ | H |
| cyclohexyl | CH₃ | H |
| —(CH₂)₂— | | H |
| —(CH₂)₄— | | H |
| —(CH₂)₅— | | H |
| —(CH₂)₆— | | H |
| —(CH₂)₇— | | H |
| —(CH₂)₂—O—(CH₂)₂— | | H |
| —(CH₂)₂—S—(CH₂)₂— | | H |
| —CH₂—CHCH₃—(CH₂)₃— | | H |
| —(CH₂)₂—CHCH₃—(CH₂)₂— | | H |
| —(CH₂)₂—CHC₂H₅—(CH₂)₂— | | H |
| —(CH₂)₂—CHC₃H₇—(CH₂)₂— | | H |
| —(CH₂)₂—CHi-C₃H₇—(CH₂)₂— | | H |
| —(CH₂)₂—CHOCH₃—(CH₂)₂— | | H |
| —(CH₂)₂—CHOC₂H₅—(CH₂)₂— | | H |
| —(CH₂)₂—CHOC₃H₇—(CH₂)₂— | | H |
| —(CH₂)₂—CHi-OC₃H₇—(CH₂)₂— | | H |
| —(CH₂)₂—C(CH₃)₂—(CH₂)₂— | | H |
| —CH₂—(CHCH₃)₂—(CH₂)₂— | | H |
| —CH₂—CH—(CH₂)₂—CH— with CH₂ bridge | | H |
| —CH₂—CH—CH—CH₂— with (CH₂)₄ bridge | | H |
| —CH₂—CH—CH—(CH₂)₂— with (CH₂)₃ bridge | | H |

TABLE 4-continued

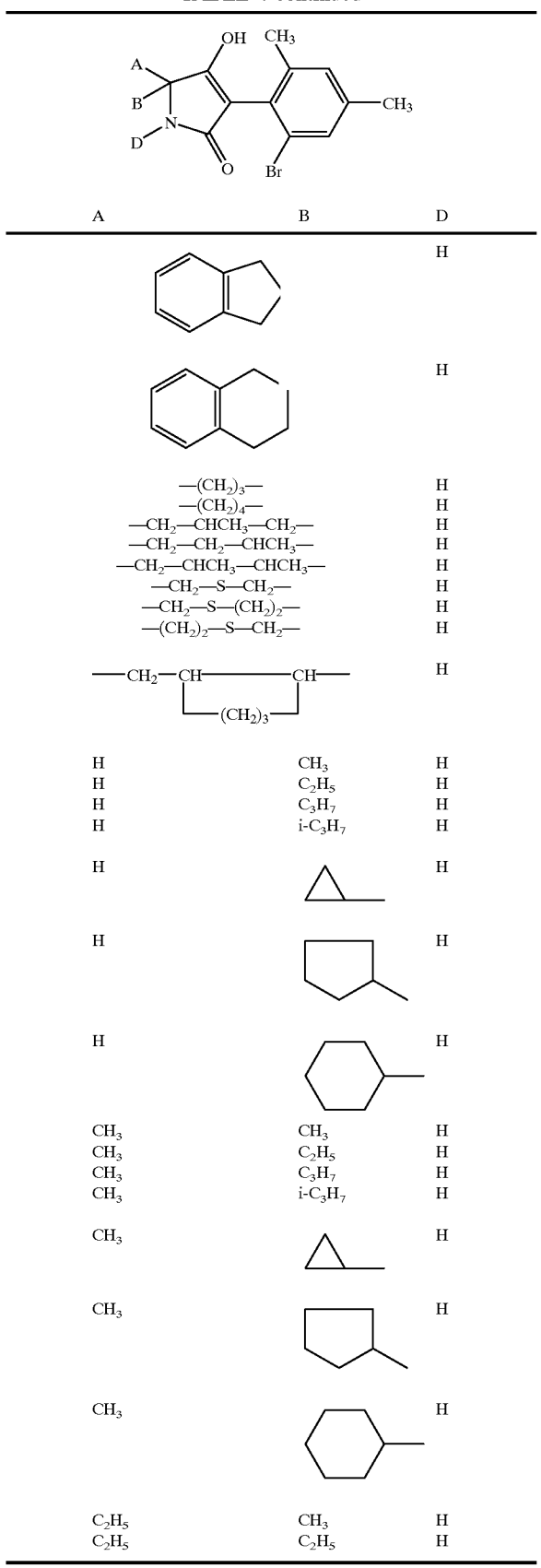

| A | B | D |
|---|---|---|
| (indanyl) | | H |
| (tetrahydronaphthyl) | | H |
| —(CH$_2$)$_3$— | | H |
| —(CH$_2$)$_4$— | | H |
| —CH$_2$—CHCH$_3$—CH$_2$— | | H |
| —CH$_2$—CH$_2$—CHCH$_3$— | | H |
| —CH$_2$—CHCH$_3$—CHCH$_3$— | | H |
| —CH$_2$—S—CH$_2$— | | H |
| —CH$_2$—S—(CH$_2$)$_2$— | | H |
| —(CH$_2$)$_2$—S—CH$_2$— | | H |
| —CH$_2$—CH—(CH$_2$)$_3$—CH— | | H |
| H | CH$_3$ | H |
| H | C$_2$H$_5$ | H |
| H | C$_3$H$_7$ | H |
| H | i-C$_3$H$_7$ | H |
| H | cyclopropyl | H |
| H | cyclopentyl | H |
| H | cyclohexyl | H |
| CH$_3$ | CH$_3$ | H |
| CH$_3$ | C$_2$H$_5$ | H |
| CH$_3$ | C$_3$H$_7$ | H |
| CH$_3$ | i-C$_3$H$_7$ | H |
| CH$_3$ | cyclopropyl | H |
| CH$_3$ | cyclopentyl | H |
| CH$_3$ | cyclohexyl | H |
| C$_2$H$_5$ | CH$_3$ | H |
| C$_2$H$_5$ | C$_2$H$_5$ | H |

In addition to the compounds mentioned in the Preparation Examples, the following compounds of the formula (I-2-a) may specifically be mentioned:

TABLE 5

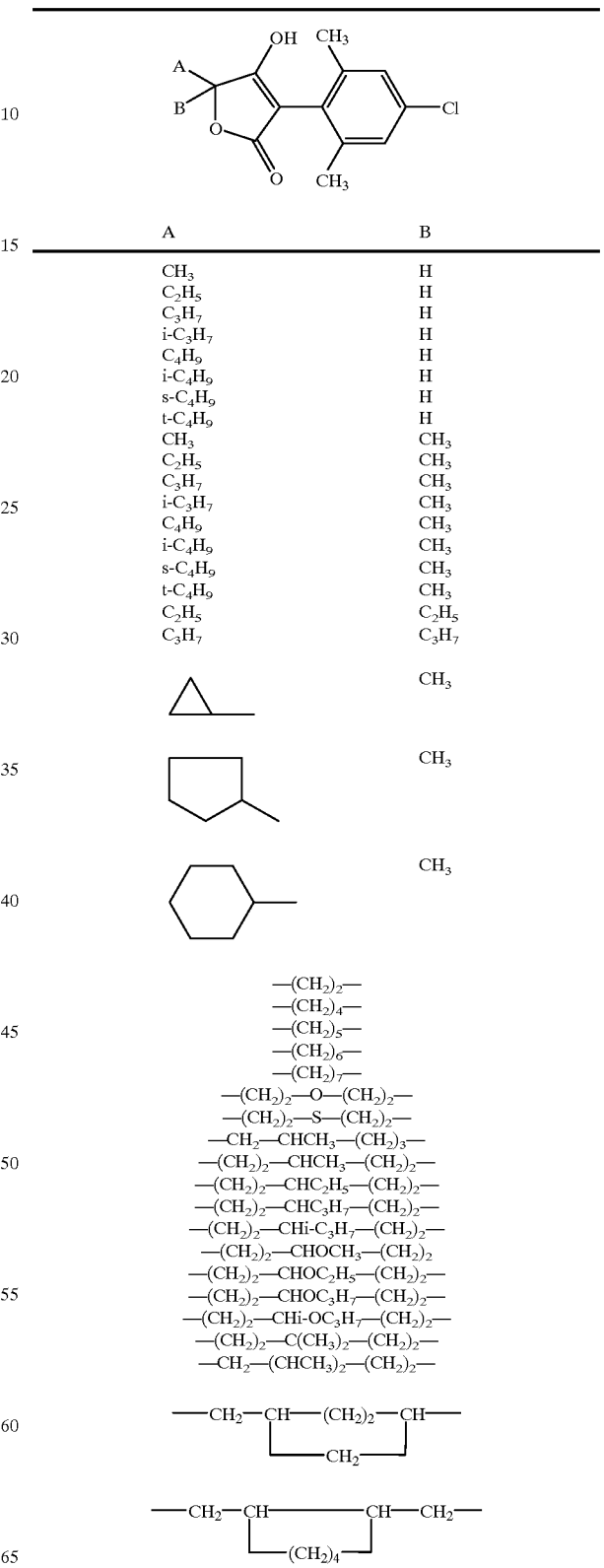

| A | B |
|---|---|
| CH$_3$ | H |
| C$_2$H$_5$ | H |
| C$_3$H$_7$ | H |
| i-C$_3$H$_7$ | H |
| C$_4$H$_9$ | H |
| i-C$_4$H$_9$ | H |
| s-C$_4$H$_9$ | H |
| t-C$_4$H$_9$ | H |
| CH$_3$ | CH$_3$ |
| C$_2$H$_5$ | CH$_3$ |
| C$_3$H$_7$ | CH$_3$ |
| i-C$_3$H$_7$ | CH$_3$ |
| C$_4$H$_9$ | CH$_3$ |
| i-C$_4$H$_9$ | CH$_3$ |
| s-C$_4$H$_9$ | CH$_3$ |
| t-C$_4$H$_9$ | CH$_3$ |
| C$_2$H$_5$ | C$_2$H$_5$ |
| C$_3$H$_7$ | C$_3$H$_7$ |
| cyclopropyl | CH$_3$ |
| cyclopentyl | CH$_3$ |
| cyclohexyl | CH$_3$ |
| —(CH$_2$)$_2$— | |
| —(CH$_2$)$_4$— | |
| —(CH$_2$)$_5$— | |
| —(CH$_2$)$_6$— | |
| —(CH$_2$)$_7$— | |
| —(CH$_2$)$_2$—O—(CH$_2$)$_2$— | |
| —(CH$_2$)$_2$—S—(CH$_2$)$_2$— | |
| —CH$_2$—CHCH$_3$—(CH$_2$)$_3$— | |
| —(CH$_2$)$_2$—CHCH$_3$—(CH$_2$)$_2$— | |
| —(CH$_2$)$_2$—CHC$_2$H$_5$—(CH$_2$)$_2$— | |
| —(CH$_2$)$_2$—CHC$_3$H$_7$—(CH$_2$)$_2$— | |
| —(CH$_2$)$_2$—CHi-C$_3$H$_7$—(CH$_2$)$_2$— | |
| —(CH$_2$)$_2$—CHOCH$_3$—(CH$_2$)$_2$— | |
| —(CH$_2$)$_2$—CHOC$_2$H$_5$—(CH$_2$)$_2$— | |
| —(CH$_2$)$_2$—CHOC$_3$H$_7$—(CH$_2$)$_2$— | |
| —(CH$_2$)$_2$—CHi-OC$_3$H$_7$—(CH$_2$)$_2$— | |
| —(CH$_2$)$_2$—C(CH$_3$)$_2$—(CH$_2$)$_2$— | |
| —CH$_2$—(CHCH$_3$)$_2$—(CH$_2$)$_2$— | |
| —CH$_2$—CH—(CH$_2$)$_2$—CH—CH$_2$— | |
| —CH$_2$—CH—(CH$_2$)$_4$—CH—CH$_2$— | |

TABLE 5-continued

[Structure: furanone with OH, A, B substituents on ring carbon, attached to 2,6-dimethyl-4-chlorophenyl]

| A | B |
|---|---|
| —CH₂—CH(—(CH₂)₃—)CH—(CH₂)₂— | |
| (indane ring) | |
| (tetrahydronaphthalene ring) | |

| A | B |
|---|---|
| $-CH_2-CH\langle(CH_2)_3\rangle CH-(CH_2)_2-$ | |
| indan-1,2-diyl | |
| tetrahydronaphthalen-1,2-diyl | |

TABLE 6

[Structure: furanone with OH, A, B substituents, attached to 2-chloro-4,6-dimethylphenyl]

| A | B |
|---|---|
| $CH_3$ | H |
| $C_2H_5$ | H |
| $C_3H_7$ | H |
| $i-C_3H_7$ | H |
| $C_4H_9$ | H |
| $i-C_4H_9$ | H |
| $s-C_4H_9$ | H |
| $t-C_4H_9$ | H |
| $CH_3$ | $CH_3$ |
| $C_2H_5$ | $CH_3$ |
| $C_3H_7$ | $CH_3$ |
| $i-C_3H_7$ | $CH_3$ |
| $C_4H_9$ | $CH_3$ |
| $i-C_4H_9$ | $CH_3$ |
| $s-C_4H_9$ | $CH_3$ |
| $t-C_4H_9$ | $CH_3$ |
| $C_2H_5$ | $C_2H_5$ |
| $C_3H_7$ | $C_3H_7$ |
| cyclopropyl | $CH_3$ |
| cyclopentyl | $CH_3$ |
| cyclohexyl | $CH_3$ |
| $-(CH_2)_2-$ | |
| $-(CH_2)_4-$ | |

TABLE 6-continued

[Structure: furanone with OH, A, B substituents, attached to 2-chloro-4,6-dimethylphenyl]

| A | B |
|---|---|
| $-(CH_2)_5-$ | |
| $-(CH_2)_6-$ | |
| $-(CH_2)_7-$ | |
| $-(CH_2)_2-O-(CH_2)_2-$ | |
| $-(CH_2)_2-S-(CH_2)_2-$ | |
| $-CH_2-CHCH_3-(CH_2)_3-$ | |
| $-(CH_2)_2-CHCH_3-(CH_2)_2-$ | |
| $-(CH_2)_2-CHC_2H_5-(CH_2)_2-$ | |
| $-(CH_2)_2-CHC_3H_7-(CH_2)_2-$ | |
| $-(CH_2)_2-CHi-C_3H_7-(CH_2)_2-$ | |
| $-(CH_2)_2-CHOCH_3-(CH_2)_2-$ | |
| $-(CH_2)_2-CHOC_2H_5-(CH_2)_2-$ | |
| $-(CH_2)_2-CHOC_3H_7-(CH_2)_2-$ | |
| $-(CH_2)_2-CHi-OC_3H_7-(CH_2)_2-$ | |
| $-(CH_2)_2-C(CH_3)_2-(CH_2)_2-$ | |
| $-CH_2-(CHCH_3)_2-(CH_2)_2-$ | |
| $-CH_2-CH\langle-CH_2-\rangle-(CH_2)_2-CH-$ | |
| $-CH_2-CH\langle(CH_2)_4\rangle CH-CH_2-$ | |
| $-CH_2-CH\langle(CH_2)_3\rangle CH-(CH_2)_2-$ | |
| indan-1,2-diyl | |
| tetrahydronaphthalen-1,2-diyl | |

TABLE 7

[Structure: furanone with OH, A, B substituents, attached to 2-chloro-4-bromo-6-methylphenyl]

| A | B |
|---|---|
| $CH_3$ | H |
| $C_2H_5$ | H |
| $C_3H_7$ | H |
| $i-C_3H_7$ | H |
| $C_4H_9$ | H |
| $i-C_4H_9$ | H |
| $s-C_4H_9$ | H |
| $t-C_4H_9$ | H |
| $CH_3$ | $CH_3$ |

TABLE 7-continued

[Structure: furanone with OH, CH3, Br, Cl substituents, positions A and B]

| A | B |
|---|---|
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |
| C₂H₅ | C₂H₅ |
| C₃H₇ | C₃H₇ |
| cyclopropyl | CH₃ |
| cyclopentyl | CH₃ |
| cyclohexyl | CH₃ |
| —(CH₂)₂— | |
| —(CH₂)₄— | |
| —(CH₂)₅— | |
| —(CH₂)₆— | |
| —(CH₂)₇— | |
| —(CH₂)₂—O—(CH₂)₂— | |
| —(CH₂)₂—S—(CH₂)₂— | |
| —CH₂—CHCH₃—(CH₂)₃— | |
| —(CH₂)₂—CHCH₃—(CH₂)₂— | |
| —(CH₂)₂—CHC₂H₅—(CH₂)₂— | |
| —(CH₂)₂—CHC₃H₇—(CH₂)₂— | |
| —(CH₂)₂—CHi-C₃H₇—(CH₂)₂— | |
| —(CH₂)₂—CHOCH₃—(CH₂)₂— | |
| —(CH₂)₂—CHOC₂H₅—(CH₂)₂— | |
| —(CH₂)₂—CHOC₃H₇—(CH₂)₂— | |
| —(CH₂)₂—CHi-OC₃H₇—(CH₂)₂— | |
| —(CH₂)₂—C(CH₃)₂—(CH₂)₂— | |
| —CH₂—(CHCH₃)₂—(CH₂)₂— | |
| —CH₂—CH—(CH₂)₂—CH— with —CH₂— bridge | |
| —CH₂—CH—CH—CH₂— with —(CH₂)₄— bridge | |
| —CH₂—CH—CH—(CH₂)₂— with —(CH₂)₃— bridge | |
| indanyl | |

TABLE 7-continued

[Structure: furanone with OH, CH3, Br, Cl substituents, positions A and B]

| A | B |
|---|---|
| tetrahydronaphthyl (fused) | |

TABLE 8

[Structure: furanone with OH, Br, CH3, CH3 substituents, positions A and B]

| A | B |
|---|---|
| CH₃ | H |
| C₂H₅ | H |
| C₃H₇ | H |
| i-C₃H₇ | H |
| C₄H₉ | H |
| i-C₄H₉ | H |
| s-C₄H₉ | H |
| t-C₄H₉ | H |
| CH₃ | CH₃ |
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |
| C₂H₅ | C₂H₅ |
| C₃H₇ | C₃H₇ |
| cyclopropyl | CH₃ |
| cyclopentyl | CH₃ |
| cyclohexyl | CH₃ |
| —(CH₂)₂— | |
| —(CH₂)₄— | |
| —(CH₂)₅— | |
| —(CH₂)₆— | |
| —(CH₂)₇— | |
| —(CH₂)₂—O—(CH₂)₂— | |
| —(CH₂)₂—S—(CH₂)₂— | |
| —CH₂—CHCH₃—(CH₂)₃— | |
| —(CH₂)₂—CHCH₃—(CH₂)₂— | |
| —(CH₂)₂—CHC₂H₅—(CH₂)₂— | |
| —(CH₂)₂—CHC₃H₇—(CH₂)₂— | |
| —(CH₂)₂—CHi-C₃H₇—(CH₂)₂— | |

TABLE 8-continued

[Structure: furanone with OH, Br, CH3 substituents on phenyl ring; positions A, B on furanone ring]

| A | B |
|---|---|
| —(CH₂)₂—CHOCH₃—(CH₂)₂— | |
| —(CH₂)₂—CHOC₂H₅—(CH₂)₂— | |
| —(CH₂)₂—CHOC₃H₇—(CH₂)₂— | |
| —(CH₂)₂—CHi-OC₃H₇—(CH₂)₂— | |
| —(CH₂)₂—C(CH₃)₂—(CH₂)₂— | |
| —CH₂—(CHCH₃)₂—(CH₂)₂— | |
| —CH₂—CH—(CH₂)₂—CH— with —CH₂— bridge | |
| —CH₂—CH——CH—CH₂— with —(CH₂)₄— bridge | |
| —CH₂—CH——CH—(CH₂)₂— with —(CH₂)₃— bridge | |
| indane group | |
| tetrahydronaphthalene group | |

In addition to the compounds mentioned in the Preparation Examples, the following compounds of the formula (I-3-a) may specifically be mentioned:

TABLE 9

[Structure: thiophenone with OH, Cl, CH3 substituents on phenyl ring; positions A, B]

| A | B |
|---|---|
| CH₃ | H |
| C₂H₅ | H |
| C₃H₇ | H |
| i-C₃H₇ | H |
| C₄H₉ | H |
| i-C₄H₉ | H |
| s-C₄H₉ | H |
| t-C₄H₉ | H |
| CH₃ | CH₃ |
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |

TABLE 9-continued

[Structure: thiophenone with OH, Cl, CH3 substituents on phenyl ring; positions A, B]

| A | B |
|---|---|
| t-C₄H₉ | CH₃ |
| C₂H₅ | C₂H₅ |
| C₃H₇ | C₃H₇ |
| cyclopropyl | CH₃ |
| cyclopentyl | CH₃ |
| cyclohexyl | CH₃ |
| —(CH₂)₂— | |
| —(CH₂)₄— | |
| —(CH₂)₅— | |
| —(CH₂)₆— | |
| —(CH₂)₇— | |
| —(CH₂)₂—O—(CH₂)₂— | |
| —(CH₂)₂—S—(CH₂)₂— | |
| —CH₂—CHCH₃—(CH₂)₃— | |
| —(CH₂)₂—CHCH₃—(CH₂)₂— | |
| —(CH₂)₂—CHC₂H₅—(CH₂)₂— | |
| —(CH₂)₂—CHC₃H₇—(CH₂)₂— | |
| —(CH₂)₂—CHi-C₃H₇—(CH₂)₂— | |
| —(CH₂)₂—CHOCH₃—(CH₂)₂— | |
| —(CH₂)₂—CHOC₂H₅—(CH₂)₂— | |
| —(CH₂)₂—CHOC₃H₇—(CH₂)₂— | |
| —(CH₂)₂—CHi-OC₃H₇—(CH₂)₂— | |
| —(CH₂)₂—C(CH₃)₂—(CH₂)₂— | |
| —CH₂—(CHCH₃)₂—(CH₂)₂— | |
| —CH₂—CH—(CH₂)₂—CH— with —CH₂— bridge | |
| —CH₂—CH——CH—CH₂— with —(CH₂)₄— bridge | |
| —CH₂—CH——CH—(CH₂)₂— with —(CH₂)₃— bridge | |
| indane group | |
| tetrahydronaphthalene group | |

Table 10:
A, B as indicated in Table 9
X=CH₃; Y=Cl; Z=CH₃

Table 11:

A, B as indicated in Table 9

X=CH₃; Y=CH₃; Z=Br

Table 12:

A, B as indicated in Table 9

X=CH₃; Y=Br; Z=CH₃

In addition to the compounds mentioned in the Preparation Examples, the following compounds of the formula (I-5-a) may specifically be mentioned:

TABLE 13

[Structure: pyranone ring with A, OH, substituents, D, fused with chlorophenyl bearing CH₃ groups]

| A | D |
|---|---|
| H | CH₃ |
| H | C(CH₃)₃ |
| H | C(CH₃)₂CH₂Cl |
| CH₃ | CH₃ |
| CH₃ | CH₂CHCH₃CH₂CH₃ |
| H | CH=C(CH₃)₂ |
| CH₃ | 4-F-C₆H₄ |
| CH₃ | 4-Cl-C₆H₄ |
| CH₃ | 2,4-F₂-C₆H₃ |
| CH₃ | 3,4-Cl₂-C₆H₃ |
| CH₃ | 4-OCF₃-C₆H₄ |
| CH₃ | C₆H₅ |
| H | 2-furyl |
| CH₃ | 2-thienyl |

TABLE 13-continued

[Structure as above]

| A | D |
|---|---|
| CH₃ | 2-pyridyl |
| CH₃ | 2-pyridyl |
| CH₃ | 4-pyridyl |
| H | 2,4,5-trimethylthiazolyl |
| CH₃ | C₅H₉ |
| CH₃ | C₃H₅ |
| H | C₃H₄Cl |
| (CH₂)₃ | |
| (CH₂)₄ | |
| C(CH₃)₂OC(CH₃)₂ | |

Table 14:

A and D as indicated in Table 13

X=CH₃; Y=Cl; Z=CH₃

Table 15:

A and D as indicated in Table 13

X=CH₃; Y=CH₃; Z=Br

Table 16:

A and D as indicated in Table 13

X=CH₃; Y=Br; Z=CH₃

In addition to the compounds mentioned in the Preparation Examples, the following compounds of the formula (I-6-a) may specifically be mentioned:

TABLE 17

[Structure: thiazine ring with A, OH, =O, linked to chlorophenyl with CH₃ groups]

| A |
|---|
| CH₃ |
| CH(CH₃)₂ |

TABLE 17-continued

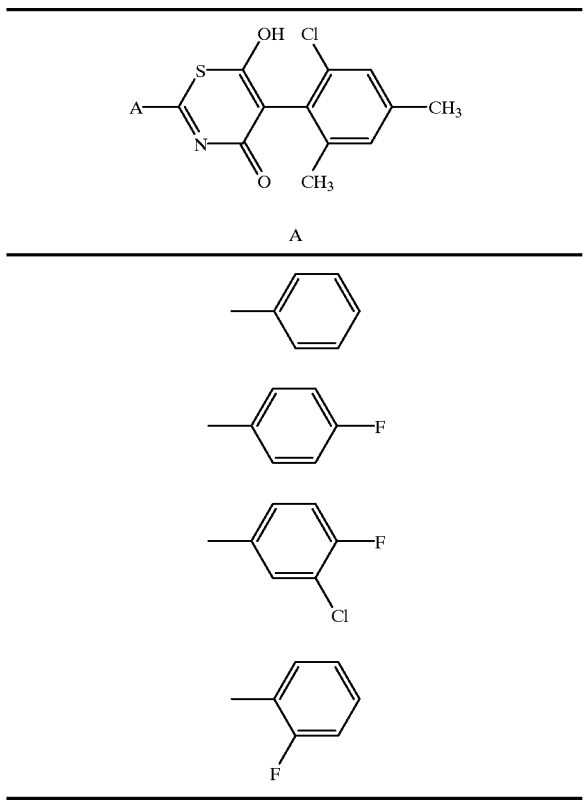

Table 18:
  A and D as indicated in Table 17
  X=CH₃; Y=Cl; Z=CH₃
Table 19:
  A as indicated in Table 17
  X=CH₃; Y=CH₃; Z=Br
Table 20:
  A as indicated in Table 17
  X=CH₃; Y=Br; Z=CH₃

If according to process (A) ethyl N-[(2-chloro-4,6-dimethyl)-phenylacetyl]-1-amino-4-ethyl-cyclohexane-carboxylate is used as a starting substance, the course of the process according to the invention can be represented by the following equation:

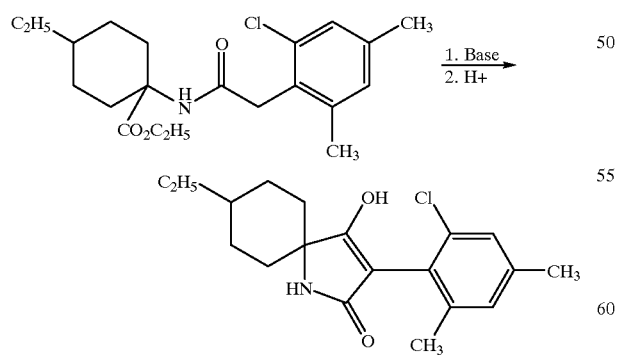

If according to process (B) ethyl O-[(2-chloro-4,6-dimethyl)phenylacetyl]hydroxyacetate is used, the course of the process according to the invention can be represented by the following equation:

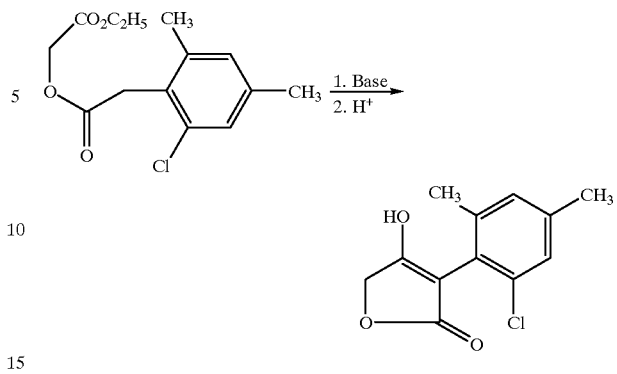

If according to process (C) ethyl 2-[(2-bromo-4,6-dimethyl)-phenyl]-4-(4-methoxy)benzylmercapto-4-methyl-3-oxo-valerate is used, the course of the process according to the invention can be represented by the following equation:

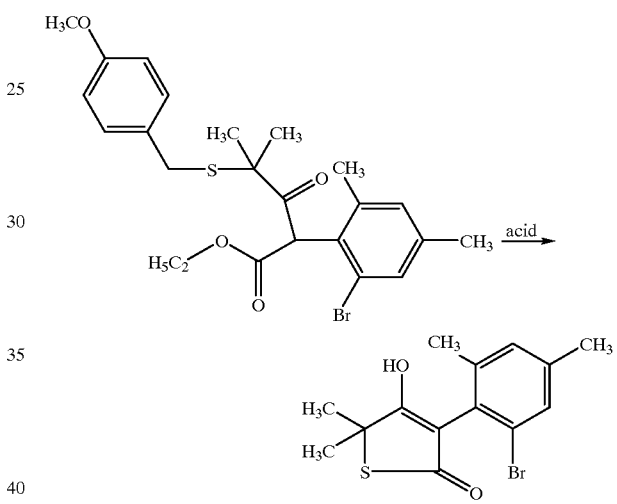

If, for example, according to process (E) chlorocarbonyl 2-[(2-bromo-4,6-dimethyl)phenyl ketene and acetone are used as starting compounds, the course of the process according to the invention can be represented by the following equation:

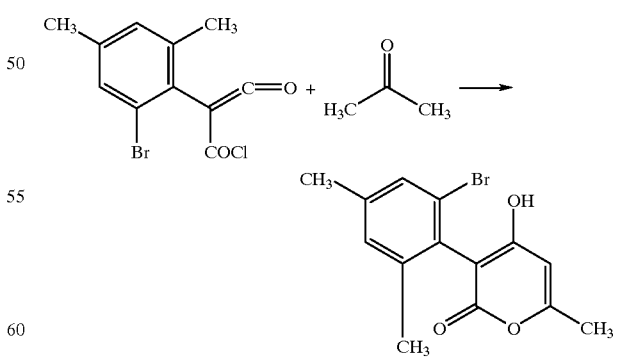

If, for example, according to process (F) chlorocarbonyl 2-(4-bromo-2,6-dimethyl)phenyl ketene and thiobenzamide are used as starting compounds, the course of the process according to the invention can be represented by the following equation:

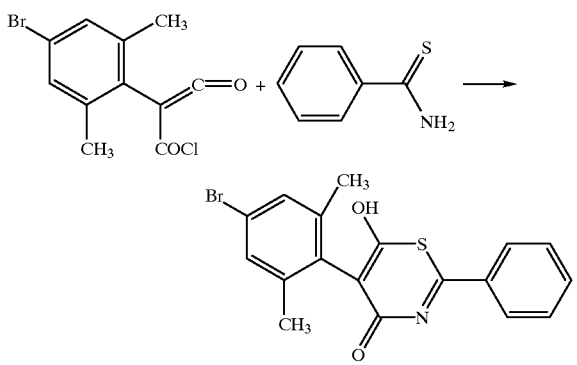

If, according to process (Gα) 3-[(2-chloro-4,6-dimethyl)-phenyl]-5,5-dimethylpyrrolidine-2,4-dione and pivaloyl chloride are used as starting substances, the course of the process according to the invention can be represented by the following equation:

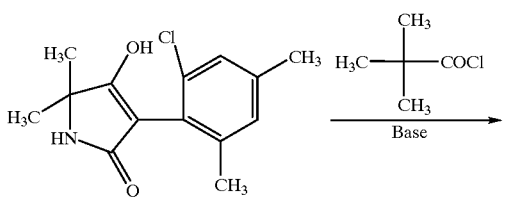

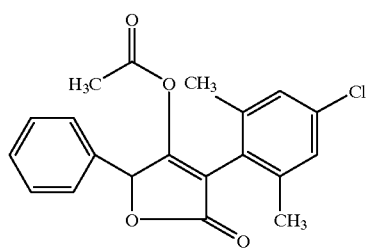

If according to process (G) (variant β) 3-[(4-chloro-2,6-dimethyl)-phenyl]-4-hydroxy-5-phenyl-Δ³-dihydrofuran-2-one and acetic anhydride are used as starting compounds, the course of the process according to the invention can be represented by the following equation

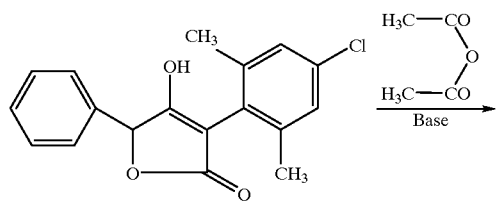

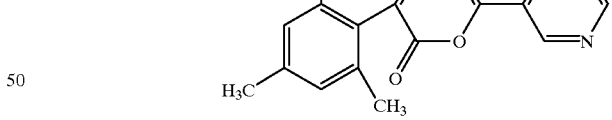

If according to process (H) 8-[(4-bromo-2-ethyl-6-methyl)-phenyl]-1,6-diaza-bicyclo-(4,3,0$^{1.6}$)-nonane-7,9-dione and ethoxyethyl chloroformate are used as starting compounds, the course of the process according to the invention can be represented by the following equation:

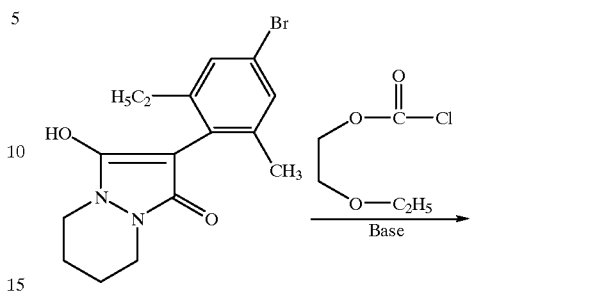

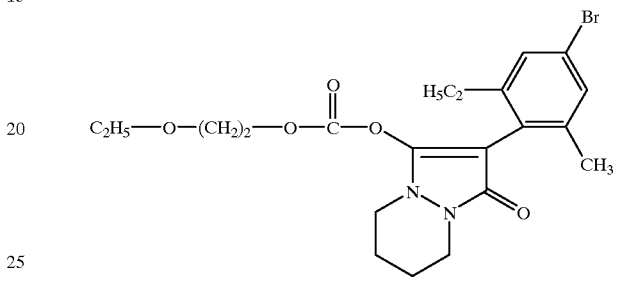

If according to process (I), (variant α), 3-[(2-chloro-4,6-dimethyl)-phenyl]-4-hydroxy-6-(3-pyridyl)-pyrone and methyl chloromonothioformate are used as starting materials, the course of the reaction can be represented in the following manner:

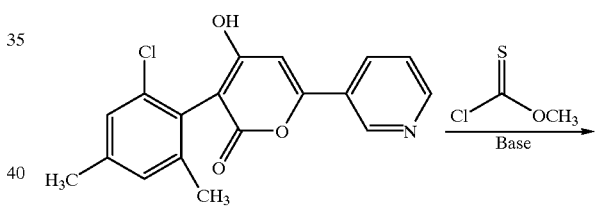

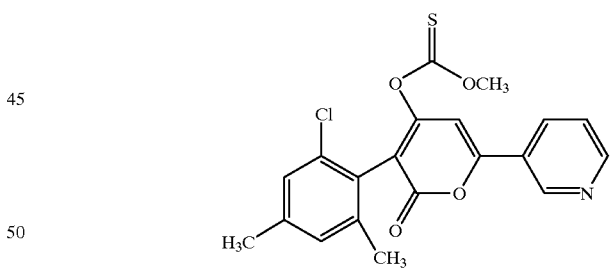

If according to process (I), (variant β), 5-[(2-bromo-4-methyl-6-methyl)-phenyl]-6-hydroxy-2-(4-chlorophenyl)-thiazin-4-one, carbon disulphide and methyl iodide are used as starting components, the course of the reaction can be represented as follows:

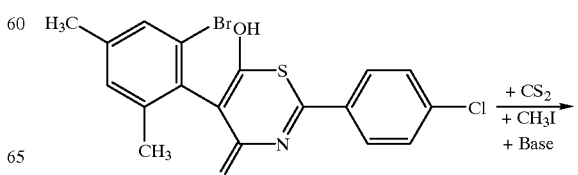

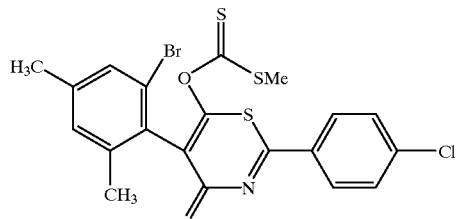

If according to process (J) 2-[(2-chloro-4,6-dimethyl)-phenyl]-1,5-trimethylenepyrrolidine-2,4-dione and methanesulphonyl chloride are used as starting materials, the course of the reaction can be represented by the following equation:

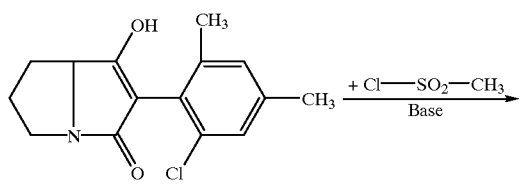

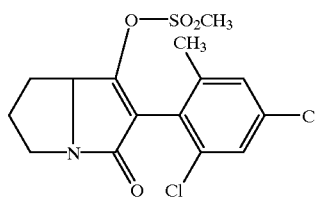

If according to process (K) 2[(2-chloro-6-ethyl-4-methyl)-phenyl]-4-hydroxy-5-methyl-6-(2-pyridyl)-pyrone and 2,2,2-trifluoroethyl chloromethanethio-phosphonate are used as starting materials, the course of the reaction can be represented by the following equation:

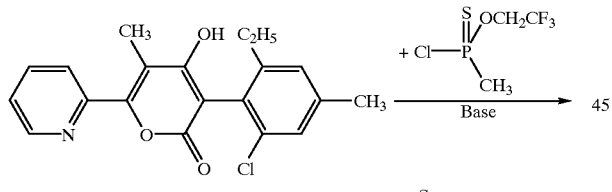

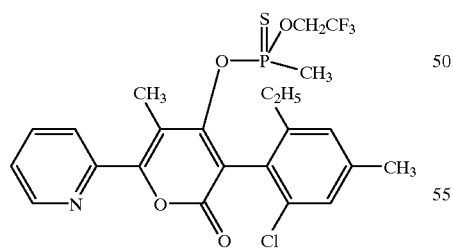

If according to process (L) 3-[(4-bromo-2,6-diethyl)-phenyl]-5-cyclopropyl-5-methylpyrrolidine-2,4-dione and NaOH are used as components, the course of the process according to the invention can be represented by the following equation:

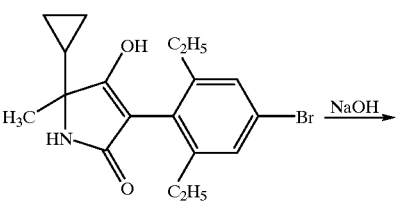

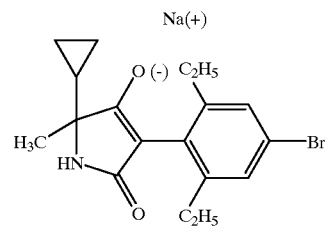

If according to process (M) (variant α) 3-[(2-bromo-4,6-dimethyl)-phenyl]-4-hydroxy-5,5-tetramethylene-Δ³-dihydrofuran-2-one and ethyl isocyanate are used as starting materials, the course of the reaction can be represented by the following equation:

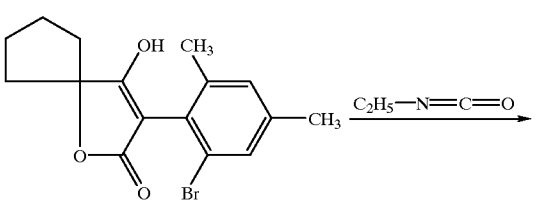

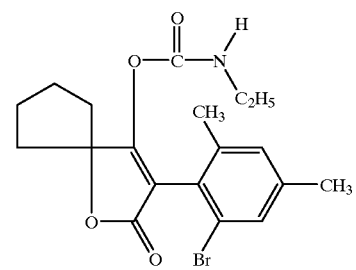

If according to process (M) (variant β) 3-[(2-chloro-4,6-dimethyl)-phenyl]-5-methylpyrrolidine-2,4-dione and dimethylcarbamoyl chloride are used as starting materials, the course of the reaction can be represented by the following equation:

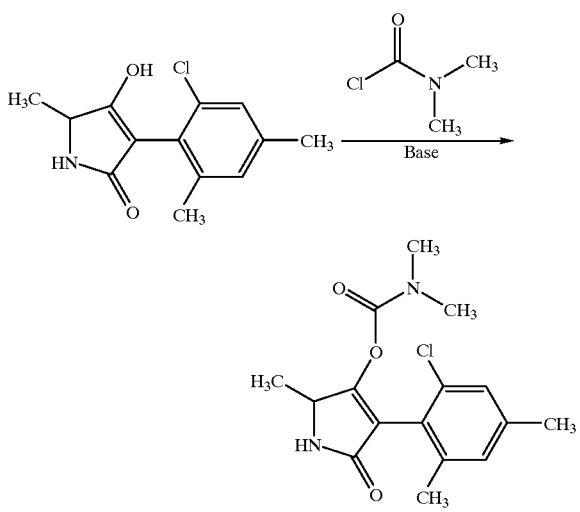

The compounds of the formula (II)

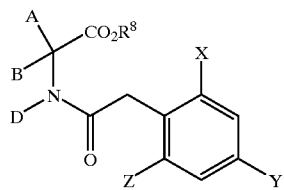
(II)

in which
A, B, D, X, Y, Z and $R^8$ have the meanings given above,
needed as starting substances in process (A) according to the invention are new.

The acylamino acid esters of the formula (II) are obtained, for example, when amino acid derivatives of the formula (XXI)

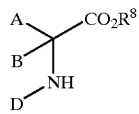
(XXI)

in which
A, B, $R^8$ and D have the meanings given above,
are acylated using substituted phenylacetyl halides of the formula (XXII)

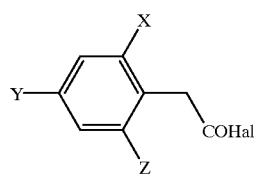
(XXII)

in which
X, Y and Z have the meanings given above and
Hal represents chlorine or bromine, (Chem. Reviews 52, 237–416 (1953); Bhattacharya, Indian J. Chem. 6, 341–5, 1968)
or when acylamino acids of the formula (XXIII)

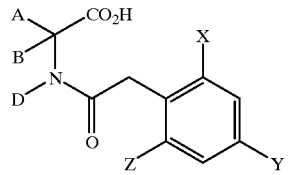
(XXIII)

in which
A, B, D, X, Y and Z have the meanings given above,
are esterified (Chem. Ind. (London) 1568 (1968)).

The compounds of the formula (XXIII)

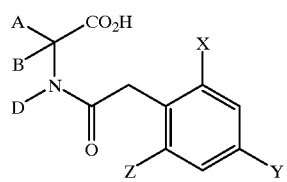
(XXIII)

in which
A, B, D, X, Y and Z have the meanings given above,
are new.

The compounds of the formula (XXIII) are obtained when amino acids of the formula (XXIV)

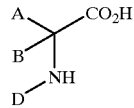
(XXIV)

in which
A, B and D have the meanings given above,
are acylated using substituted phenylacetyl halides of the formula (XXII)

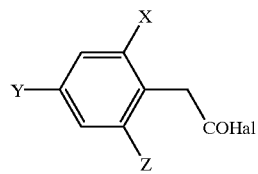
(XXII)

in which
X, Y and Z have the meanings given above and
Hal represents chlorine or bromine,
according to Schotten-Baumann (Organikum, VEB Deutscher Verlag der Wissenschaften, Berlin 1977, p. 505).
The compounds of the formula (XXII) are new.
The compounds of the formula (XXII) are obtained, for example, by reacting substituted phenylacetic acids of the formula (XXV)

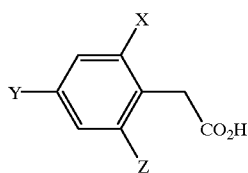

(XXV)

in which
X, Y and Z have the meanings given above,
with halogenating agents (e.g. thionyl chloride, thionyl bromide, oxalyl chloride, phosgene, phosphorus trichloride, phosphorus tribromide or phosphorus pentachloride), if appropriate in the presence of a diluent (e.g. optionally chlorinated aliphatic or aromatic hydrocarbons such as toluene or methylene chloride) at temperatures from −20° C. to 150° C., preferably from −10° C. to 100° C.

The compounds of the formula (XXV) are new.

The compounds of the formula (XXV) are obtained, for example, by hydrolysing substituted phenylacetic acid esters of the formula (XXVI)

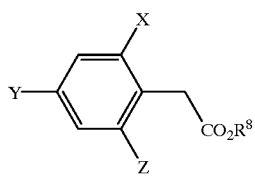

(XXVI)

in which
X, Y, Z and $R^8$ have the meaning give above,
at temperatures between 0° C. and 150° C., preferably between 20° C. and 100° C., in the presence of an acid (e.g. of an inorganic acid such as hydrochloric acid) or of a base (e.g. of an alkali metal hydroxide such as sodium or potassium hydroxide) and, if appropriate, of a diluent (e.g. of an aqueous alcohol such as methanol or ethanol).

The compounds of the formula (XXVI) are new.

The compounds of the formula (XXVI) are obtained, for example, by reacting substituted 1,1,1-trichloro-2-phenylethanes of the formula (XXVII)

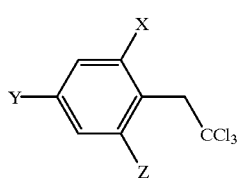

(XXVII)

in which
X, Y and Z have the meanings given above,
first with alkoxides (e.g. alkali metal alkoxides such as sodium methoxide or sodium ethoxide) in the presence of a diluent (e.g. the alcohol derived from the alkoxide) at temperatures between 0° C. and 150° C., preferably between 20° C. and 120° C., and then reacting with an acid (preferably an inorganic acid, e.g. sulphuric acid) at temperatures between −20° C. and 150° C., preferably 0° C. and 100° C. (cf. DE-3314249).

The compounds of the formula (XXVII) are new.

The compounds of the formula (XXVII) are obtained, for example, when anilines of the formula (XXVIII)

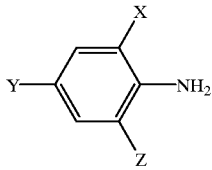

(XXVIII)

in which
X, Y and Z have the meaning given above,
are reacted with vinylidene chloride ($CH_2$=$CCl_2$) in the presence of an alkyl nitrite of the formula (XXIX)

$R^{21}$—ONO  (XXIX)

in which
$R^{21}$ represents alkyl, preferably $C_1$–$C_6$-alkyl,
in the presence of copper(II) chloride and if appropriate in the presence of a diluent (e.g. of an aliphatic nitrile such as acetonitrile) at a temperature of −20° C. to 80° C., preferably 0° C. to 60° C. (cf. J. Org. Chem. 53 (1988), 3637).

The compounds of the formulae (XXVIII) and (XXX) are known compounds of organic chemistry. Copper(II) chloride and vinylidene chloride are long-known and commercially available.

The compounds of the formulae (XXI) and (XXIV) are known in some cases and/or can be prepared by known processes (see, for example, Compagnon, Miocque Ann. Chim. (Paris) [14] 5, p. 11–22, 23–27 (1970)).

The substituted cyclic aminocarboxylic acids of the formula (XXIVa), in which A and B form a ring, are in general obtainable by the Bucherer-Bergs synthesis or by the Strecker synthesis and are in each case obtained here in different isomeric forms. Thus, according to the conditions of the Bucherer-Bergs synthesis mainly the isomers (in the following designated as β for the sake of simplicity) in which the radicals R and the carboxyl group are equatorial are obtained, while according to the conditions of the Strecker synthesis mainly the isomers (in the following designated as α for the sake of simplicity) are obtained in which the amino group and the radicals R are equatorial.

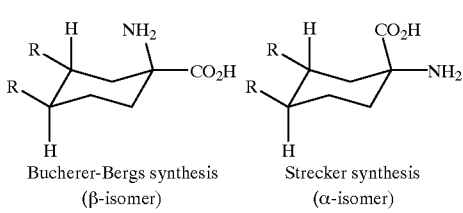

Bucherer-Bergs synthesis (β-isomer)    Strecker synthesis (α-isomer)

(L. Munday, J. Chem. Soc. 4372 (1961); J. T. Eward, C. Jitrangeri, Can. J. Chem. 53, 3339 (1975)).

Furthermore, the starting substances of the formula (II)

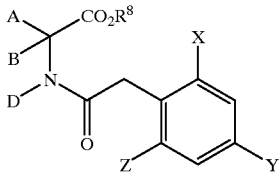
(II)

in which

A, B, D, X, Y, Z and $R^8$ have the meanings given above, used in the above process (A) can be prepared when aminonitriles of the formula (XXX)

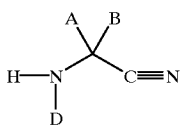
(XXX)

in which

A, B and D have the meanings given above, are reacted with substituted phenylacetyl halides of the formula (XXII)

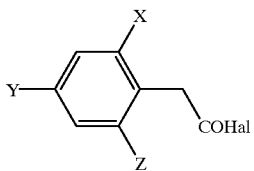
(XXII)

in which

X, Y, Z and Hal have the meanings given above, to give compound s of the formula (XXXI)

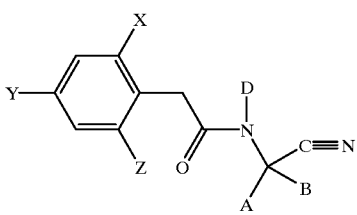
(XXXI)

in which

A, B, D, X, Y and Z have the meanings given above, and these are then subjected to an acidic alcoholysis.
The compounds of the formula (XXXI) are also new.

The compounds of the formula (III)

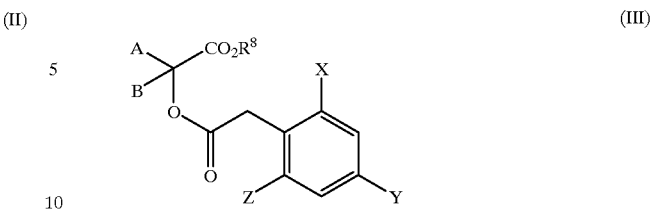
(III)

in which

A, B, X, Y, Z and $R^8$ have the meanings given above, needed as starting substances in process (B) according to the invention are new.

They can be prepared in a simple manner by methods known in principle.

The compounds of the formula (III) are obtained, for example, when 2-hydroxycarboxylic acid esters of the formula (XXXII)

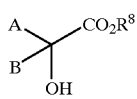
(XXXII)

in which

A, B and $R^8$ have the meanings given above, are acylated using substituted phenylacetyl halides of the formula (XXII)

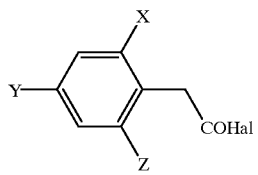
(XXII)

in which

X, Y, Z and Hal have the meanings given above,
(Chem. Reviews 52, 237–416 (1953)).

Furthermore, compounds of the formula (III) are obtained when substituted phenylacetic acids of the formula (XXV)

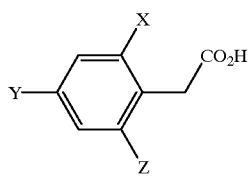
(XXV)

in which

X, Y and Z have the meanings given above, are alkylated using α-halogenocarboxylic acid esters of the formula (XXXIII)

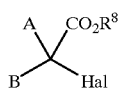
(XXXIII)

in which
A, B and $R^8$ have the meanings given above and
Hal represents chlorine or bromine.
The compounds of the formula (XXXIII) are commercially available.
The compounds of the formula (IV)

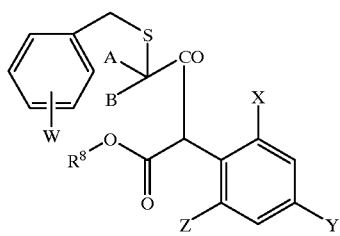
(IV)

in which
A, B, W, X, Y, Z and $R^8$ have the meanings given above,
needed as starting substances in the above process (C) are new.
They can be prepared by methods known in principle.
The compounds of the formula (IV) are obtained, for example, when substituted phenylacetic acid esters of the formula (XXVI)

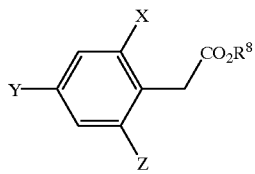
(XXVI)

in which
X, Y, $R^8$ and Z have the meanings given above,
are acylated using 2-benzylthio-carbonyl halides of the formula (XXXIV)

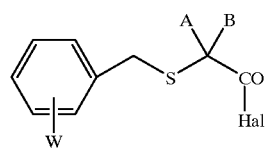
(XXXIV)

in which
A, B and W have the meanings given above and
Hal represents halogen (in particular chlorine or bromine),
in the presence of strong bases (see, for example, M. S. Chambers, E. J. Thomas, D. J. Williams, J. Chem. Soc. Chem. Commun., (1987), 1228).
The benzylthio-carbonyl halides of the formula (XXXIV) are known in some cases and/or can be prepared by known methods (J. Antibiotics (1983), 26, 1589).

The halogenocarbonylketenes of the formula (V) needed as starting substances in process (E) are new. They can be prepared in a simple manner by methods known in principle (cf., for example, Org. Prep. Proced. Int., 7, (4), 155–158, 1975 and DE 1945703). The compounds of the formula (V)

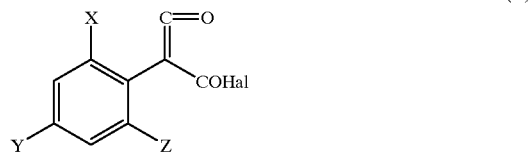
(V)

in which
X, Y and Z have the meanings given above and
Hal represents chlorine or bromine,
are obtained when
substituted phenylmalonic acids of the formula (XXXV)

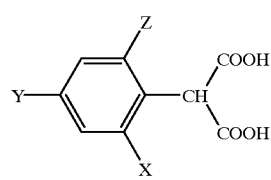
(XXXV)

in which
X, Y and Z have the meanings given above,
are reacted with acid halides, for example thionyl chloride, phosphorus(V) chloride, phosphorus(III) chloride, oxalyl chloride, phosgene or thionyl bromide, if appropriate in the presence of catalysts, for example diethylformamide, methylsterylformamide or triphenylphosphine and if appropriate in the presence of bases, e.g. pyridine or triethylamine, at a temperature between −20° C. and 200° C., preferably between 0° C. and 150° C.
The substituted phenylmalonic acids of the formula (XXXV) are new. However, they can be prepared by known processes in a simple manner (cf., for example Organikum, VEB Deutscher Verlag der Wissenschaften, Berlin 1977, p. 517 ff).
The carbonyl compounds of the formula (VIII) or their silyl enol ethers of the formula (VIIIa)

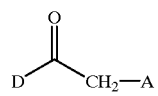
(VIII)

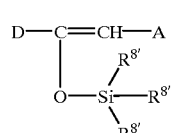
(VIIIa)

in which
A, D and $R^{8'}$ have the meanings given above,
needed as starting substances for process (E) according to the invention are compounds which are commercially available, generally known or accessible by known processes.

The preparation of the ketene acid chlorides of the formula (V) needed as starting substances for carrying out process (F) according to the invention has already been described in process (E) according to the invention. The thioamides of the formula (IX)

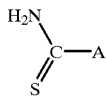

(IX)

in which
A has the meaning given above,
needed for carrying out process (F) according to the invention are compounds which are generally known in organic chemistry.

The compounds of the formula (I-4-a) needed as starting substances in process (G) are known and/or can be prepared in a simple manner by known methods (cf. WO 92/16510).

The compounds of the formula (I-4-a) are obtained, for example, when compounds of the formula (V)

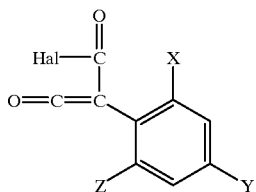

(V)

in which
X, Y and Z have the meanings given above
and
Hal represents halogen (in particular chlorine or bromine),
or
compounds of the formula (VI)

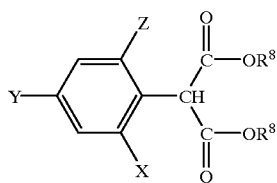

(VI)

in which
$R^8$, X, Y and Z have the meanings given above,
are reacted with hydrazines of the formula (VII)

A—NH—NH—D (VII)

in which
A and D have the meanings given above,
if appropriate in the presence of a diluent,
it being possible to use hydrocarbons, such as toluene and xylene, further ethers, such as dibutyl ether, tetrahydrofuran, dioxane, glycol dimethyl ether and diglycol dimethyl ether, additionally polar solvents, such as dimethyl sulphoxide, sulpholane, dimethylformamide and N-methyl-pyrrolidone, and, only in the case in which compounds of the formula (VI) are employed, alcohols such as methanol, ethanol, propanol, iso-propanol, butanol, iso-butanol and tert-butanol, and if appropriate in the presence of a base, where in the case in which compounds of the formula (V) are employed, inorganic bases, in particular alkali metal or alkaline earth metal carbonates such as sodium carbonate, potassium carbonate or calcium carbonate, and organic bases, for example pyridine or triethylamine, are suitable and in the case where compounds of the formula (VI) are employed, alkali metal and alkaline earth metal oxides, hydroxides and carbonates, such as sodium hydroxide, potassium hydroxide, magnesium oxide, calcium oxide, sodium carbonate, potassium carbonate and calcium carbonate, each of which can also be employed in the presence of phase-transfer catalysts, e.g. triethylbenzylammonium chloride, tetrabutylammonium bromide, Adogen 464 (=methyltrialkyl($C_8$–$C_{10}$)ammonium chloride) or TDA 1 (=tris-(methoxyethoxyethyl)-amine), alkali metals such as sodium or potassium, alkali metal and alkaline earth metal amides and hydrides, such as sodium amide, sodium hydride and calcium hydride, and additionally also alkali metal alkoxides, such as sodium methoxide, sodium ethoxide and potassium tert-butoxide are suitable, at temperatures between $-20°$ C. and $250°$ C., preferably between $0°$ C. and $150°$ C.

The malonic acid esters of the formula (VI)

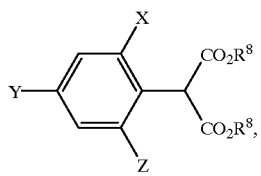

(VI)

in which
$R^8$, X, Y and Z have the meanings given above, are new.
They can be prepared by generally known methods of organic chemistry (cf., for example, Tetrahedron Lett. 27, 2763 (1986) and Organikum VEB Deutscher Verlag der Wissenschaften, Berlin 1977, p. 587 ff.).

The hydrazines of the formula (VII)

A—NH—NH—D (VII), in which
A and D have the meanings given above,
are known in some cases and/or can be prepared by methods known from the literature (cf., for example, Liebigs Ann. Chem. 585, 6 (1954); Reaktionen der organischen Synthese [Reactions of Organic Synthesis], C. Ferri, page 212, 513; Georg Thieme Verlag Stuttgart, 1978; Liebigs Ann. Chem. 443, 242 (1925); Chem. Ber. 98, 2551 (1965), EP 508126).

The acid halides of the formula (X), carboxylic anhydrides of the formula (XI), chloroformic acid esters or chloroformic acid thioesters of the formula (XII), chloromonothioformic acid esters or chlorodithioformic acid esters of the formula (XIII), alkyl halides of the formula (XIV), sulphonyl chlorides of the formula (XV), phosphorus compounds of the formula (XVI) and metal hydroxides, metal alkoxides or amines of the formula (XVII) and (XVIII) and isocyanates of the formula (XIX) and carbamoyl chlorides of the formula (XX) additionally needed as starting substances for carrying out processes (G), (H), (I), (J), (K), (L) and (M) according to the invention are generally known compounds of organic or inorganic chemistry.

The compounds of the formulae (VII), (VIII), (IX) to (XXI), (XXIV) and (XXXII) to (XXXIV) are moreover disclosed in the patent applications cited at the outset and/or can be prepared by the methods given there.

Process (A) is characterized in that compounds of the formula (II), in which A, B, D, X, Y, Z and $R^8$ have the meanings given above, are subjected to an intramolecular condensation in the presence of a diluent and in the presence of a base.

The diluents employed in process (A) according to the invention can be all organic solvents which are inert to the reaction participants. Those preferably utilizable are hydrocarbons, such as toluene and xylene, further ethers, such as dibutyl ether, tetrahydrofuran, dioxane, glycol dimethyl ether and diglycol dimethyl ether, additionally polar solvents, such as dimethyl sulphoxide, sulpholane, dimethylformamide and N-methyl-pyrrolidone, and also alcohols such as methanol, ethanol, propanol, iso-propanol, butanol, iso-butanol and tert-butanol.

Suitable bases (deprotonating agents) employed in carrying out process (A) according to the invention can be all customary proton acceptors. Those preferably utilizable are alkali metal and alkaline earth metal oxides, hydroxides and carbonates, such as sodium hydroxide, potassium hydroxide, magnesium oxide, calcium oxide, sodium carbonate, potassium carbonate and calcium carbonate, each of which can also be employed in the presence of phase-transfer catalysts, e.g. triethylbenzylammonium chloride, tetrabutylammonium bromide, Adogen 464 (=methyltrialkyl($C_8$–$C_{10}$) ammonium chloride) or TDA 1 (=tris-(methoxyethoxyethyl)-amine). Alkali metals such as sodium or potassium can furthermore be used. Alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can further be employed.

When carrying out process (A) according to the invention, the reaction temperature can be varied within a relatively wide range. In general, the reaction is carried out at temperatures between 0° C. and 250° C., preferably between 50° C. and 150° C.

Process (A) according to the invention is in general carried out under normal pressure.

When carrying out process (A) according to the invention, the reaction component of the formula (II) and the deprotonating base are in general employed in equimolar to approximately double equimolar amounts. However, it is also possible to use one component or the other in a relatively large excess (up to 3 mol).

Process (B) is characterized in that compounds of the formula (III), in which A, B, X, Y, Z and $R^8$ have the meanings given above, are condensed intramolecularly in the presence of a diluent and in the presence of a base.

The diluents employed in process (B) according to the invention can be all organic solvents which are inert to the reaction participants. Those preferably utilizable are hydrocarbons, such as toluene and xylene, further ethers, such as dibutyl ether, tetrahydrofuran, dioxane, glycol dimethyl ether and diglycol dimethyl ether, and additionally polar solvents, such as dimethyl sulphoxide, sulpholane, dimethylformamide and N-methyl-pyrrolidone. Alcohols such as methanol, ethanol, propanol, iso-propanol, butanol, iso-butanol and tert-butanol can furthermore be employed.

The bases (deprotonating agents) employed in carrying out process (B) according to the invention can be all customary proton acceptors. Those preferably utilizable are alkali metal and alkaline earth metal oxides, hydroxides and carbonates, such as sodium hydroxide, potassium hydroxide, magnesium oxide, calcium oxide, sodium carbonate, potassium carbonate and calcium carbonate, each of which can also be employed in the presence of phase-transfer catalysts, e.g. triethylbenzylammonium chloride, tetrabutylammonium bromide, Adogen 464 (=methyltrialkyl($C_8$–$C_{10}$) ammonium chloride) or TDA 1 (=tris-(methoxyethoxyethyl)-amine). Alkali metals such as sodium or potassium can furthermore be used. Alkali metal and alkaline earth metal amides and hydrides, such as sodium amide, sodium hydride and calcium hydride, and additionally also alkali metal alkoxides, such as sodium methoxide, sodium ethoxide and potassium tert-butoxide can additionally also be employed.

When carrying out process (B) according to the invention, the reaction temperature can be varied within a relatively wide range. In general, the reaction is carried out at temperatures between 0° C. and 250° C., preferably between 50° C. and 150° C.

Process (B) according to the invention is in general carried out under normal pressure.

When carrying out process (B) according to the invention, the reaction components of the formula (III) and the deprotonating bases are in general employed in approximately equimolar amounts. However, it is also possible to use one component or the other in a relatively large excess (up to 3 mol).

Process (C) is characterized in that compounds of the formula (IV), in which A, B, W, X, Y, Z and $R^8$ have the meaning given above, are cyclized intramolecularly in the presence of an acid and if appropriate in the presence of a diluent.

Diluents which can be employed in process (C) according to the invention are all organic solvents which are inert to the reaction participants. Those preferably utilizable are hydrocarbons, such as toluene and xylene, farther halogenated hydrocarbons such as dichloromethane, chloroform, ethylene chloride, chlorobenzene, dichlorobenzene, additionally polar solvents, such as dimethyl sulphoxide, sulpholane, dimethylformamide and N-methyl-pyrrolidone. Alcohols such as methanol, ethanol, propanol, iso-propanol, butanol, isobutanol, tert-butanol can furthermore be employed.

The acid employed can optionally also be used as a diluent.

Acids which can be employed in process (C) according to the invention are all customary inorganic and organic acids, e.g. hydrohalic acids, sulphuric acid, alkyl-, aryl- and haloalkylsulphonic acids; halogenated alkylcarboxylic acids, e.g. trifluoroacetic acid, are used in particular.

When carrying out process (C) according to the invention, the reaction temperature can be varied within a relatively wide range. In general, the reaction is carried out at temperatures between 0° C. and 250° C., preferably between 50° C. and 150° C.

Process (C) according to the invention is in general carried out under normal pressure.

When carrying out process (C) according to the invention, the reaction components of the formula (IV) and the acid are employed, for example, in equimolar amounts. However, it is optionally also possible to employ the acid in catalytic amounts.

Process (E) according to the invention is characterized in that carbonyl compounds of the formula (VIII) or their silyl enol ethers of the formula (VIIIa) are reacted with ketene acid halides of the formula (V), if appropriate in the presence of a diluent and if appropriate in the presence of an acid acceptor.

Diluents which can be employed in process (E) according to the invention are all organic solvents which are inert to the reaction participants. Those preferably utilizable are hydrocarbons, such as o-dichlorobenzene, tetralin, toluene and xylene, further ethers, such as dibutyl ether, glycol dimethyl ether and diglycol dimethyl ether, and additionally polar solvents, such as dimethyl sulphoxide, sulpholane, dimethylformamide or N-methyl-pyrrolidone.

Acid acceptors which can be used when carrying out process (E) according to the invention are all customary acid acceptors.

Those preferably utilizable are tertiary amines, such as triethylamine, pyridine, diazabicyclooctane (DABCO), diazabicycloundecane (DBU), diazabicyclononene (DBN), Hünig base or N,N-dimethyl-aniline.

When carrying out process (E) according to the invention, the reaction temperature can be varied within a relatively wide range. The reaction is expediently carried out at temperatures between 0° C. and 250° C., preferably between 50° C. and 220° C.

Process (E) according to the invention is preferably carried out under normal pressure.

When carrying out process (E) according to the invention, the reaction components of the formulae (VIII) and (V) and, if appropriate, the acid acceptor are in general employed in approximately equimolar amounts. However, it is also possible to use one component or the other in a relatively large excess (up to 5 mol).

Process (F) according to the invention is characterized in that thioamides of the formula (IX) are reacted with ketene acid halides of the formula (V), if appropriate in the presence of a diluent and if appropriate in the presence of an acid acceptor.

Diluents which can be employed in process variant (F) according to the invention are all inert organic solvents. Those preferably utilizable are hydrocarbons, such as o-dichlorobenzene, tetralin, toluene and xylene, farther ethers, such as dibutyl ether, glycol dimethyl ether and diglycol dimethyl ether, and additionally polar solvents, such as dimethyl sulphoxide, sulpholane, dimethylformamide and N-methyl-pyrrolidone.

Acid acceptors which can be used in carrying out process (F) according to the invention are all customary acid acceptors.

Those preferably utilizable are tertiary amines, such as triethylamine, pyridine, diazabicyclooctane (DABCO), diazabicycloundecane (DBU), diazabicyclononene (DBN), Hünig base and N,N-dimethyl-aniline.

When carrying out process (F) according to the invention, the reaction temperature can be varied within a relatively wide range. The reaction is expediently carried out at temperatures between 0° C. and 250° C., preferably between 20° C. and 220° C.

Process (F) according to the invention is expediently carried out under normal pressure.

When carrying out process (F) according to the invention, the reaction components of the formulae (IX) and (V) and, if appropriate, the acid acceptors are in general employed in approximately equimolar amounts. However, it is also possible to use one component or the other in a relatively large excess (up to 5 mol).

Process (Gα) is characterized in that compounds of the formulae (I-1-a) to (I-6-a) are in each case reacted with carboxylic acid halides of the formula (X), if appropriate in the presence of a diluent and if appropriate in the presence of an acid-binding agent.

Diluents which can be employed in process (Gα) according to the invention are all solvents inert to the acid halides. Those preferably utilizable are hydrocarbons, such as benzine, benzene, toluene, xylene and tetralin, further halogenohydrocarbons, such as methylene chloride, chloroform, carbon tetrachloride, chlorobenzene and o-dichlorobenzene, additionally ketones, such as acetone and methyl isopropyl ketone, furthermore ethers, such as diethyl ether, tetrahydrofuran and dioxane, moreover carboxylic acid esters, such as ethyl acetate, nitriles such as acetonitrile and also strongly polar solvents, such as dimethylformamide, dimethyl sulphoxide and sulpholane. If the stability to hydrolysis of the acid halide permits, the reaction can also be carried out in the presence of water.

In the reaction by process (Gα) according to the invention, suitable acid-binding agents are all customary acid acceptors. Those preferably utilizable are tertiary amines, such as triethylamine, pyridine, diazabicyclooctane (DABCO), diazabicycloundecene (DBU), diazabicyclononene (DBN), Hünig base and N,N-dimethyl-aniline, further alkaline earth metal alkoxides, such as magnesium and calcium oxide, additionally alkali metal and alkaline earth metal carbonates, such as sodium carbonate, potassium carbonate and calcium carbonate and also alkali metal hydroxides such as sodium hydroxide and potassium hydroxide.

In process (Gα) according to the invention, the reaction temperature can be varied within a relatively wide range. In general, the reaction is carried out at temperatures between −20° C. and +150° C., preferably between 0° C. and 100° C.

When carrying out process (Gα) according to the invention, the starting substances of the formulae (I-1-a) to (I-6-a) and the carboxylic acid halide of the formula (X) are in general each used in approximately equivalent amounts. However, it is also possible to employ the carboxylic acid halide in a relatively large excess (up to 5 mol). Working-up is carried out according to customary methods.

Process (Gβ) is characterized in that compounds of the formulae (I-1-a) to (I-6-a) are each reacted with carboxylic anhydrides of the formula (XI), if appropriate in the presence of a diluent and if appropriate in the presence of an acid-binding agent.

Diluents which can be used in process (Gβ) according to the invention are preferably those diluents which are also suitable when using acid halides. Otherwise, a carboxylic anhydride employed in an excess can also simultaneously function as diluent.

Possible acid-binding agents optionally added in process (Gβ) are preferably those acid-binding agents which are also suitable when using acid halides.

The reaction temperature in process (Gβ) according to the invention can be varied within a relatively wide range. In general, the reaction is carried out at temperatures between −20° C. and +150° C., preferably between 0° C. and 100° C.

When carrying out process (Gβ) according to the invention, the starting substances of the formulae (I-1-a) to (I-6-a) and the carboxylic anhydride of the formula (XI) are in general used in approximately equivalent amounts in each case. However, it is also possible to employ the carboxylic anhydride in a relatively large excess (up to 5 mol). Working-up is carried out according to customary methods.

In general, a procedure is used in which diluent and carboxylic anhydride present in excess and also the resulting carboxylic acid are removed by distillation or by washing with an organic solvent or with water.

Process (H) is characterized in that compounds of the formulae (I-1-a) to (I-6-a) are each reacted with chloroformic acid esters or chloroformic acid thioesters of the formula (XII), if appropriate in the presence of a diluent and if appropriate in the presence of an acid-binding agent.

Possible acid-binding agents in process (H) according to the invention are all customary acid acceptors. Those preferably utilizable are tertiary amines, such as triethylamine, pyridine, DABCO, DBU, DBA, Hünig base and N,N-dimethyl-aniline, Arther alkaline earth metal oxides, such as magnesium and calcium oxide, additionally alkali metal and alkaline earth metal carbonates, such as sodium carbonate, potassium carbonate and calcium carbonate and also alkali metal hydroxides such as sodium hydroxide and potassium hydroxide.

Diluents which can be employed in process (H) according to the invention are all solvents which are inert to the chloroformic acid esters or chloroformic acid thioesters. Those preferably utilizable are hydrocarbons, such as benzine, benzene, toluene, xylene and tetralin, further halogenohydrocarbons, such as methylene chloride, chloroform, carbon tetrachloride, chlorobenzene and o-dichlorobenzene, additionally ketones, such as acetone and methyl isopropyl ketone, furthermore ethers, such as diethyl ether, tetrahydrofuran and dioxane, nitrites such as acetonitrile, moreover carboxylic acid esters, such as ethyl acetate, and also strongly polar solvents, such as dimethylformamide, dimethyl sulphoxide and sulpholane.

When carrying out process (H) according to the invention, the reaction temperature can be varied within a relatively wide range. The reaction temperature is in general between −20° C. and +100° C., preferably between 0° C. and 50° C.

Process (H) according to the invention is in general carried out under normal pressure.

When carrying out process (H) according to the invention, the starting substances of the formulae (I-1-a) to (I-6-a) and the approporiate chloroformic acid esters or chloroformic acid thioesters of the formula (XII) are in general each used in approximately equivalent amounts. However, it is also possible to employ one component or the other in a relatively large excess (up to 2 mol). Working-up is carried out according to customary methods. In general, a procedure is used in which salts which are deposited are removed and the reaction mixture which remains is concentrated by stripping off the diluent.

Process (I) according to the invention is characterized in that compounds of the formulae (I-1-a) to (I-6-a) are each reacted with (Iα) compounds of the formula (XIII) in the presence of a diluent and if appropriate in the presence of an acid-binding agent or (Iβ) carbon disulphide and then with alkyl halides of the formula (XIV), if appropriate in the presence of a diluent and if appropriate in the presence of a base.

In preparation process (Iα), about 1 mol of chloromonothioformic acid ester or chlorodithioformic acid ester of the formula (XIII) is reacted at 0 to 120° C., preferably at 20 to 60° C., per mole of starting compound of the formulae (I-1-a) to (I-6-a).

Possible diluents optionally added are all inert polar organic solvents, such as ethers, amides, carboxylic acid esters, nitrites, sulphones, sulphoxides, but also halogenoalkanes.

Dimethyl sulphoxide, ethyl acetate, acetonitrile, tetrahydrofaran, dimethylformamide or methylene chloride is preferably employed.

If, in a preferred embodiment, the enolate salt of the compounds (I-1-a) to (I-6-a) is prepared by addition of strong deprotonating agents, e.g. sodium hydride or potassium tertiary butoxide, the further addition of acid-binding agents can be dispensed with.

If acid-binding agents are employed, customary inorganic or organic bases are suitable; sodium hydroxide, sodium carbonate, potassium carbonate, pyridine and triethylamine may be mentioned by way of example.

The reaction can be carried out at normal pressure or at elevated pressure; it is preferably carried out at normal pressure. Working-up takes place according to customary methods.

In preparation process (Iβ), the equimolar amount or an excess of carbon disulphide is in each case added per mole of starting compounds of the formulae (I-1-a) to (I-6-a). The reaction is in this case preferably carried out at temperatures from 0 to 50° C. and in particular at 20 to 30° C.

Often it is expedient first to prepare the corresponding salt from the compounds of the formulae (I-1-a) to (I-6-a) by addition of a base (e.g. potassium tertiary butoxide or sodium hydride). The compounds (I-1-a) to (I-6-a) are each reacted with carbon disulphide until the formation of the intermediate compound is complete, e.g. after stirring at room temperature for several hours.

Bases which can be employed in process (Iβ) are all customary proton acceptors. Those preferably utilizable are alkali metal hydrides, alkali metal alkoxides, alkali metal or alkaline earth metal carbonates or hydrogen carbonates or nitrogen bases. Those which may be mentioned, for example, are sodium hydride, sodium methoxide, sodium hydroxide, calcium hydroxide, potassium carbonate, sodium hydrogen carbonate, triethylamine, dibenzylamine, diisopropylamine, pyridine, quinoline, diazabicyclooctane (DABCO), diazabicyclononene (DBN) and diazabicycloundecene (DBU).

Diluents which can be used in this process are all customary solvents.

Those preferably utilizable are aromatic hydrocarbons such as benzene or toluene, alcohols such as methanol, ethanol, isopropanol or ethylene glycol, nitrites such as acetonitrile, ethers such as tetrahydrofuran or dioxane, amides such as dimethylformamide or other polar solvents such as dimethyl sulphoxide or sulpholane.

Further reaction with the alkyl halide of the formula (XIV) is preferably carried out at 0 to 70° C. and in particular at 20 to 50° C. In this case, at least the equimolar amount of alkyl halide is employed.

The reaction is carried out at normal pressure or at elevated pressure, preferably at normal pressure.

Working-up is in turn carried out according to customary methods.

Process (J) according to the invention is characterized in that compounds of the formulae (I-1-a) to (I-6-a) are each reacted with sulphonyl chlorides of the formula (XV), if appropriate in the presence of a diluent and if appropriate in the presence of an acid-binding agent.

In preparation process (J), about 1 mol of sulphonyl chloride of the formula (XV) is reacted at −20 to 150° C., preferably at 20 to 70° C., per mole of starting compound of the formula (I-1-a) to (I-6-a).

Process (J) is preferably carried out in the presence of a dilent.

Possible diluents are all inert polar organic solvents, such as ethers, amides, nitriles, sulphones, sulphoxides or halogenated hydrocarbons such as methylene chloride.

Dimethyl sulphoxide, tetrahydrofuran, dimethylformamide and methylene chloride are preferably employed.

If, in a preferred embodiment, the enolate salt of the compounds (I-1-a) to (I-6-a) is prepared by addition of strong deprotonating agents (e.g. sodium hydride or potassium tertiary butoxide), the further addition of acid-binding agents can be dispensed with.

If acid-binding agents are employed, customary inorganic or organic bases are suitable; those which may be mentioned by way of example are sodium hydroxide, sodium carbonate, potassium carbonate, pyridine and triethylamine.

The reaction can be carried out at normal pressure or at elevated pressure, preferably it is carried out at normal pressure. Working-up takes place according to customary methods.

Process (K) according to the invention is characterized in that compounds of the formulae (I-1-a) to (I-6-a) are each reacted with phosphorus compounds of the formula (XVI), if appropriate in the presence of a diluent and if appropriate in the presence of an acid-binding agent.

In preparation process (K), to obtain compounds of the formulae (I-1-e) to (I-6-e), 1 to 2, preferably 1 to 1.3, mol of the phosphorus compound of the formula (XVI) are reacted at temperatures between −40° C. and 150° C., preferably between −10 and 110° C., relative to 1 mol of the compounds (I-1-a) to (I-6-a).

Process (K) is preferably carried out in the presence of a diluent.

Possible diluents are all inert, polar organic solvents, such as halogenohydrocarbons, carboxylic acid esters, ethers, amides, nitrites, sulphones, sulphoxides etc.

Acetonitrile, dimethyl sulphoxide, tetrahydrofuran, dimethylformamide and methylene chloride are preferably employed.

Possible acid-binding agents optionally added are customary inorganic or organic bases such as hydroxides, carbonates or amines. Those which may be mentioned by way of example are sodium hydroxide, sodium carbonate, potassium carbonate, pyridine and triethylamine.

The reaction can be carried out at normal pressure or at elevated pressure, preferably at normal pressure. Working-up takes place according to customary methods of organic chemistry. The final products are preferably purified by crystallization, chromatographic purification or by so-called "incipient distillation", i.e. removal of the volatile constituents in vacuo.

Process (L) is characterized in that compounds of the formulae (I-1-a) to (I-6-a) are each reacted with metal hydroxides or metal alkoxides of the formula (XVII) or amines of the formula (XVIII), if appropriate in the presence of a diluent.

Diluents which can be employed in process (L) according to the invention are preferably ethers such as tetrahydrofuran, dioxane, diethyl ether or else alcohols such as methanol, ethanol, isopropanol, but also water. Process (L) according to the invention is in general carried out under normal pressure. The reaction temperature is in general between −20° C. and 100° C., preferably between 0° C. and 50° C.

Process (M) according to the invention is characterized in that compounds of the formulae (I-1-a) to (I-6-a) are each reacted (Mα) with compounds of the formula (XIX), if appropriate in the presence of a diluent and if appropriate in the presence of a catalyst, or (Mβ) with compounds of the formula (XX), if appropriate in the presence of a diluent and if appropriate in the presence of an acid-binding agent.

In preparation process (Mα), about 1 mol of isocyanate of the formula (XIX) is reacted at 0 to 100° C., preferably at 20 to 50° C., per mole of starting compound of the formulae (I-1-a) to (I-6-a).

Process (Mα) is preferably carried out in the presence of a diluent.

Possible diluents are all inert organic solvents, such as ethers, amides, nitriles, sulphones or sulphoxides.

Catalysts can optionally be added to accelerate the reaction. The catalysts employed can very advantageously be organotin compounds, e.g. dibutyltin dilaurate.

The reaction is preferably carried out at normal pressure.

In preparation process (Mβ), about 1 mol of carbamoyl chloride of the formula (XX) is reacted at 0 to 150° C., preferably at 20 to 70° C., per mole of starting compound of the formulae (I-1-a) to (I-6-a).

Possible diluents optionally added are all inert polar organic solvents, such as ethers, carboxylic acid esters, nitrites, amides, sulphones, sulphoxides or halogenated hydrocarbons.

Dimethyl sulphoxide, tetrahydrofuran, dimethylformamide and methylene chloride are preferably employed.

If, in a preferred embodiment, the enolate salt of the compound (I-1-a) to (I-6-a) is prepared by addition of strong deprotonating agents (e.g. sodium hydride or potassium tertiary butoxide), the further addition of acid-binding agents can be dispensed with.

If acid-binding agents are employed, customary inorganic or organic bases are suitable; those which may be mentioned by way of example are sodium hydroxide, sodium carbonate, potassium carbonate, triethylarnine or pyridine.

The reaction can be carried out at normal pressure or at elevated pressure, preferably at normal pressure. Working-up takes place according to customary methods.

The active compounds are suitable for controlling animal pests, preferably arthropods and nematodes, in particular insects and arachnida, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus nibis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Omithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds according to the invention are distinguished by a high insecticidal and acaricidal activity.

They can be used to particularly good effect for controlling insects which are injurious to plants, such as, for example, against the larvae of the mustard beetle (*Phaedon cochleariae*) or against the larvae of the green rice leaf hopper (*Nephotettix cincticeps*) or against the caterpillars of the cabbage moth (*Plutella maculipennis*).

The active compounds according to the invention can furthermore be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The dosages of the active compounds according to the invention necessary for controlling weeds are betweeen 0.001 and 10 kg/ha, preferably between 0.005 and 5 kg/ha.

The active compounds according to the invention can be used, for example, in connection with the following plants:

Dicolyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective combating of weeds in annual cultures.

The active compounds according to the invention are very highly suitable for the selective control of monocotyledon weeds in dicotyledon crops pre- and post-emergence. They can be employed to very good effect for the control of grass weeds, for example in cotton or sugar beet.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents.

As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and. natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compound according to the invention can be present in its commercially available formulations and in the use forms prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

Examples of particularly advantageous mixture components are the following compounds:

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)benzamide; (E)-2-methoxyimino-N-methyl-2-(2-phenoxyphenyl)-acetamide; 8-hydroxyquinoline sulphate; methyl (E)-2-{2-[6-(2-cyanophenoxy)pyrimidin-4-yloxy]-phenyl}-3-methoxyacrylate; methyl (E)-methoximino [alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminum, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulfur and sulfur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichiamide, tricyclazole, tridemorph, triflumizole, triforine, triticonazole, validamycin A, vinclozolin, zineb, ziram Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos,

RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarh, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Herbicides:

for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenz-thiazuron; hydroxylamines such as, for example, alloxydim, clethodim, cycloxydim, sethoxydim and tralkoxydim; imidazolinones such as, for example, imazethapyr, imaza-methabenz, imazapyr and imazaquin; nitriles such as, for example, bromoxynil, dichlobenil and ioxynil; oxyacetamides such as, for example, mefenacet; sulfonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methy, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compound according to the invention can furthermore be present in its commercially available formulations and in the use forms prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are not only active against plant, hygiene and stored product pests, but also, in the veterinary medicine sector, against animal parasites (ectoparasites), such as scaly ticks, Argasidae, scab mites, Trombidae, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp., Solenopotes spp.

From the order of the Mallophagida and the suborders Amblycerina and Ischnocerina, for example, Trimenopon spp., Menopon spp., Trinoton spp., Bovicola spp., Werneckiella spp., Lepikentron spp., Damalina spp., Trichodectes spp., Felicola spp.

From the order Diptera and the suborders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp., Melophagus spp.

From the order of the Siphonapterida, for example, Pulex spp., Ctenocephalides spp., Xenopsylla spp., Ceratophyllus spp.

From the order of the Heteropterida, for example, Cimex spp., Triatoma spp., Rhodnius spp., Panstrongylus spp.

From the order of the Blattarida, for example, *Blatta orientalis, Periplaneta americana, Blattela germanica,* Supella spp.

From the subclass of the Acaria (Acarida) and the orders of the Meta- and Mesostigmata, for example, Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Sternostoma spp., Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp., Laminosioptes spp.

For example, they exhibit an outstanding activity against *Boophilus microplus* and *Lucilia cuprina.*

The active compounds of the formula (I) according to the invention are also suitable for controlling arthropods which infest agricultural productive livestock such as, for example, cattle, sheep, goats, horses, pigs, donkeys, camels, buffalo, rabbits, chickens, turkeys, ducks, geese and bees, other pets, such as, for example, dogs, cats, cage birds and aquarium fish, and also so-called test animals, such as, for example, hamsters, guinea pigs, rats and mice. By controlling these anthropods cases of death and reductions in productivity (for meat, milk, wool, hides, eggs, honey etc) should be diminished, so that more economic and simpler animal husbandry is possible by use of the active compounds according to the invention.

The active compounds according to the invention are used in the veterinary sector in a known manner by enteral administration in the form of, for example, tablets, capsules, potions, drenches, granules, pastes, boli, the feed-through process and suppositories, by parenteral administration, such as, for example, by injections (intramuscular, subcutaneous, intravenous, intraperitoneal etc), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices, etc.

When used for livestock, poultry, pets etc., the active compounds of the formula (I) can be applied as formulations (for example powders, emulsions, fluid compositions) which contain the active compounds in an amount from 1 to 80% by weight, directly or after 100 to 10,000-fold dilution or they can be used as a chemical bath.

It was additionally found that the compounds of the formula I according to the invention exhibit a high insecticidal action against insects which destroy industrial materials.

The following insects may be mentioned by way of example and preferably—but without being limitative:

Beetles such as
  *Hylotrupes bajulus, Chlorophorus pilosis, Anobium punctatum, Xestobium rufovillosum, Ptilinus pecticornis, Dendrobiium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec. Tryptodendron spec. *Apate monachus, Bostrychus capucins, Heterobostrychus brunneus,* Sinoxylon spec. *Dinoderus minutus.*

Hymenopterans such as
  *Sirex juvencus, Urocerus gigas, Urocerus gigas taignus, Urocerus augur.*

Termites such as
  *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Brushtails
  such as *Lepisma saccharina.*

Industrial materials in the present connection are to be understood as meaning non-living materials, preferably such as plastics, adhesives, sizes, paper and card, leather, wood and wood-processing products and paints.

Very particularly preferably, the materials to be protected from insect attack are wood and wood-processing products.

Wood and wood-processing products which can be protected by the agent according to the invention or mixtures containing the latter are, for example, to be understood as meaning: construction timber, wooden beams, railway sleepers, bridge components, jetties, vehicles made of wood, boxes, palettes, containers, telegraph poles, wood lagging, windows and doors made of wood, plywood, particle board, joiner's work or wood products which, quite generally, are used in building or joinery.

The active compounds can be used as such, in the form of concentrates or generally customary formulations such as powders, granules, solutions, suspensions, emulsions or pastes.

The formulations mentioned can be prepared in a manner known per se, e.g. by mixing the active compounds with at least one solvent or diluent, emulsifier, dispersant and/or binder or fixative, water-repellent, if appropriate siccatives and UV stabilizers and if appropriate colorants and pigments as well as further processing aids.

The insecticidal compositions or concentrates used for the protection of wood and wood materials contain the active compound according to the invention in a concentration from 0.0001 to 95% by weight, in particular 0.001 to 60% by weight.

The amount of the compositions or concentrates employed is dependent on the nature and the occurrence of the insects and on the medium. In use, the optimum amount to employ can in each case be determined by test series. In general, however, it is sufficient to employ 0.0001 to 20% by weight, preferably 0.001 to 10% by weight, of the active compound, based on the material to be protected.

The solvent and/or diluent used is an organic chemical solvent or solvent mixture and/or an oily or oleaginous poorly volatile organic chemical solvent or solvent mixture and/or a polar organic chemical solvent or solvent mixture and/or water and, if appropriate, an emulsifier and/or wetting agent.

Organic chemical solvents employed are preferably oily or oleaginous solvents having an evaporation number of over 35 and a flash point of above 30° C., preferably above 45° C. Poorly volatile, water-insoluble, oily and oleaginous solvents of this type used are appropriate mineral oils or their aromatic fractions or mineral oil-containing solvent mixtures, preferably white spirit, petroleum and/or alkylbenzene.

Advantageously, mineral oils having a boiling range from 170 to 220° C., white spirit having a boiling range from 170 to 220° C., spindle oil having a boiling range from 250 to 350° C., petroleum or aromatics of boiling range from 160 to 280° C., turpentine and the like are used.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic poorly volatile oily or oleaginous solvents having an evaporation number of over 35 and a flash point of above 30° C., preferably above 45° C., can be partially replaced by readily or moderately volatile organic chemical solvents, with the proviso that the solvent mixture also has an evaporation number of over 35 and a flash point of above 30° C., preferably above 45° C., and that the insecticide-fungicide mixture is soluble or emulsifiable in this solvent mixture.

According to a preferred embodiment, a part of the organic chemical solvent or solvent mixture or an aliphatic polar organic chemical solvent or solvent mixture is replaced. Preferably, aliphatic organic chemical solvents containing hydroxyl and/or ester and/or ether groups, such as, for example, glycol ethers, esters or the like are used.

Organic chemical binders used in the context of the present invention are the plastic resins and/or binding drying oils which are water-dilutable and/or soluble or dispersible or emulsifiable in the organic chemical solvents employed, in particular binders consisting of or comprising an acrylate resin, a vinyl resin, e.g. polyvinyl acetate, polyester resin, polycondensation or polyaddition resin, polyurethane resin, alkyd resin or modified alkyd resin, phenolic resin, hydrocarbon resin such as indene-coumarone resin, silicone resin, drying vegetable and/or drying oils and/or physically drying binders based on a natural and/or synthetic resin.

The synthetic resin used as a binder can be employed in the form of an emulsion, dispersion or solution. The binders used can also be bitumen or bituminous substances up to 10% by weight. Additionally, dyes, pigments, water-repellent agents, odour corrigents and inhibitors or anticorrosive agents and the like known per se can be employed.

According to the invention, at least one alkyd resin or modified alkyd resin and/or a drying vegetable oil is preferably contained in the composition or in the concentrate as organic chemical binder. According to the invention, alkyd resins having an oil content of more than 45% by weight, preferably 50 to 68% by weight, are preferably used.

The binder mentioned can be completely or partially replaced by a fixing agent (mixture) or a plasticizer (mixture). These additives are intended to prevent volatilization of the active compounds and crystallization or precipitation. They preferably replace 0.01 to 30% of the binder (based on 100% of the binder employed).

The plasticizers originate from the chemical classes of phthalic acid esters such as dibutyl, dioctyl or benzyl butyl phthalate, phosphoric acid esters such as tributyl phosphate, adipic acid esters such as di-(2-ethylhexyl) adipate, stearates such as butyl stearate or amyl stearate, oleates such as butyl oleate, glycerol ethers or higher molecular weight glycol ethers, glycerol esters and p-toluenesulphonic acid esters.

Fixing agents are based chemically on polyvinyl alkyl ethers such as, for example, polyvinyl methyl ether or ketones such as benzophenone, ethylenebenzophenone.

A possible solvent or diluent is, in particular, also water, if appropriate as a mixture with one or more of the above-mentioned organic chemical solvents or diluents, emulsifiers and dispersants.

Particularly effective wood protection is achieved by large-scale impregnation processes, e.g. vacuum, double vacuum or pressure processes.

The ready-to-use compositions can optionally also contain further insecticides and optionally also one or more fungicides.

Possible additional mixture components are preferably the insecticides and fungicides mentioned in WO 94/29268. The compounds mentioned in this document are explicit constituents of the present application.

Very particularly preferred mixture components can be insecticides, such as chlorpyriphos. phoxim, silafluofin, alphamethrin, cyfluthrin, cypermethrin, deltamethrin, permethrin, imidacloprid, NI-25, flufenoxuron, hexaflumuron and triflumuron, as well as fingicides such as epoxyconazole, hexaconazole, azaconazole, propiconazole, tebuconazole, cyproconazole, metconazole, imazalil, dichlofluanid, tolylfluanid, 3-iodo-2-propinyl butylcarbamate, N-octyl-isothiazolin-3-one and 4,5-dichloro-N-octylisothiazolin-3-one.

The preparation and the use of the active compounds according to the invention follow from the examples below.

PREPARATION EXAMPLES

Example (I-1-a-1)

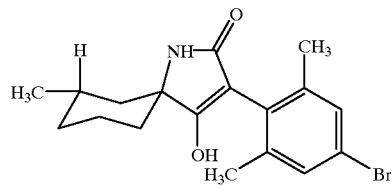

32.6 g of the compound according to Example (II-1), dissolved in 200 ml of absolute toluene, are added dropwise at reflux temperature to 20.42 g (0.181 mol) of potassium tert-butoxide in 70 ml of absolute tetrahydrofuran (THF) and the mixture is stirred at this temperature for a further 1.5 hours.

For working-up, it is diluted with water, the phases are separated, the toluene phase is extracted with water and the combined aqueous phases are acidified with conc. HCl. The product is filtered off with suction, washed and dried and finally stirred in methyl tert-butyl (MTB) ether/n-hexane, filtered off with suction and dried.

Yield: 20.6 g (68% of theory); m.p.: >220° C.

The compounds of the formula (I-1-a) shown in Table 21 below were obtained analogously to Example (I-1-a-1) or according to the general details for preparation.

TABLE 21

(I-1-a)

A structure showing a pyrrolinone with OH, X, Y, Z substituents on phenyl, with A, B on ring carbon and D on N.

| Ex. No. | X | Y | Z | B | A | D | M.p.: °C. | Isomer |
|---|---|---|---|---|---|---|---|---|
| I-1-a-2 | CH₃ | Br | CH₃ | —(CH₂)₂—CHCH₃—(CH₂)₂— | | H | 211 | β |
| I-1-a-3 | CH₃ | Br | CH₃ | —(CH₂)₂—O—(CH₂)₂— | | H | 201 | — |
| I-1-a-4 | CH₃ | Br | CH₃ | CH₃ | i-C₃H₇ | H | 183 | — |
| I-1-a-5 | CH₃ | CH₃ | Br | —(CH₂)₂—CHCH₃—(CH₂)₂— | | H | >220 | β |
| I-1-a-6 | CH₃ | CH₃ | Br | —(CH₂)₃—CHCH₃—CH₂— | | H | 196 | β |
| I-1-a-7 | CH₃ | CH₃ | Br | —(CH₂)₂—O—(CH₂)₂— | | H | >220 | — |
| I-1-a-8 | CH₃ | CH₃ | Br | CH₃ | i-C₃H₇ | H | 194 | — |
| I-1-a-9 | CH₃ | CH₃ | Cl | —(CH₂)₂—CHCH₃—(CH₂)₂— | | H | >220 | β |
| I-1-a-10 | C₂H₅ | Br | CH₃ | —(CH₂)₂—CHCH₃—(CH₂)₂— | | H | >220 | β |
| I-1-a-11 | CH₃ | CH₃ | Br | —(CH₂)₂—CHOCH₃—(CH₂)₂— | | H | 124 | β |
| I-1-a-12 | CH₃ | CH₃ | Br | CH₃ | CH₃ | H | >220 | — |
| I-1-a-13 | CH₃ | CH₃ | Br | H | —CH₂—CHCH₃—CHCH₃— | H | >220 | cis |
| I-1-a-14 | CH₃ | CH₃ | Br | H | —CH₂—CHCH₃—CHCH₃— | H | >220 | trans |
| I-1-a-15 | CH₃ | CH₃ | Br | H | —CH₂—S—CH₂—CH₂— | H | >220 | — |
| I-1-a-16 | CH₃ | CH₃ | Br | H | —(CH₂)₄— | H | >220 | — |
| I-1-a-17 | CH₃ | CH₃ | Br | H | H | i-C₃H₇ | >220 | — |
| I-1-a-18 | CH₃ | Br | CH₃ | —(CH₂)₂—CHOCH₃—(CH₂)₂— | | H | >220 | β |
| I-1-a-19 | C₂H₅ | Br | CH₃ | —(CH₂)₂—O—(CH₂)₂— | | H | >220 | — |
| I-1-a-20 | C₂H₅ | Br | C₂H₅ | —(CH₂)₂—CHCH₃—(CH₂)₂— | | H | >220 | β |
| I-1-a-21 | CH₃ | Cl | CH₃ | —(CH₂)₂—CHCH₃—(CH₂)₂— | | H | >220 | β |
| I-1-a-22 | CH₃ | Cl | CH₃ | —(CH₂)₂—CHOCH₃—(CH₂)₂— | | H | >220 | β |
| I-1-a-23 | CH₃ | Cl | CH₃ | CH₃ | CH₃ | H | >220 | — |
| I-1-a-24 | CH₃ | CH₃ | Cl | —(CH₂)₂—CHOCH₃—(CH₂)₂— | | H | >220 | β |
| I-1-a-25 | CH₃ | CH₃ | Cl | —(CH₂)₃—CHCH₃—(CH₂)₂— | | H | 196 | β |
| I-1-a-26 | CH₃ | CH₃ | Cl | CH₃ | CH₃ | H | >220 | — |
| I-1-a-27 | CH₃ | CH₃ | Cl | —(CH₂)₂—O—(CH₂)₂— | | H | >220 | — |
| I-1-a-28 | CH₃ | CH₃ | Cl | CH₃ | i-C₃H₇ | H | >220 | — |

Example (I-1-b-1)

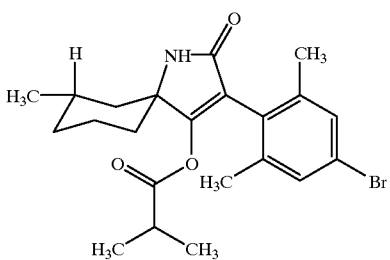

1.9 ml (18 mmol) of isobutyryl chloride, dissolved in 5 ml of absolute methylene chloride, are added dropwise at 0° C. to 10° C. to 4.37 g of the compound according to Example (I-1-a-1) in 70 ml of absolute methylene chloride and 2.52 ml (18 mmol) of triethylamine. The mixture is stirred at room temperature until the reaction is complete according to thin-layer chromatographic (TLC) checking.

For working-up, it is washed 2 times with 0.5 N NaOH, dried and evaporated. The crude product is recrystallized from MTB ether/n-hexane.

Yield: 1.70 g (32% of theory); m.p.: 208° C.

The examples of the formula (I-1-b) shown in Table 22 below were prepared analogously to Example (I-1-b-1) or according to the general details for preparation.

TABLE 22

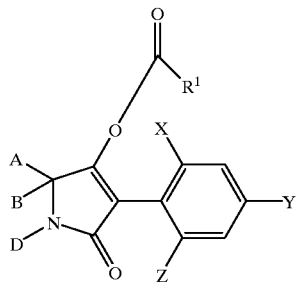
(I-1-b)

| Ex No | X | Y | Z | B | A | D | R¹ | M.p.: °C. | Isomer |
|---|---|---|---|---|---|---|---|---|---|
| I-1-b-2 | $CH_3$ | Br | $CH_3$ | —$(CH_2)_2$—$CHCH_3$—$(CH_2)_2$— | | H | $CH_3$— | 209 | β |
| I-1-b-3 | $CH_3$ | Br | $CH_3$ | —$(CH_2)_2$—$CHCH_3$—$(CH_2)_2$— | | H | i-$C_3H_7$— | 212 | β |
| I-1-b-4 | $CH_3$ | Br | $CH_3$ | —$(CH_2)_2$—$CHCH_3$—$(CH_2)_2$— | | H | $H_5C_2$—O—$CH_2$— | >220 | β |
| I-1-b-5 | $CH_3$ | Br | $CH_3$ | —$(CH_2)_3$—$CHCH_3$—$CH_2$— | | H | $CH_3$— | 191 | β |
| I-1-b-6 | $CH_3$ | Br | $CH_3$ | —$(CH_2)_3$—$CHCH_3$—$CH_2$— | | H | Cl-C₆H₄— | >220 | β |
| I-1-b-7 | $CH_3$ | Br | $CH_3$ | —$(CH_2)_2$—O—$(CH_2)_2$— | | H | $CH_3$— | 178 | — |
| I-1-b-8 | $CH_3$ | Br | $CH_3$ | —$(CH_2)_2$—O—$(CH_2)_2$— | | H | i-$C_3H_7$— | 202 | — |
| I-1-b-9 | $CH_3$ | $CH_3$ | Br | —$(CH_2)_2$—$CHCH_3$—$(CH_2)_2$— | | H | $CH_3$— | 181 | β |
| I-1-b-10 | $CH_3$ | $CH_3$ | Br | —$(CH_2)_2$—$CHCH_3$—$(CH_2)_2$— | | H | i-$C_3H_7$— | 208 | β |
| I-I-b-11 | $CH_3$ | $CH_3$ | Br | —$(CH_2)_2$—$CHCH_3$—$(CH_2)_2$— | | H | i-$C_4H_9$— | 212 | β |
| I-1-b-12 | $CH_3$ | $CH_3$ | Br | —$(CH_2)_2$—$CHCH_3$—$(CH_2)_2$— | | H | t-$C_4H_9$—$CH_2$— | >220 | β |
| I-1-b-13 | $CH_3$ | $CH_3$ | Br | —$(CH_2)_3$—$CHCH_3$—$CH_2$— | | H | $CH_3$— | 196 | β |
| I-I-b-14 | $CH_3$ | $CH_3$ | Br | —$(CH_2)_3$—$CHCH_3$—$CH_2$— | | H | i-$C_3H_7$— | 207 | β |
| I-1-b-15 | $CH_3$ | $CH_3$ | Br | —$(CH_2)_3$—$CHCH_3$—$CH_2$— | | H | t-$C_4H_9$—$CH_2$— | >220 | β |
| I-1-b-16 | $CH_3$ | $CH_3$ | Br | —$(CH_2)_3$—$CHCH_3$—$CH_2$— | | H | $H_5C_2$—O—$CH_2$— | 216 | β |
| I-1-b-17 | $CH_3$ | $CH_3$ | Br | —$(CH_2)_3$—$CHCH_3$—$CH_2$— | | H | Cl-C₆H₄— | >220 | β |
| I-1-b-18 | $CH_3$ | $CH_3$ | Br | —$(CH_2)_2$—O—$(CH_2)_2$— | | H | $(CH_3)_2C$=CH— | >220 | — |
| I-1-b-19 | $CH_3$ | $CH_3$ | Br | —$(CH_2)_2$—$CHCH_3$—$(CH_2)_2$— | | H | $C_2H_5$—O—$CH_2$ | 214 | β |
| I-1-b-20 | $CH_3$ | $CH_3$ | Br | —$(CH_2)_2$—$CHCH_3$—$(CH_2)_2$— | | H | t-$C_4H_9$— | >220 | β |
| I-1-b-21 | $CH_3$ | $CH_3$ | Br | —$(CH_2)_2$—$CHCH_3$—$(CH_2)_2$— | | H | $(CH_3)_2C$=CH— | 193 | β |
| I-1-b-22 | $C_2H_5$ | Br | $CH_3$ | —$(CH_2)_2$—$CHCH_3$—$(CH_2)_2$— | | H | $CH_3$— | 222 | β |
| I-1-b-23 | $C_2H_5$ | Br | $CH_3$ | —$(CH_2)_2$—$CHCH_3$—$(CH_2)_2$— | | H | i-$C_3H_7$— | 161 | β |
| I-1-b-24 | $C_2H_5$ | Br | $CH_3$ | —$(CH_2)_2$—$CHCH_3$—$(CH_2)_2$— | | H | i-$C_4H_9$— | 171 | β |
| I-1-b-25 | $C_2H_5$ | Br | $CH_3$ | —$(CH_2)_2$—$CHCH_3$—$(CH_2)_2$— | | H | $C_2H_5$—O—$CH_2$— | 166 | β |
| I-1-b-26 | $C_2H_5$ | Br | $CH_3$ | —$(CH_2)_2$—O—$(CH_2)_2$— | | H | i-$C_3H_7$— | 211 | — |
| I-1-b-27 | $C_2H_5$ | Br | $CH_3$ | —$(CH_2)_2$—O—$(CH_2)_2$— | | H | i-$C_4H_9$— | 205 | — |
| I-1-b-28 | $CH_3$ | Br | $CH_3$ | —$(CH_2)_2$—$CHOCH_3$—$(CH_2)_2$— | | H | i-$C_3H_7$— | >220 | β |
| I-1-b-29 | $CH_3$ | Cl | $CH_3$ | —$(CH_2)_2$—$CHCH_3$—$(CH_2)_2$— | | H | i-$C_3H_7$— | 214 | β |
| I-1-b-30 | $CH_3$ | Cl | $CH_3$ | —$(CH_2)_2$—$CHCH_3$—$(CH_2)_2$— | | H | $C_2H_5$—O—$CH_2$— | 168 | β |
| I-1-b-31 | $CH_3$ | $CH_3$ | Cl | —$(CH_2)_2$—$CHCH_3$—$(CH_2)_2$— | | H | i-$C_4H_9$— | 190 | β |
| I-1-b-32 | $CH_3$ | $CH_3$ | Cl | —$(CH_2)_2$—$CHCH_3$—$(CH_2)_2$— | | H | $C_2H_5$—O—$CH_2$— | 153 | β |
| I-1-b-33 | $CH_3$ | $CH_3$ | Cl | $CH_3$ | $CH_3$ | H | i-$C_3H_7$— | 182 | — |
| I-I-b-34 | $CH_3$ | $CH_3$ | Cl | —$(CH_2)_2$—O—$(CH_2)_2$— | | H | i-$C_3H_7$— | 183 | — |
| I-1-b-35 | $CH_3$ | $CH_3$ | Cl | —$(CH_2)_2$—O—$(CH_2)_2$— | | H | i-$C_4H_9$— | >220 | — |
| I-1-b-36 | $CH_3$ | $CH_3$ | Cl | $CH_3$ | i-$C_3H_7$ | H | i-$C_3H_7$— | oil | — |
| I-1-b-37 | $CH_3$ | $CH_3$ | Cl | $CH_3$ | i-$C_3H_7$ | H | i-$C_4H_9$— | oil | — |

Example (I-1-c-1)

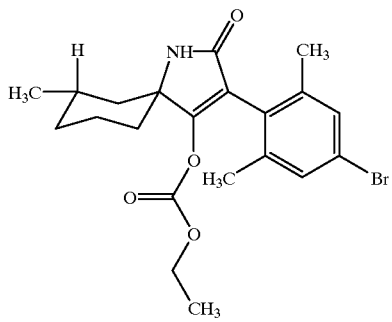

1.2 ml of ethyl chloroformate in 3 ml of absolute methylene chloride are added dropwise at 0° C. to 10° C. to 4.37 g of the compound according to Example (I-1-a-1) in 70 ml of absolute methylene chloride and 1.7 ml (12 mmol) of triethylamine. The mixture is stirred at room temperature until the reaction is complete according to TLC checking.

For working-up, it is washed 2 times with 0.5 N NaOH, dried and evaporated. The crude product is recrystallized from MTB ether/n-hexane.

Yield: 3.60 g (68% of theory); m.p.: >220° C.

The compounds of the formula (I-1-c) shown in Table 23 below were prepared analogously to Example (I-1-c-1) or according to the general details for preparation.

Example I-1-d-1

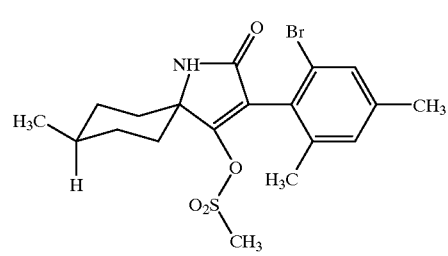

3.64 g of the compound according to Example I-1-a-5 and 1.4 ml of triethylamine in 50 ml of abs. methylene chloride are treated at 0 to 10° C. with 0.8 ml of methanesulphonyl chloride in 5 ml of abs. methylene chloride and the mixture is then stirred at room temperature. After reaction is complete (checking by means of thin-layer chromatography (TLC)), the mixture is washed 2 times with 50 ml of 0.5 N NaOH, dried over magnesium sulphate and concentrated, and the residue is recrystallized from MTB ether/n-hexane.

Yield 2.90 g (65% of theory), m.p. >220° C.

TABLE 23

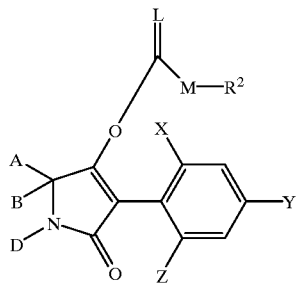

(I-c-1)

| Ex. No. | X | Y | Z | B | A | D | L | M | $R^2$ | M.p.: ° C. | Isomer |
|---|---|---|---|---|---|---|---|---|---|---|---|
| I-1-c-2 | $CH_3$ | Br | $CH_3$ | —$(CH_2)_2$—$CHCH_3$—$(CH_2)_2$— | | H | O | O | $C_2H_5$— | 217 | β |
| I-1-c-3 | $CH_3$ | Br | $CH_3$ | —$(CH_2)_2$—O—$(CH_2)_2$— | | H | O | O | $C_2H_5$— | >220 | — |
| I-1-c-4 | $CH_3$ | $CH_3$ | Br | —$(CH_2)_2$—$CHCH_3$—$(CH_2)_2$— | | H | O | O | $C_2H_5$— | 167 | β |
| I-I-c-5 | $CH_3$ | $CH_3$ | Br | —$(CH_2)_2$—$CHCH_3$—$CH_2$— | | H | O | O | $C_2H_5$— | 193 | β |
| I-I-c-6 | $CH_3$ | $CH_3$ | Br | —$(CH_2)_2$—O—$(CH_2)_2$— | | H | O | O | $C_2H_5$— | 217 | — |
| I-1-c-7 | $CH_3$ | $CH_3$ | Br | —$(CH_2)_2$—$CHCH_3$—$(CH_2)_2$— | | H | O | O | $i\text{-}C_4H_9$— | 201 | β |
| I-1-c-8 | $CH_3$ | $CH_3$ | Br | —$(CH_2)_2$—$CHCH_3$—$(CH_2)_2$— | | H | O | O | $C_6H_5$— | >220 | β |
| I-1-c-9 | $CH_3$ | $CH_3$ | Br | —$(CH_2)_2$—$CHCH_3$—$(CH_2)_2$— | | H | O | O | $C_6H_5$—$CH_2$ | >220 | β |
| I-1-c-10 | $C_2H_5$ | Br | $CH_3$ | —$(CH_2)_2$—$CHCH_3$—$(CH_2)_2$— | | H | O | O | $i\text{-}C_4H_9$— | 174 | β |
| I-1-c-11 | $C_2H_5$ | Br | $CH_3$ | —$(CH_2)_2$—O—$(CH_2)_2$— | | H | O | O | $i\text{-}C_4H_9$— | >220 | — |
| I-1-c-12 | $CH_3$ | Cl | $CH_3$ | $CH_3$ | $CH_3$ | H | O | O | $i\text{-}C_4H_9$— | 157 | — |
| I-1-c-13 | $CH_3$ | $CH_3$ | Cl | —$(CH_2)_2$—$CHCH_3(CH_2)_2$— | | H | O | O | $i\text{-}C_4H_9$— | 193 | β |
| I-1-c-14 | $CH_3$ | $CH_3$ | Cl | $CH_3$ | $CH_3$ | H | O | O | $i\text{-}C_4H_9$— | 118 | — |
| I-1-c-15 | $CH_3$ | $CH_3$ | Cl | —$(CH_2)_2$—O—$(CH_2)_2$— | | H | O | O | $C_2H_5$— | >220 | — |
| I-1-c-16 | $CH_3$ | $CH_3$ | Cl | —$(CH_2)_2$—O—$(CH_2)_2$— | | H | O | O | $i\text{-}C_4H_9$— | 205 | — |
| I-1-c-17 | $CH_3$ | $CH_3$ | Br | H | —$(CH_2)_4$— | | O | S | $i\text{-}C_3H_7$— | oil | — |
| I-1-c-18 | $CH_3$ | $CH_3$ | Br | H | —$(CH_2)_4$— | | O | S | $t\text{-}C_4H_9$— | oil | — |
| I-1-c-19 | $CH_3$ | $CH_3$ | Br | H | H | $i\text{-}C_3H_7$ | O | S | $i\text{-}C_3H_7$— | 124 | — |
| I-1-c-20 | $CH_3$ | $CH_3$ | Br | H | H | $i\text{-}C_3H_7$ | O | S | $t\text{-}C_4H_9$— | 169 | — |

Example (II-1)

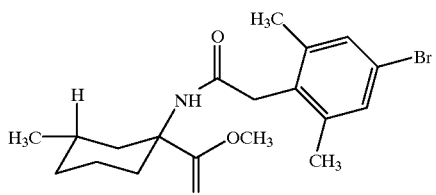

23.1 g of 2,6-dimethyl-4-bromo-phenylacetic acid according to Example (XXV-1) and 17.7 ml (0.24 mol) of thionyl chloride are stirred at 80° C. until evolution of gas is complete. Excess thionyl chloride is distilled off at 50° C. and the residue is taken up in 100 ml of absolute THF. This solution is added dropwise at 0° C. to 10° C. to a mixture of 20.9 g of methyl 1-amino-3-methyl-cyclohexanecarboxylate in 200 ml of absolute THF and 30.8 ml (0.22 mol) of triethylamine.

For working-up, the solution is filtered off with suction, washed with THF and evaporated, and the residue is taken up in methylene chloride. The solution is washed with 0.5 N HCl, dried and evaporated, and the residue is recrystallized from MTB ether/n-hexane.

Yield: 32.60 g (80% of theory); m.p.: 137° C.

Example (II-2)

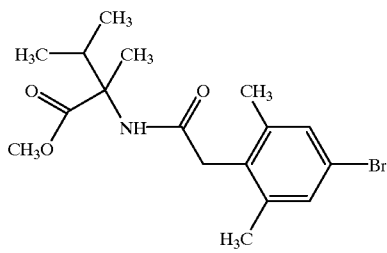

28.8 g of the compound according to Example (XXXI-1) in 170 ml of methylene chloride are added at 30 to 40° C. to 42 g (0.428 mol) of conc. sulphuric acid and the mixture is stirred at this temperature for a further 2 hours. 57 ml of absolute methanol are then added dropwise such that a temperature of 40° C. is established. After addition is complete, the mixture is stirred at 40 to 70° C. for a further 6 hours.

For working-up, it is poured onto ice, extracted with methylene chloride, washed with NaHCO$_3$ solution, dried and evaporated. The crude product is recrystallized from MTB ether/n-hexane.

Yield: 20.7 g (65% of theory); m.p.: 172° C.

The compounds of the formula (II) shown in Table 24 below were prepared analogously to Examples (II-1) and (II-2) or according to the general details for preparation.

TABLE 24

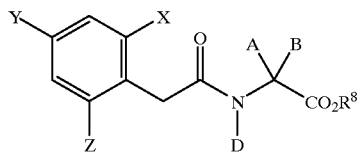

(II)

| Ex. No. | X | Y | Z | B | A | D | R$^8$ | M.p.: ° C. | Isomer |
|---|---|---|---|---|---|---|---|---|---|
| II-3 | CH$_3$ | Br | CH$_3$ | —(CH$_2$)$_2$—CHCH$_3$—(CH$_2$)$_2$— | | H | CH$_3$ | 168 | β |
| II-4 | CH$_3$ | Br | CH$_3$ | —(CH$_2$)$_2$—O—(CH$_2$)$_2$— | | H | CH$_3$ | 162 | — |
| II-5 | C$_2$H$_5$ | Br | CH$_3$ | —(CH$_2$)$_2$—CHCH$_3$—(CH$_2$)$_2$— | | H | CH$_3$ | 129 | β |
| II-6 | CH$_3$ | CH$_3$ | Br | —(CH$_2$)$_2$—CHCH$_3$—(CH$_2$)$_2$— | | H | CH$_3$ | 157 | β |
| II-7 | CH$_3$ | CH$_3$ | Br | —(CH$_2$)$_3$—CHCH$_3$—CH$_2$— | | H | CH$_3$ | 127 | β |
| II-8 | CH$_3$ | CH$_3$ | Br | —(CH$_2$)$_2$—O—(CH$_2$)$_2$— | | H | CH$_3$ | 163 | — |
| II-9 | CH$_3$ | CH$_3$ | Br | CH$_3$ | i-C$_3$H$_7$ | H | CH$_3$ | 183 | — |
| II-10 | CH$_3$ | CH$_3$ | Br | —(CH$_2$)$_2$—CHOCH$_3$—(CH$_2$)$_2$— | | H | CH$_3$ | 146 | β |
| II-11 | CH$_3$ | CH$_3$ | Br | CH$_3$ | CH$_3$ | H | CH$_3$ | 141 | — |
| II-12 | CH$_3$ | CH$_3$ | Br | H | —CH$_2$—CHCH$_3$—CHCH$_3$— | | C$_2$H$_5$ | 46 | trans* |
| II-13 | CH$_3$ | CH$_3$ | Br | H | —CH$_2$—S—(CH$_2$)$_2$— | | C$_2$H$_5$ | oil | — |
| II-14 | CH$_3$ | CH$_3$ | Br | H | H | i-C$_3$H$_7$ | C$_2$H$_5$ | oil | — |
| II-15 | CH$_3$ | CH$_3$ | Br | H | —(CH$_2$)$_4$— | | C$_2$H$_5$ | oil | — |
| II-16 | CH$_3$ | CH$_3$ | Br | H | —CH$_2$—CHCH$_3$—CHCH$_3$ | | C$_2$H$_5$ | oil | cis* |
| II-17 | CH$_3$ | CH$_3$ | Cl | —(CH$_2$)$_2$—CHOCH$_3$—(CH$_2$)$_2$— | | H | CH$_3$ | 45 | β |
| II-18 | CH$_3$ | CH$_3$ | Cl | —(CH$_2$)$_2$—CHCH$_3$—(CH$_2$)$_2$— | | H | CH$_3$ | 110 | β |
| II-19 | CH$_3$ | CH$_3$ | Cl | —(CH$_2$)$_3$—CHCH$_3$—CH$_2$— | | H | CH$_3$ | 40 | β |
| II-20 | CH$_3$ | CH$_3$ | Cl | CH$_3$ | CH$_3$ | H | CH$_3$ | 134 | — |
| II-21 | CH$_3$ | Br | CH$_3$ | —(CH$_2$)$_2$—CHOCH$_3$—(CH$_2$)$_2$ | | H | CH$_3$ | 132 | β |
| II-22 | C$_2$H$_5$ | Br | CH$_3$ | —(CH$_2$)$_2$—O—(CH$_2$)$_2$ | | H | CH$_3$ | 162 | — |
| II-23 | C$_2$H$_5$ | Br | C$_2$H$_5$ | —(CH$_2$)$_2$—CHCH$_3$—(CH$_2$)$_2$ | | H | CH$_3$ | 163 | β |
| II-24 | C$_2$H$_5$ | Br | C$_2$H$_5$ | —(CH$_2$)$_2$—O—(CH$_2$)$_2$ | | H | CH$_3$ | 163 | — |
| II-25 | CH$_3$ | Cl | CH$_3$ | —(CH$_2$)$_2$—CHCH$_3$—(CH$_2$)$_2$ | | H | CH$_3$ | 179 | β |
| II-26 | CH$_3$ | Cl | CH$_3$ | CH$_3$ | CH$_3$ | H | CH$_3$ | 172 | — |
| II-27 | CH$_3$ | CH$_3$ | Cl | —(CH$_2$)$_2$—O—(CH$_2$)$_2$ | | H | CH$_3$ | 148 | — |
| II-28 | CH$_3$ | CH$_3$ | Cl | CH$_3$ | i-C$_3$H$_7$ | H | CH$_3$ | 93 | — |
| II-29 | CH$_3$ | CH$_3$ | Cl | —(CH$_2$)$_2$—CHOCH$_3$—(CH$_2$)$_2$ | | H | CH$_3$ | 138 | β |

Example (XXXI-1)

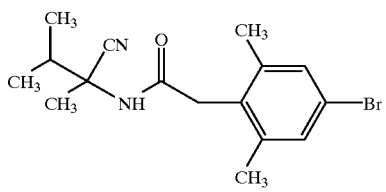

23.1 g of 2,6-dimethyl-4-bromophenylacetic acid according to Example (XXV-1) and 17.7 ml of thionyl chloride are stirred at 80° C. until the evolution of gas is complete. Excess thionyl chloride is then removed in vacuo at 50° C. The residue is taken up in 100 ml of absolute THF and added dropwise at 0 to 10° C. to a mixture of 11.2 g of the amine of the formula $(CH_3)_2CHC(CH_3)(CN)NH_2$ and 14.4 ml (0.11 mol) of triethylamine in 100 ml of absolute THF. It is then stirred at room temperature for a further hour.

For working-up, it is filtered off with suction and concentrated, the residue is taken up in methylene chloride, and the solution is washed in 0.5 N HCl, dried and concentrated. The crude product is recrystallized from MTB ether/n-hexane.

Yield: 28.8 g (85% of theory); m.p.: 169° C.

The compounds of the formula (XXXI) shown in Table 25 below were prepared analogously to Example (XXXI-1).

TABLE 25

(XXXI)

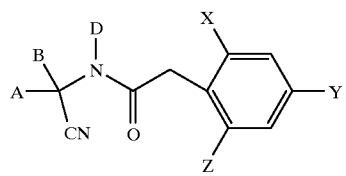

| Ex. No. | X | Y | Z | A | B | D | M.p.: ° C. |
|---|---|---|---|---|---|---|---|
| XXXI-2 | CH₃ | Br | CH₃ | —(CH₂)₂—O—(CH₂)₂— | H | 206 |
| XXXI-3 | CH₃ | CH₃ | Br | —(CH₂)₂—O—(CH₂)₂— | H | 201 |
| XXXI-4 | CH₃ | CH₃ | Br | i-C₃H₇ | CH₃ | H | 139 |
| XXXI-5 | C₂H₅ | Br | CH₃ | —(CH₂)₂—O—(CH₂)₂— | H | 158 |
| XXXI-6 | CH₃ | CH₃ | Cl | —(CH₂)₂—O—(CH₂)₂— | H | 180 |
| XXXI-7 | CH₃ | CH₃ | Cl | i-C₃H₇ | CH₃ | H | 145 |
| XXXI-8 | CH₃ | Cl | CH₃ | —(CH₂)₂—O—(CH₂)₂— | H | 172 |
| XXXI-9 | C₂H₅ | Br | C₂H₅ | —(CH₂)₂—O—(CH₂)₂— | H | 158 |

Example (I-2-a-1)

(I-2-a-1)

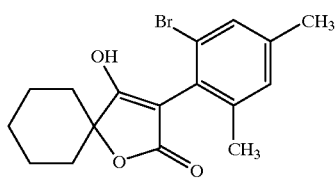

A solution of 19.8 g (50 mmol) of the compound according to Example (III-1) in 50 ml of DMF are added dropwise at 0 to 10° C. to 8.42 g (75 mmol) of potassium tert-butoxide in 50 ml of dimethylformamide (DMF) and the mixture is stirred overnight at room temperature.

For working-up, the reaction mixture is added dropwise to 500 ml of ice-cold 1 N HCl, and the crude product which is precipitated is filtered off with suction, washed with water and dried in a vacuum drying oven. For further purification, the crude product is also boiled with n-hexane/acetone.

Yield: 13.6 g (77% of theory); m.p.: >250° C.

The compounds of the formula (I-2-a) shown in Table 26 below were prepared analogously to Example (I-2-a-1).

TABLE 26

(I-2-a)

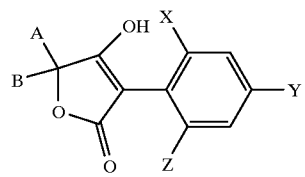

| Ex. No. | X | Y | Z | A | B | M.p.: ° C. |
|---|---|---|---|---|---|---|
| I-2-a-2 | CH₃ | Br | CH₃ | —(CH₂)₅— | | >250 |
| I-2-a-3 | CH₃ | CH₃ | Cl | —(CH₂)₅— | | >240 |
| I-2-a-4 | CH₃ | CH₃ | Cl | —(CH₂)₂—O—(CH₂)₂ | | 239-241 |
| I-2-a-5 | CH₃ | CH₃ | Cl | —(CH₂)₄— | | 268 |
| I-2-a-6 | CH₃ | Cl | CH₃ | —(CH₂)₅— | | 238 |
| I-2-a-7 | CH₃ | Cl | CH₃ | —(CH₂)₂—O—(CH₂)₂ | | 223 |
| I-2-a-8 | CH₃ | Cl | CH₃ | —(CH₂)₄— | | 258 |
| I-2-a-9 | C₂H₅ | Br | CH₃ | —(CH₂)₅— | | 233–234 |
| I-2-a-10 | CH₃ | Br | CH₃ | —(CH₂)₂—O—(CH₂)₂ | | 212–215 |
| I-2-a-11 | CH₃ | Br | CH₃ | —(CH₂)₄— | | 240–242 |
| I-2-a-12 | CH₃ | CH₃ | Br | —(CH₂)₂—O—(CH₂)₂ | | 258–259 |
| I-2-a-13 | CH₃ | CH₃ | Br | —(CH₂)₄— | | 262–263 |

Example (I-2-b-1)

(I-2-b-1)

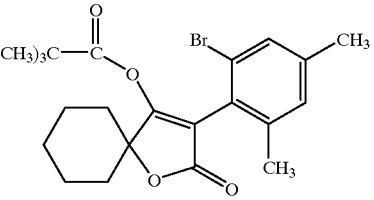

A solution of 1.57 g (13 mmol) of pivaloyl chloride in 40 ml of methylene chloride is added dropwise with ice-cooling to a mixture of 3.52 g (10 mmol) of the compound according to Example (I-2-a-1) and 1.52 g (15 mmol) of triethylamine in 40 ml of methylene chloride and the mixture is stirred at room temperature for 2 hours.

For working up, it is washed successively with 10% strength citric acid, 1 N NaOH and NaCl solution, dried and evaporated. For further purification, the crude product is also stirred with a little petroleum ether.

Yield: 1.95 g (45% of theory); m.p.: 107–109° C.

The compounds of the formula (I-2-b) shown in Table 27 below were prepared analogously to Example (I-2-b-1).

TABLE 27

(I-2-b)

$$\text{Structure (I-2-b)}$$

| Ex. No. | X | Y | Z | A | B | R¹ | M.p.: °C. |
|---|---|---|---|---|---|---|---|
| I-2-b-2 | CH₃ | Br | CH₃ | —(CH₂)₅— | | t-C₄H₉— | 150–152 |
| I-2-b-3 | CH₃ | Br | CH₃ | —(CH₂)₅— | | t-C₄H₉—CH₂— | 158–161 |
| I-2-b-4 | CH₃ | CH₃ | Br | —(CH₂)₅— | | t-C₄H₉—CH₂— | 147–150 |
| I-2-b-5 | CH₃ | CH₃ | Cl | —(CH₂)₅— | | t-C₄H₉— | oil |
| I-2-b-6 | CH₃ | CH₃ | Cl | —(CH₂)₅— | | t-C₄H₉—CH₂— | 160–163 |
| I-2-b-7 | CH₃ | CH₃ | Cl | —(CH₂)₅— | | i-C₄H₉— | 113 |
| I-2-b-8 | CH₃ | CH₃ | Cl | —(CH₂)₂—O—(CH₂)₂— | | t-C₄H₉— | 109–110 |
| I-2-b-9 | CH₃ | CH₃ | Cl | —(CH₂)₄— | | i-C₄H₉— | 90–91 |
| I-2-b-10 | CH₃ | CH₃ | Cl | —(CH₂)₄— | | t-C₄H₉—CH₂— | 106–107 |
| I-2-b-11 | CH₃ | CH₃ | Cl | —(CH₂)₄— | | i-C₃H₇— | 84–85 |
| I-2-b-12 | CH₃ | CH₃ | Cl | —(CH₂)₄— | | t-C₄H₉— | 105–106 |
| I-2-b-13 | CH₃ | Cl | CH₃ | —(CH₂)₅— | | t-C₄H₉— | oil |
| I-2-b-14 | CH₃ | Cl | CH₃ | —(CH₂)₅— | | t-C₄H₉—CH₂— | oil |
| I-2-b-15 | CH₃ | Cl | CH₃ | —(CH₂)₂—O—(CH₂)₂— | | t-C₄H₉— | 148 |
| I-2-b-16 | CH₃ | Cl | CH₃ | —(CH₂)₄— | | i-C₄H₉— | oil |
| I-2-b-17 | CH₃ | Cl | CH₃ | —(CH₂)₄— | | t-C₄H₉—CH₂— | 83 |
| I-2-b-18 | CH₃ | Cl | CH₃ | —(CH₂)₄— | | i-C₃H₇— | oil |
| I-2-b-19 | CH₃ | Cl | CH₃ | —(CH₂)₄— | | t-C₄H₉— | 102 |
| I-2-b-20 | C₂H₅ | Br | CH₃ | —(CH₂)₅— | | t-C₄H₉— | 115–116 |
| I-2-b-21 | C₂H₅ | Br | CH₃ | —(CH₂)₅— | | t-C₄H₉—CH₂— | 139–140 |
| I-2-b-22 | CH₃ | Br | CH₃ | —(CH₂)₂—O—(CH₂)₂— | | t-C₄H₉—CH₂— | 158–159 |
| I-2-b-23 | CH₃ | Br | CH₃ | —(CH₂)₂—O—(CH₂)₂— | | t-C₄H₉— | 148–149 |
| I-2-b-24 | CH₃ | Br | CH₃ | —(CH₂)₄— | | i-C₄H₉— | 84–85 |
| I-2-b-25 | CH₃ | Br | CH₃ | —(CH₂)₄— | | t-C₄H₉—CH₂— | 92–93 |
| I-2-b-26 | CH₃ | Br | CH₃ | —(CH₂)₄— | | i-C₃H₇— | 83–84 |
| I-2-b-27 | CH₃ | Br | CH₃ | —(CH₂)₄— | | t-C₄H₉— | 106–107 |
| I-2-b-28 | CH₃ | CH₃ | Br | —(CH₂)₂—O—(CH₂)₂— | | t-C₄H₉—CH₂— | 126–127 |
| I-2-b-29 | CH₃ | CH₃ | Br | —(CH₂)₂—O—(CH₂)₂— | | t-C₄H₉— | 128–129 |
| I-2-b-30 | CH₃ | CH₃ | Br | —(CH₂)₄— | | i-C₄H₉— | 99–100 |
| I-2-b-31 | CH₃ | CH₃ | Br | —(CH₂)₄— | | t-C₄H₉—CH₂— | 89–90 |
| I-2-b-32 | CH₃ | CH₃ | Br | —(CH₂)₄— | | i-C₃H₇— | 83–84 |
| I-2-b-33 | CH₃ | CH₃ | Br | —(CH₂)₄— | | t-C₄H₉— | 123–124 |
| I-2-b-34 | CH₃ | Cl | CH₃ | —(CH₂)₂—O—(CH₂)₂— | | C₆H₅— | 132–135 |

The compounds of the formula I-2-c shown in Table 28 were obtained analogously to Example I-1-c-1.

TABLE 28

I-2-c $$\text{Structure (I-2-c)}$$

| Ex. No. | X | Y | Z | A | B | L | M | R² | M.p.: °C. |
|---|---|---|---|---|---|---|---|---|---|
| I-2-c-1 | CH₃ | CH₃ | Cl | —(CH₂)₂—O—(CH₂)₂— | | O | O | i-C₃H₇— | oil |
| I-2-c-2 | CH₃ | Br | CH₃ | —(CH₂)₂—O—(CH₂)₂— | | O | O | i-C₃H₇— | 119–120 |

Example (III-1)

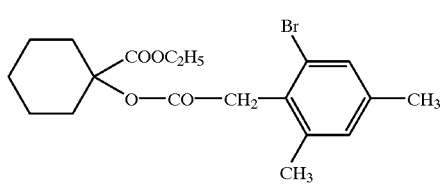

12.15 g (50 mmol) of the compound according to Example (XXV-2) and 11.9 g (100 mmol) of thionyl chloride are stirred in 50 ml of toluene at 80° C. until evolution of gas is complete. The mixture is then evaporated to dryness and the crude acid chloride thus obtained is heated under reflux overnight in 50 ml of toluene together with 8.6 g (50 mmol) of ethyl 1-hydroxycyclohexanecarboxylate. The mixture is then concentrated.

Yield: 19.8 g (quantitative); colourless oil.

$^1$H-NMR: δ=1.20 (t, 3H); 1.40–1.80 (m, 8H); 2.15 (m, 2H); 2.25 (s, 3H); 2.35 (s, 3H); 3.90 (s, 2H); 4.15 (q, 2H); 6.95 (m, 1H); 7.25 (m, 1H).

The compounds of the formula (III) shown in Table 29 are obtained analogously or according to the general details for preparation.

TABLE 29

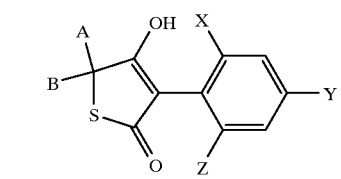

(III)

| Ex. No. | A | B | X | Y | Z | $R^8$ | M.p.: ° C. |
|---|---|---|---|---|---|---|---|
| III-2 | —(CH$_2$)$_5$— | | CH$_3$ | Br | CH$_3$ | C$_2$H$_5$— | oil |
| III-3 | —(CH$_2$)$_5$— | | CH$_3$ | CH$_3$ | Cl | C$_2$H$_5$— | oil |

| Ex. No. | X | Y | Z | A | B | $R^8$ | M.p.: ° C. |
|---|---|---|---|---|---|---|---|
| III-4 | CH$_3$ | Cl | CH$_3$ | —(CH$_2$)$_5$— | | CH$_3$ | oil |
| III-5 | CH$_3$ | CH$_3$ | Cl | —(CH$_2$)$_2$—O—(CH$_2$)$_2$— | CH$_3$ | oil |
| III-6 | CH$_3$ | Br | CH$_3$ | —(CH$_2$)$_2$—O—(CH$_2$)$_2$— | CH$_3$ | oil |
| III-7 | CH$_3$ | CH$_3$ | Br | —(CH$_2$)$_2$—O—(CH$_2$)$_2$— | CH$_3$ | oil |
| III-8 | CH$_3$ | CH$_3$ | Cl | —(CH$_2$)$_2$—O—(CH$_2$)$_2$— | CH$_3$ | oil |
| III-9 | CH$_3$ | CH$_3$ | Br | —(CH$_2$)$_4$— | | CH$_3$ | oil |
| III-10 | CH$_3$ | Br | CH$_3$ | —(CH$_2$)$_4$— | | CH$_3$ | oil |
| III-11 | CH$_3$ | CH$_3$ | Cl | —(CH$_2$)$_4$— | | CH$_3$ | oil |
| III-12 | CH$_3$ | Cl | CH$_3$ | —(CH$_2$)$_4$— | | CH$_3$ | oil |
| III-13 | C$_2$H$_5$ | Br | CH$_3$ | —(CH$_2$)$_5$— | | CH$_3$ | oil |

Example I-3-a-1

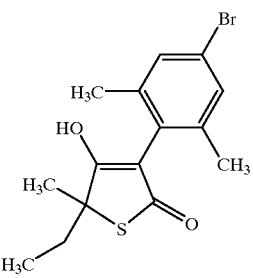

34.0 g (69 mmol) of the compound according to Example (IV-1) are heated under reflux for 3 hours in 70 ml of trifluoroacetic acid and 140 ml of toluene. The trifluoroacetic acid is then removed in vacuo and the residue is treated with 400 ml of water and 120 ml of MTB ether. A pH of 14 is established by addition of NaOH, then the mixture is extracted 2 times with MTB ether. The aqueous phase is acidified with HCl and extracted 3 times with MTB ether. After drying, the organic phase is concentrated. Yield 13.0 g (55% of theory), m.p. 235–238° C.

The compounds of the formula I-3-a shown in Table 30 were prepared analogously to Example I-3-a-1.

TABLE 30

I-3-a

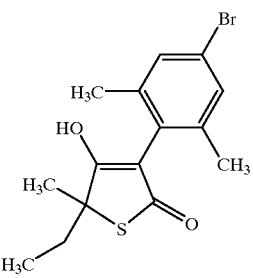

| Ex. No. | X | Y | Z | A | B | M.p.: ° C. |
|---|---|---|---|---|---|---|
| I-3-a-2 | CH$_3$ | Br | CH$_3$ | —(CH$_2$)$_5$— | | 255–257 |
| I-3-a-3 | CH$_3$ | CH$_3$ | Br | —(CH$_2$)$_5$— | | >230 |

Example I-3-b-1

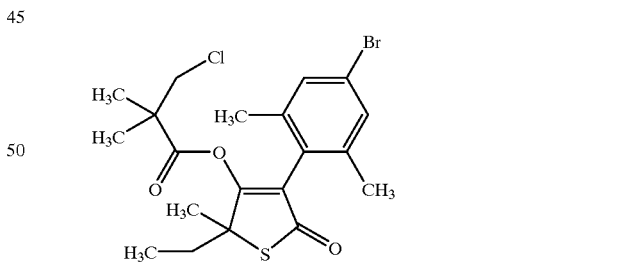

A solution of 0.74 ml (0.89 g; 5.72 mmol) of 3-chloro-2,2-dimethylpropionyl chloride in 3 ml of methylene chloride is added dropwise with ice-cooling to a mixture of 1.5 g (4.4 mmol) of the compound according to Example (I-3-a-1), 0.92 ml of triethylamine and 20 ml of methylene chloride and the mixture is then stirred at room temperature for 2 hours.

It is then washed 2 times with 10% strength citric acid and the acidic aqueous phases are extracted with methylene chloride. The combined organic phases are washed 2 times with 1N NaOH and the aqueous alkaline phases are extracted with methylene chloride. The combined organic phases are dried and concentrated. Yield 1.65 g (81% of theory), oil.

| $^1$H-NMR in CDCl$_3$, ppm | |
|---|---|
| δ = 1.05 | (t, 3H, CH$_2$C<u>H</u>$_3$) |
| 1.18 | (s, 6H, C(C<u>H</u>$_3$)$_2$) |
| 1.62 | (s, 3H, CC<u>H</u>$_3$) |
| 1.95–2.05 | (m, 2H, C<u>H</u>$_2$CH$_3$) |
| 2.08 | (s, 3H, ArC<u>H</u>$_3$) |
| 2.10 | (s, 3H, ArC<u>H</u>$_3$) |
| 3.38 | (s, 2H, C<u>H</u>$_2$Cl) |
| 7.20 | (s, 2H, AR<u>H</u>) |

The compounds of the formula I-3-b shown in Table 31 below were prepared analogously to Example I-3-b-1.

A solution of 0.74 ml (5.72 mmol) of isobutyl chloroformate in 3 ml of methylene chloride is added dropwise with ice-cooling to a mixture of 1.5 g (4.4 mmol) of the compound according to Example (I-3-a-1), 0.92 ml of triethylamine and 20 ml of methylene chloride. The mixture is stirred at room temperature for 2 hours and worked up as described in Example I-3-b-1. The residue remaining at the end is stirred with prtroleum ether. Yeild 2.0 g (100% of theory)

| $^1$H-NMR, CDCl$_3$, [ppm], | |
|---|---|
| δ = 0.68 | (d, 6H, CH(C<u>H</u>$_3$)2) |
| 1.04 | (t, 3H, CH$_2$C<u>H</u>$_3$) |
| 1.5–1.6 | (m, 1H, C<u>H</u>(CH$_3$)$_2$) |

TABLE 31

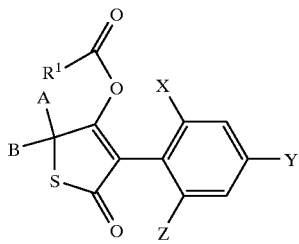

(I-3-b)

| Ex. No. | X | Y | Z | A | B | R$^1$ | M.p.: ° C. |
|---|---|---|---|---|---|---|---|
| I-3-b-2 | CH$_3$ | Br | CH$_3$ | —(CH$_2$)$_5$— | | t-C$_4$H$_9$ | 105–107 |
| I-3-b-3 | CH$_3$ | Br | CH$_3$ | —(CH$_2$)$_5$— | | Cl—CH$_2$—C(CH$_3$)$_2$— | 129–131 |
| I-3-b-4 | CH$_3$ | Br | CH$_3$ | —(CH$_2$)$_5$— | | 3-(6-Cl-Pyridyl)- | 171–173 |
| I-3-b-5 | CH$_3$ | Br | CH$_3$ | —(CH$_2$)$_5$— | | cyclo-C$_3$H$_5$— | 176–180 |
| I-3-b-6 | CH$_3$ | Br | CH$_3$ | C$_2$H$_5$ | CH$_3$ | t-C$_4$H$_9$— | oil |
| I-3-b-7 | CH$_3$ | Br | CH$_3$ | C$_2$H$_5$ | CH$_3$ | cyclo-C$_3$H$_5$— | oil |
| I-3-b-8 | CH$_3$ | CH$_3$ | Br | —(CH$_2$)$_5$— | | t-C$_4$H$_9$— | 81–85 |
| I-3-b-9 | CH$_3$ | CH$_3$ | Br | —(CH$_2$)$_5$— | | 4-Cl—C$_6$H$_4$— | [1] |
| I-3-b-10 | CH$_3$ | CH$_3$ | Br | —(CH$_2$)$_5$— | | ClCH$_2$—C(CH$_3$)$_2$— | 112–116 |
| I-3-b-11 | CH$_3$ | CH$_3$ | Br | —(CH$_2$)$_5$— | | cyclo-C$_3$H$_5$— | oil |

[1])$^1$H-NMR, CDCl$_3$, [ppm], δ = 1.4 to 2.0(m, 10H), 2.15(s, 3H), 2.30(s, 3H), 7.00(s, 1H), 7.30 (s, 1H), 7.42(d, 2H), 7.81(d, 2H).

Example I-3-c-1

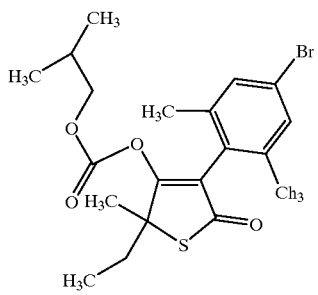

-continued

| $^1$H-NMR, CDCl$_3$, [ppm], | |
|---|---|
| 1.71 | (m, 2H, CC<u>H</u>$_3$) |
| 1.9–2.0 | (m, 2H, C<u>H</u>$_2$CH$_3$) |
| 2.08 | (s, 3H, ArC<u>H</u>$_3$) |
| 2.12 | (s, 3H, ArC<u>H</u>$_3$) |
| 3.61 | (d, 2H, OCH$_2$) |
| 7.12 | (s, 2H, Ar<u>H</u>) |

The compounds of the formula I-3-c shown in Table 32 were prepared analogously to Example I-3-c-1.

TABLE 32

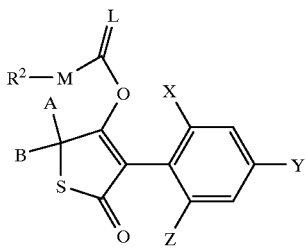

(I-3-c)

| Ex. No. | X | Y | Z | A | B | L | M | R² | M.p.: °C. |
|---|---|---|---|---|---|---|---|---|---|
| I-3-c-2 | CH₃ | Br | CH₃ | —(CH₂)₅— | | O | S | i-C₃H₇— | oil |
| 1-3-c-3 | CH₃ | Br | CH₃ | C₂H₅ | CH₃ | O | O | 4-Cl—C₆H₄— | oil |
| 1-3-c-4 | CH₃ | Br | CH₃ | C₂H₅ | CH₃ | O | S | t-C₄H₉— | oil |
| I-3-c-5 | CH₃ | Br | CH₃ | C₂H₅ | CH₃ | O | S | C₆H₅—CH₂— | oil |
| I-3-c-6 | CH₃ | CH₃ | Br | —(CH₂)₅— | | O | S | i-C₃H₇— | 124–127 |

Example IV-1

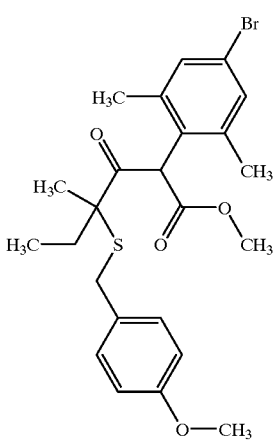

A: A mixture of 25.0 g (98 minol) of the compound of the formula

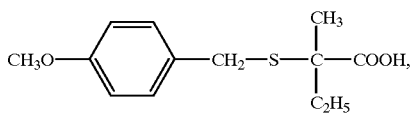

1 drop of DMF and 17.5 g (147 mmol) of thionyl chloride in 70 ml of toluene is stirred at room temperature for 5 minutes and then at 100° C. until the evolution of gas is complete. Excess thionyl chloride is removed in vacuo.

B: 27.7 g of the compound according to Example (XXVI-1) in 40 ml of THF is added dropwise at 0° C. to a mixture of 13.0 g (129 mmol) of diisopropylamine and 71.6 ml (118 mmol) of butyllithium (1.6 M in n-hexane) in 100 ml of THF and the mixture is stirred for 30 minutes. The acid chloride prepared under A, dissolved in 40 ml of THF, is then added dropwise at 0° C. and the mixture is stirred at room temperature for 1 hour.

350 ml of MTB ether and a few drops of water are added, the mixture is washed 2 times with 10% strength ammonium chloride solution, and the organic phase is dried and concentrated. The crude product is chromatographed on silica gel (eluent cyclohexane/ethyl acetate 20:1 to 5:1). Yield 35.0 g (72% of theory).

$^1$H-NMR, CDCl₃, [ppm]; δ=0.9 to 1.0 (m, 3H), 1.43 (s, 3H), 1.7 to 2.0 (m, 2H), 2.3 to 2.4 (s, 6H), 3.5 to 3.8 (m, 8H), 6.7 to 7.2 (m, 6H).

The compounds of the formula IV shown in the table below were obtained analogously to Example IV-1 and according to the general description.

TABLE 33

(IV)

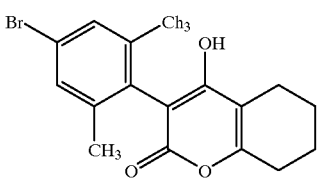

| Ex. No. | X | Y | Z | A B | R⁸ | M.p.: °C. |
|---|---|---|---|---|---|---|
| IV-2 | CH₃ | Br | CH₃ | —(CH₂)₅— | CH₃ | 153 |
| IV-3 | CH₃ | CH₃ | Br | —(CH₂)₅— | CH₃ | 153 |

Example (I-5-a-1)

5.7 g (20 mmol) of 2-(4-bromo-2,6-dimethylphenyl)-chlorocarbonylketene are heated under reflux for 8 h with 2.0 g (20 mmol) of cyclohexanone in 60 ml of xylene. The precipitate which is deposited is separated off, washed with cyclohexane and dried. 5.0 g of product (72% of theory) of melting point 244 to 245° C. are obtained.

The following compounds of the formula (I-5-a) are obtained analogously or according to the general details for preparation:

TABLE 34

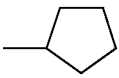

(I-5a)

| Ex. No. | X | Y | Z | A | D | M.p. [° C.]- $^1$H-NMR (CDCl$_3$): δ [ppm] |
|---|---|---|---|---|---|---|
| I-5-a-2 | CH$_3$ | CH$_3$ | Br | CH$_3$ | 4-F-Phenyl | oil |
| I-5-a-3 | CH$_3$ | Br | CH$_3$ | CH$_3$ | t-Bu | 219–221 |
| I-5-a-4 | CH$_3$ | CH$_3$ | Br | CH$_3$ | 2-Pyridyl | 262–264 |
| I-5-a-5 | CH$_3$ | Br | CH$_3$ | CH$_3$ | 4-F-Phenyl | 210–211 |
| I-5-a-6 | CH$_3$ | Br | CH$_3$ | CH$_3$ | 2-Pyridyl | 104–106 |
| I-5-a-7 | CH$_3$ | Br | CH$_3$ | CH$_3$ | cyclopentyl | 206–208 |
| I-5-a-8 | CH$_3$ | CH$_3$ | Br | CH$_3$ | t-Bu | 7.37(1H, s), 7.07 (1H, s), 2.3(3H, s), 2.18(3H, s), 2.15 (3H, s), 1.49(9H, s) |
| I-5-a-9 | CH$_3$ | CH$_3$ | Br |  | —(CH$_2$)$_4$— | 250–252 |
| I-5-a-10 | CH$_3$ | CH$_3$ | Cl | CH$_3$ | 2-Pyridyl | 197–199 |
| I-5-a-11 | CH$_3$ | CH$_3$ | Cl | CH$_3$ | 4-F-Phenyl | 188–190 |

Example (I-5-b-1)

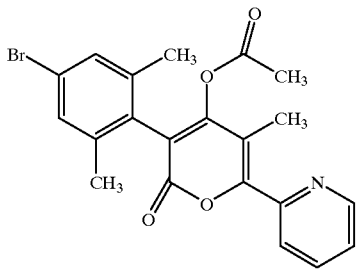

1.9 g (5 mmol) of the compound (I-5-a-6) are initially introduced into 20 ml of ethyl acetate and treated with 0.5 g (5 mmol) of triethylamine, and 0.4 g (5 mmol) of acetyl chloride in 5 ml of ethyl acetate is added dropwise at 0° C. The mixture is stirred at room temperature for 20 h, and the precipitate is separated off, washed twice with 50 ml of half-concentrated sodium chloride solution, dried over sodium sulphate and evaporated in vacuo. The residue is chromatographed on silica gel using toluene/acetone 30:1.

Yield 1.2 g (56% of theory) of melting point 130 to 132° C.

Example (I-6-a-1)

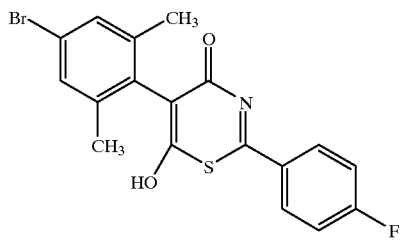

2.8 g (10 mmol) of 2-(4-bromo-2,6-dimethylphenyl)-chlorocarbonyl ketene are warmed to 50° C. for 6 h with 1.6 g (10 mmol) of 4-fluorothiobenzamide in 80 ml of toluene. The precipitate is separated off, washed with cyclohexane and dried. 3.0 g (74% of theory) of melting point 275 to 276° C. are obtained.

The following compound of the formula (I-6-a-2) of melting point 235 to 236° C. is obtained analogously or according to the general details for preparation.

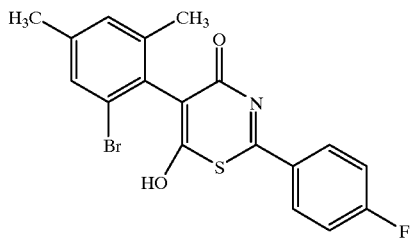

(I-6-a-2)

Example (XXII-1)

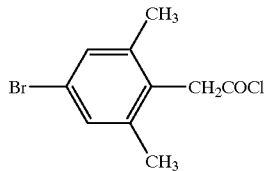

(XXII-1)

8 g of the compound according to Example (XXV-1) are heated at 80° C. with 8.7 ml of thionyl chloride until the evolution of gas is complete. Excess thionyl chloride is removed in vacuo and the residue is distilled.

Yield: 87% of theory; m.p.: 69–71° C.

The following compounds of the formula (XXII) are obtained analogously or according to the general details for preparation.

TABLE 35

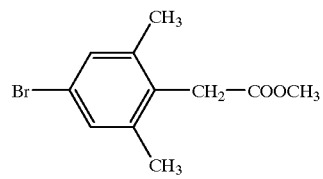
(XXII)

| Ex. No. | X | Y | Z | B.p. [° C.], (mbar) |
|---|---|---|---|---|
| XXII-2 | CH₃ | CH₃ | Br | 114–116, 0.06 |
| XXII-3 | CH₃ | Br | C₂H₅ | 120–132, 0.1 |
| XXII-4 | CH₃ | CH₃ | Cl | * |
| XXII-5 | CH₃ | Cl | CH₃ | * |
| XXII-6 | C₂H₅ | Br | C₂H₅ | 131, 0.15 |

*These acid chlorides were used as crude products for the syntheses of the compounds II, III and XXXI and were not characterized in greater detail.

Example (XXXV-1)

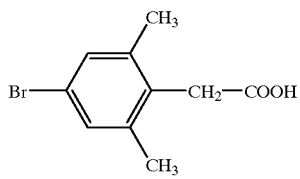
(XXV-1)

222.4 g (0.865 mol) of the compound according to Example (XXVI-1) and 80.56 g (1.438 mol) of potassium hydroxide in 210 ml of methanol and 105 ml of water are heated under reflux for 5 hours. After cooling, the mixture is concentrated and the residue is dissolved in water. The aqueous phase is washed with ethyl acetate and then with dilute hydrochloric acid. The product which is deposited is filtered off with suction, washed with water and dried.

Yield: 197.5 g (94% of theory); m.p.: 185–187° C.

The compounds of the formula (XXV) shown in Table 36 are obtained analogously or according to the general details for preparation.

TABLE 36

(XXV)

| Ex. No. | X | Y | Z | M.p. [° C.] |
|---|---|---|---|---|
| XXV-2 | CH₃ | CH₃ | Br | 174–176 |
| XXV-3 | C₂H₅ | Br | CH₃ | 122–123 |
| XXV-4 | CH₃ | CH₃ | Cl | 166–168 |
| XXV-5 | CH₃ | Cl | CH₃ | 178–180 |
| XXV-6 | C₂H₅ | Br | C₂H₅ | 143 |

Example (XXVI-1)

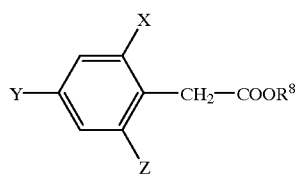
(XXVI-1)

349.3 g (1.044 mol) of the compound according to Example (XXVII-1) (94.57% strength), 475 ml of methanol and 842 ml of 30% strength sodium methoxide solution in methanol are heated under reflux for 5 hours. 126 ml of conc. sulphuric acid are then added at room temperature and the mixture is heated under reflux for 1 hour. The solvent is distilled off, and the residue is treated with water and extracted with methylene chloride. After drying, it is filtered, concentrated and finally distilled.

Yield: 222.4 g (82.9% of theory); b.p.$_{0.2}$ 98–100° C.

The following compounds of the formula (XXVI) are obtained analogously or according to the general procedures for preparation.

TABLE 37

(XXVI)

| Ex. No. | X | Y | Z | R⁸ | B.p. [° C.], (mbar) |
|---|---|---|---|---|---|
| XXVI-2 | CH₃ | CH₃ | Br | CH₃ | 93–94, 0.2 |
| XXVI-3 | CH₃ | Br | C₂H₅ | CH₃ | 160–165, 20 |
| XXVI-4 | CH₃ | CH₃ | Cl | CH₃ | oil |
| XXVI-5 | CH₃ | Cl | CH₃ | CH₃ | 152–158, 16 |
| XXVI-6 | C₂H₅ | Br | C₂H₅ | CH₃ | 90–95, 0.015 |

Example (XXVII-1)

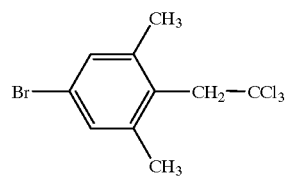
(XXVII-1)

326 g (2.673 mol) of anhydrous copper(II) chloride are added to a solution of 326 g (3.175 mol) of tert-butyl nitrite in 1270 ml of dry acetonitrile. 3130 g (32.27 mol =2580 ml) of 1,1-dichloroethane are added dropwise to the well-cooled mixture, the mixture being kept at below 30° C. by means of ice-cooling. A solution of 424 g (2.12 mol) of 4-bromo-2,6-dimethylaniline in 2120 ml of acetonitrile is then added dropwise at below 30° C. The mixture is stirred at room temperature until the evolution of gas (N₂) is complete (about 3 hours). The almost black solution is carefully poured into 9 l of 20% strength hydrochloric acid and extracted several times, altogether with 9 l, of methyl tert-butyl ether. The combined organic phases are washed with 20% strength hydrochloric acid and dried over anhydrous magnesium sulphate. The magnesium sulphate is filtered off and the solution is concentrated. The residual oil is fractionated in a high vacuum.

Yield: 349.3 g (49% of theory); b.p.$_{\cdot 0.1}$ 130–137° C.

The following compounds of the formula (XXVII) were prepared analogously or according to the general details for preparation:

TABLE 38

(XXVII)

Y—⟨benzene ring with X, Z substituents⟩—CH$_2$—CCl$_3$

| Ex. No. | X | Y | Z | B.p. [° C.], (mbar) |
|---|---|---|---|---|
| XXVII-2 | CH$_3$ | CH$_3$ | Br | 110–115, 0.15 |
| XXVII-3 | CH$_3$ | Br | C$_2$H$_5$ | oil |
| XXVII-4 | CH$_3$ | CH$_3$ | Cl | oil |
| XXVII-5 | CH$_3$ | Cl | CH$_3$ | oil |
| XXVII-6 | C$_2$H$_5$ | Br | C$_2$H$_5$ | oil |

Example VI-1

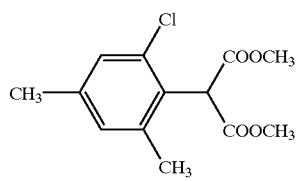
(VI-1)

7.1 g of NaH (80% strength) were initially introduced into 278 ml of dimethyl carbonate and heated to 80 to 90° C. 39 g of methyl 2-chloro-4,6-dimethylphenylacetate were then added dropwise and the mixture was heated at reflux for 20 h. A further 3.4 g of NaH (80% strength) were added and the mixture was heated at reflux for a further 8 h. The mixture was cooled, any NaH still present was destroyed with a little methanol, and it was poured onto ice. After acidifying with half-concentrated HCl, the organic phase was separated off and the aqueous phase was extracted several times with dichloromethane. The combined organic phase was dried and concentrated. Yield: 35.1 g of a solid having a melting point of 67 to 70° C.

$^1$H-NMR (CDCl$_3$): δ 7.12 (s, 1H), 6.94 (s, 1H), 5.36 (2, 1H), 3.78 (s, 6H), 2.31 (s, 3H), 2.28 ppm (s, 3H).

Example XXXV-1

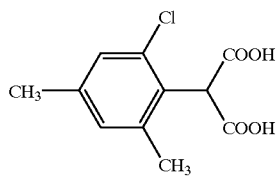

10 g of dimethyl 2-chloro-4,6-dimethylphenylmalonate according to Example (VI-1) were initially introduced and treated successively with 20 ml of methanol and 6.8 g of KOH dissolved in 9.1 ml of water. After an hour, the mixture was diluted with a further 20 ml of solvent (MeOH/water 1:1). The mixture was heated at reflux for 10 h, then cooled and concentrated. The residue which remained was taken up in a little water and washed once with toluene. The aqueous phase was then diluted further with water, added to the same amount of ether and cooled to about –10° C. It was acidified with concentrated HCl (pH 1), and the organic phase was separated off and reextracted a further 1 or 2 times. The combined organic phases were dried and concentrated. The residue was crystallized from toluene and afforded 7.6 g of 2-chloro-4,6-dimethylphenylmalonic acid having a melting point of 174 to 176° C. (decomposition).

$^1$H-NMR (CDCl$_3$) δ: 7.10 (s, 1H), 6.95 (s, 1H), 5.00 (s, 1H), 2.36 (s, 3H), 2.30 ppm (s, 3H).

Example V-1

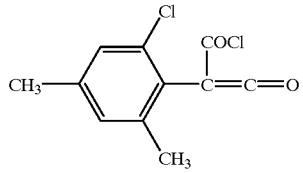
(V-1)

7.6 g of 2-chloro-4,6-dimethylphenylmalonic acid according to Example (XXXV-1) were suspended in 22 ml of toluene and treated dropwise with 19.5 ml of thionyl chloride. The mixture was heated at 95° C. for 9.5 h, cooled and freed from the volatile constituents by passing argon through. The residues of thionyl chloride and the solvent were distilled off at 45° C. in a high vacuum. 6.6 g of 2-chloro-4,6-dimethylphenylchlorocarbonylketene were obtained as an oil which was slightly contaminated with 2-chloro-4,6-dimethylphenylacetyl chloride.

$^1$H-NMR (CDCl$_3$) δ: 7.16 (s, 1H), 7.02 (s, 1H), 2.33 (s, 3H), 2.30 ppm, (s, 3H).

Example (VI-2)

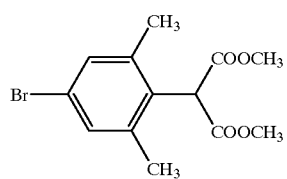
(VI-2)

70 g of methyl 4-bromo-2,6-dimethylphenylacetate were reacted in an analogous manner with 26.8 g of NaH and 7.39 ml of dimethyl carbonate. After working up, 95.4 g of crude product (86.5% pure) were obtained.

$^1$H-NMR (CDCl$_3$) δ: 7.22 (s, 2H), 5.00 (s, 4H), 3.75 (s, 6H), 2.33 ppm (s, 6H).

Example (XXXV-2)

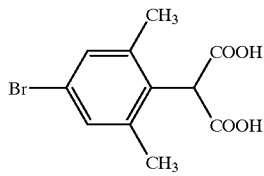
(XXXV-2)

85 g of dimethyl 4-bromo-2,6-dimethylphenylmalonate according to Example (VI-2) in 158 ml of methanol were reacted in an analogous manner with 49.6 g of KOH in 66 ml of H$_2$O. After working up, 59.7 g of the malonic acid were obtained. Melting point 164 to 167° C. (decomposition).

$^1$H-NMR (CDCl$_3$) δ: 7.20 (s, 2H), 7.00–6.00 (OH), 4.83 (s, 1H), 2.30 ppm (s, 6H).

Example (V-2)

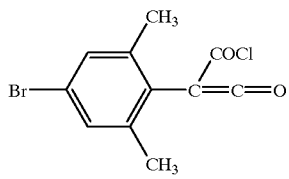
(V-2)

59 g of 4-bromo-2,6-dimethylphenylmalonic acid in 143 ml of toluene were reacted in an analogous manner with 128 ml of thionyl chloride and 49.5 g were isolated as a crude product.

$^1$H-NMR (CDCl$_3$) δ: 7.31 (s, 2H), 2.33 ppm (s, 6H).

Example (VI-3)

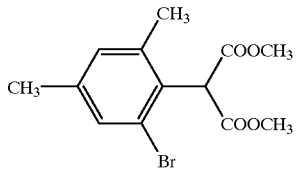
(VI-3)

23 g of methyl 2-bromo-4,6-dimethylphenylacetate were reacted in an analogous manner with 9.5 g of NaH (80% strength) and 242 ml of dimethyl carbonate. After working up, 31.2 g of crude product (82% pure) were obtained.

$^1$H-NMR (CDCl$_3$) δ: 7.31 (s, 1H), 6.98 (s, 1H), 5.45 (s, 1H), 3.88 (s, 6H), 2.32 (s, 3H), 2.28 ppm (s, 3H).

Example (XXXV-3)

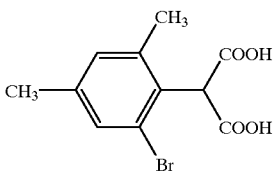
(XXXV-3)

27 g of dimethyl 2-bromo-4,6-dimethylphenylmalonate according to Example (VI-3) in 50 ml of methanol were reacted in an analogous manner with 15.7 g of KOH in 21 ml of water. After working up, 17.4 g of malonic acid were obtained. Melting point 167 to 169° C. (decomposition).

$^1$H-NMR (CDCl$_3$) δ: 8.20–7.00 (OH), 7.26 (s, 1H), 6.98 (s, 1H), 5.07 (s, 1H), 2.35 (s, 3H), 2.28 ppm (s, 3H).

Example (V-3)

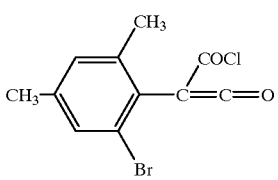
(V-3)

17 g of 2-bromo-4,6-dimethylphenylmalonic acid according to Example (XXXV-3) in 41 ml of toluene were reacted in an analogous manner with 36.8 ml of thionyl chloride and 15.1 g were isolated as a crude product. IR: $\mu$=2130 (ketene)

$^1$H-NMR (CDCl$_3$) δ: 7.28 (s, 1H), 7.00 (s, 1H), 2.35 (s, 3H), 2.29 ppm (s, 3H).

USE EXAMPLES

Example A

Phaedon Larvae Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of the active compound of the desired concentration and are infested with mustard beetle larvae (Phaedon cochleariae), while the leaves are still moist.

After 3 days in each case, the destruction in % is determined. 100% means that all the beetle larvae have been killed; 0% means that none of the beetle larvae have been killed.

In this test, for example, the compounds according to Preparation Examples (I-2-a-2), (I-2-b-2), (I-2-a-1), (I-2-b-1), (I-2-b-4), (I-1-a-2), (I-1-a-1), (I-1-b-2) and (I-1-b-4) at an exemplary active compound concentration of 0.1% caused a destruction of 100% after 7 days.

Example B

Plutella Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated by being dipped into the preparation of the active compound of the desired concentration and are infested with caterpillars of the diamond-back moth (Plutella xylostella) while the leaves are still moist.

After the specified period of time, the destruction in % is determined. 100% means that all the caterpillars have been killed; 0% means that none of the caterpillars have been killed.

In this test, for example, the compounds according to Preparation Examples (I-2-b-2), (I-2-b-1), (I-1-b-2), (I-1-b-4), (I-1-c-2), (I-1-a-5) and (I-1-1-6) at an exemplary active compound concentration of 0.1% caused a destruction of 100% after 7 days.

Example C

Nephotettix Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (Oryza sativa) are treated by being dipped into the preparation of the active compound of the desired concentration and are infested with the green rice leafhopper (Nephotettix cinciceps) while the leaves are still moist.

After the specified period of time, the destruction in % is determined. 100% means that all the leafhoppers have been killed; 0% means that none of the leafhoppers have been killed.

In this test, for example, the compounds according to Preparation Examples (I-2-a-2), (I-2-a-1), (I-2-b-1), (I-1-a-2), (I-1-a-1), (I-1-b-2), (I-1-b-3), (I-1-b-4), (I-1-c-2), (I-1-a-5) and (I-1-a-6) at an exemplary active compound concentration of 0.1% caused a destruction of 100% after 6 days.

Example D

Myzus Test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) which have been heavily infested with the peach aphid (Myzus persicae) are treated by being dipped into the preparation of the active compound of the desired concentration.

After the specified period of time, the destruction in % is determined. 100% means that all the aphids have been killed; 0% means that none of the aphids have been killed.

In this test, for example, the compounds according to Preparation Examples (I-2-a-1), (I-2-a-2), (I-2-b-2), (I-1-b-3), (I-1-c-2) and (I-1-a-6) at an exemplary active compound concentration of 0.1% caused a destruction of 100% after 6 days.

Example E

Tetranychus Test (OP-resistant/dipping treatment)

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (Phaseolus vulgaris) which have been heavily infested with the common spider mite or two-spotted spider mite (Tetranychus urticae) in all stages of development are treated by being dipped into the preparation of the active compound of the desired concentration.

After the specified period of time, the destruction in % is determined. 100% means that all the spider mites have been killed; 0% means that none of the spider mites have been killed.

In this test, for example, the compounds according to Preparation Examples (I-2-a-2), (I-2-b-2), (I-2-b-3), (I-2-a-1) and (I-2-b-4) at an exemplary active compound concentration of 0.1% had an action of 100% after 13 days.

Example F

Pre-emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added, and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

| | | Pre-emergence test/greenhouse | | | | |
|---|---|---|---|---|---|---|
| Ex. No. | g/ha | Beta vulgaris | Alopecurus myosuroides | Avena fatua | Setaria viridis | Sinapis arvensis l. |
| I-1-a-2 | 250 | 0 | 100 | 60 | 100 | 90 |
| I-1-b-2 | 250 | 0 | 100 | 100 | 100 | — |
| I-1-b-3 | 250 | 0 | — | 80 | 100 | 95 |
| I-1-b-4 | 250 | 0 | — | 100 | 100 | 95 |
| I-1-c-2 | 250 | 0 | 95 | 80 | 100 | 100 |
| I-1-a-5 | 250 | — | 100 | 100 | 100 | 100 |
| I-1-a-6 | 250 | — | 95 | 95 | 10 | 100 |

What is claimed is:

1. Compounds of the formula (I)

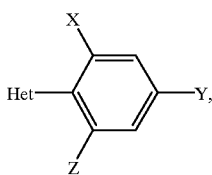

(I)

in which
X represents alkyl,
Y represents halogen or alkyl and
Z represents halogen or alkyl,
with the proviso that one of the radicals Y and Z always represents halogen and the other alkyl,
Het represents one of the groups

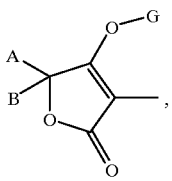

(2)

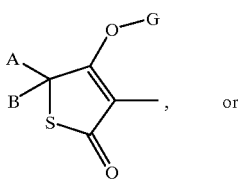

(3)

or

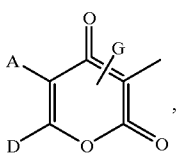

(5)

in which
A represents hydrogen, or alkyl, alkenyl, alkoxyalkyl, polyalkoxyalkyl or alkylthioalkyl, each of which is optionally substituted by halogen, or cycloalkyl or heterocyclyl, each of which is saturated or unsaturated and optionally substituted, or aryl, arylalkyl or hetaryl, each of which is optionally substituted by halogen, alkyl, halogenoalkyl, alkoxy, halogenoalkoxy, cyano or nitro,
B represents hydrogen, alkyl or alkoxyalkyl, or
A and B, together with the carbon atom to which they are bonded, represent a saturated or unsaturated, optionally substituted carbocycle or heterocycle,
D represents hydrogen or an optionally substituted radical of the series alkyl, alkenyl, alkinyl, alkoxyalkyl, polyalkoxyalkyl, alkylthioalkyl, saturated or unsaturated cycloalkyl, saturated or unsaturated heterocyclyl, arylalkyl, aryl, hetarylalkyl or hetaryl, or
A and D, together with the atoms to which they are bonded, represent a saturated or unsaturated and optionally substituted carbocycle or heterocycle, G, in the case in which Het represents one of the radicals (2), (3), or (5) represents hydrogen (a) or, in the case in which Het represents one of the radicals (2), (3), or (5), represents one of the groups

(b)

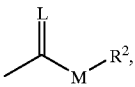

(c)

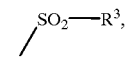

(d)

(e)

E or (f)

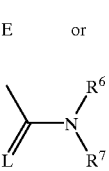

(g)

in which
E represents a metal ion equivalent or an ammonium ion,
L represents oxygen or sulphur,
M represents oxygen or sulphur,
$R^1$ represents alkyl, alkenyl, alkoxyalkyl, alkylthioalkyl or polyalkoxyalkyl, each of which is optionally substituted by halogen, or cycloalkyl or heterocyclyl, each of which is optionally substituted by halogen, alkyl or alkoxy, or phenyl, phenylalkyl, hetaryl, phenoxyalkyl or hetaryloxyalkyl, each of which is optionally substituted,
$R^2$ represents alkyl, alkenyl, alkoxyalkyl or polyalkoxyalkyl, each of which is optionally substituted by halogen, or cycloalkyl, phenyl or benzyl, each of which is optionally substituted,
$R^3$, $R^4$ and $R^5$ independently of one another represent alkyl, alkoxy, alkylamino, dialkylamino, alkylthio, alkenylthio or cycloalkylthio, each of which is optionally substituted by halogen, or phenyl, phenoxy or phenylthio, each of which is optionally substituted,
$R^6$ and $R^7$ independently of one another represent hydrogen, or alkyl, cycloalkyl, alkenyl, alkoxy, alkoxyalkyl, each of which is optionally substituted by halogen, or phenyl or benzyl, each of which is optionally substituted, or, together with the N atom to which they are bonded, form an optionally substituted cyclic system optionally containing oxygen or sulphur.

2. Compounds of the formula (I) according to claim 1, in which
X represents $C_1$–$C_6$-alkyl,
Y represents halogen or $C_1$–$C_6$-alkyl,
Z represents halogen or $C_1$–$C_6$-alkyl,
in this case, one of the substituents Y and Z always represents halogen and the other alkyl, Het represents one of the groups

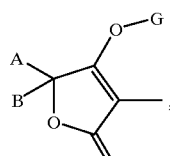
(2)

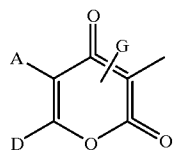
(3)

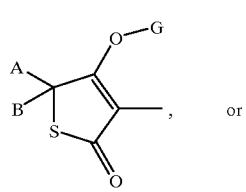
(5)

A represents hydrogen, or $C_1$–$C_{12}$-alkyl, $C_2$–$C_8$-alkenyl, $C_1$–$C_{10}$-alkoxy-$C_1$–$C_8$-alkyl, poly-$C_1$–$C_8$-alkoxy-$C_1$–$C_8$-alkyl or $C_1$–$C_{10}$-alkylthio-$C_1$–$C_6$-alkyl, each of which is optionally substituted by halogen, or $C_3$–$C_8$-cycloalkyl which is optionally substituted by halogen, $C_1$–$C_6$-alkyl or $C_1$–$C_6$-alkoxy and in which one or two methylene groups are optionally replaced by oxygen and/or sulphur, or phenyl, naphthyl, phenyl-$C_1$–$C_6$-alkyl, naphthyl-$C_1$–$C_6$-alkyl or hetaryl having 5 or 6 ring atoms and one to three heteroatoms from the series oxygen, sulphur and nitrogen, each of which is optionally substituted by halogen, $C_1$–$C_6$-alkyl, $C_1$–$C_6$-halogenoalkyl, $C_1$–$C_6$-alkoxy, $C_1$–$C_6$-halogenoalkoxy, cyano or nitro B represents hydrogen, $C_1$–$C_{12}$-alkyl or $C_1$–$C_8$-alkoxy-$C_1$–$C_6$-alkyl, or A, B and the carbon atom to which they are bonded represent $C_3$–$C_{10}$-cycloalkyl or $C_5$–$C_{10}$-cycloalkenyl, in which one methylene group is optionally replaced by oxygen or sulphur and each of which is optionally substituted by $C_1$–$C_8$-alkyl, $C_3$–$C_{10}$-cycloalkyl, $C_1$–$C_8$-halogenoalkyl, $C_1$–$C_8$-alkoxy, $C_1$–$C_8$-alkylthio, halogen or phenyl or A, B and the carbon atom to which they are bonded represent $C_5$–$C_6$-cycloalkyl which is substituted by an alkylenediyl group optionally containing one or two oxygen and/or sulphur atoms, or by an alkylenedioxyl group or by an alkylenedithioyl group which, with the carbon atom to which it is bonded, forms a further five- to eight-membered ring, or A, B and the carbon atom to which they are bonded represent $C_3$–$C_8$-cycloalkyl or $C_5$–$C_8$-cycloalkenyl, in which two substituents, together with the carbon atoms to which they are bonded, represent $C_3$–$C_6$-alkanediyl, $C_3$–$C_6$-alkenediyl or $C_4$–$C_6$-alkanedienediyl, each of which is optionally substituted by $C_1$–$C_6$-alkyl, $C_1$–$C_6$-alkoxy or halogen and in which one methylene group is optionally replaced by oxygen or sulphur in each case, D represents hydrogen, or $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, poly-$C_1$–$C_8$-alkoxy-$C_2$–$C_8$-alkyl or $C_1$–$C_{10}$-alkylthio-$C_2$–$C_8$-alkyl, each of which is optionally substituted by halogen, or $C_3$–$C_8$-cycloalkyl which is optionally substituted by halogen, $C_1$–$C_4$-alkyl, $C_1$–$C_4$-alkoxy or $C_1$–$C_4$-halogenoalkyl and in which one or two non-directly adjacent methylene groups are optionally replaced by oxygen and/or sulphur, or phenyl, hetaryl having 5 to 6 ring atoms and one or two heteroatoms from the series oxygen, sulphur and nitrogen, phenyl-$C_1$–$C_6$-alkyl or hetaryl-$C_1$–$C_6$-alkyl having 5 to 6 ring atoms and one or two heteroatoms from the series oxygen, sulphur and nitrogen, each of which is optionally substituted by halogen, $C_1$–$C_6$-alkyl, $C_1$–$C_6$-halogenoalkyl, $C_1$–$C_6$-alkoxy, $C_1$–$C_6$-halogenoalkoxy, cyano or nitro, or A and D together represent a $C_3$–$C_6$-alkanediyl, $C_3$–$C_6$-alkenediyl or $C_4$–$C_6$-alkadienediyl group, in which one methylene group in each case is optionally replaced by oxygen or sulphur and each of which is optionally substituted by halogen, hydroxyl, mercapto or $C_1$–$C_{10}$-alkyl, $C_1$–$C_6$-alkoxy, $C_1$–$C_6$-alkylthio, $C_3$–$C_7$-cycloalkyl, phenyl or benzyloxy, each of which is optionally substituted by halogen, or by a further $C_3$–$C_6$-alkanediyl, $C_3$–$C_6$-alkenediyl or $C_4$–$C_6$-alkadienediyl group forming a fused ring and in which one methylene group in each case is optionally replaced by oxygen or sulphur and which is optionally substituted by $C_1$–$C_6$-alkyl or in which two adjacent substituents, together with the carbon atoms to which they are bonded, optionally form a further saturated or unsaturated carbocycle having 5 or 6 ring atoms, or A and D together represent a $C_3$–$C_6$-alkanediyl or $C_3$–$C_6$-alkenediyl group which in each case optionally contains one of the following groups

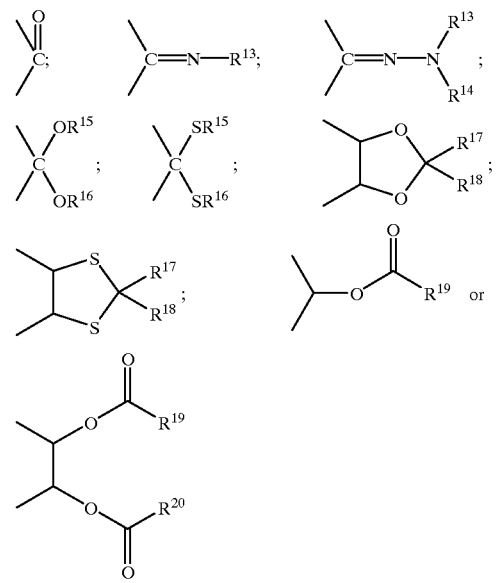

G represents, in the case in which Het represents one of the radicals (2), (3), or (5) hydrogen (a) or, in the case in which Het represents one of the radicals (2), (3), or (5), one of the groups (b)
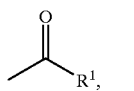

(c)
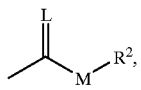

(d)
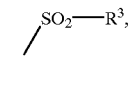

(e)
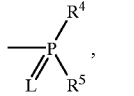

(f)
E   or (g)
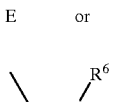

in which

E represents a metal ion equivalent or an ammonium ion,

L represents oxygen or sulphur and

M represents oxygen or sulphur, $R^1$ represents $C_1-C_{20}$-alkyl, $C_2-C_{20}$-alkenyl, $C_1-C_8$-alkoxy-$C_1-C_8$-alkyl, $C_1-C_8$-alkylthio-$C_1-C_8$-alkyl or poly-$C_1-C_8$-alkoxy-$C_1-C_8$-alkyl, each of which is optionally substituted by halogen, or $C_3-C_8$-cycloalkyl which is optionally substituted by halogen, $C_1-C_6$-alkyl or $C_1-C_6$-alkoxy and in which one or two methylene groups are optionally replaced by oxygen and/or sulphur, phenyl which is optionally substituted by halogen, cyano, nitro, $C_1-C_6$-alkyl, $C_1-C_6$-alkoxy, $C_1-C_6$-halogenoalkyl, $C_1-C_6$-halogenoalkoxy, $C_1-C_6$-alkylthio or $C_1-C_6$-alkylsulphonyl, phenyl-$C_1-C_6$-alkyl which is optionally substituted by halogen, nitro, cyano, $C_1-C_6$-alkyl, $C_1-C_6$-alkoxy, $C_1-C_6$-halogenoalkyl or $C_1-C_6$-halogenoalkoxy, 5- or 6-membered hetaryl having one or two heteroatoms from the series oxygen, sulphur and nitrogen and which is optionally substituted by halogen or $C_1-C_6$-alkyl, phenoxy-$C_1-C_6$-alkyl which is optionally substituted by halogen or $C_1-C_6$-alkyl, or 5- or 6-membered hetaryloxy-$C_1-C_6$-alkyl having one or two hdteroatoms from the series oxygen, sulphur and nitrogen and which is optionally substituted by halogen, amino or $C_1-C_6$-alkyl, $R^2$ represents $C_1-C_{20}$-alkyl, $C_2-C_{20}$-alkenyl, $C_1-C_8$-alkoxy-$C_2-C_8$-alkyl or poly-$C_1-C_8$-alkoxy-$C_2-C_8$-alkyl, each of which is optionally substituted by halogen, $C_3-C_8$-cycloalkyl which is optionally substituted by halogen, $C_1-C_6$-alkyl or $C_1-C_6$-alkoxy, or phenyl or benzyl, each of which is optionally substituted by halogen, cyano, nitro, $C_1-C_6$-alkyl, $C_1-C_6$-alkoxy, $C_1-C_6$-halogenoalkyl or $C_1-C_6$-halogenoalkoxy, $R^3$ represents $C_1-C_8$-alkyl which is optionally substituted by halogen, or phenyl or benzyl, each of which is optionally substituted by halogen, $C_1-C_6$-alkyl, $C_1-C_6$-alkoxy, $C_1-C_4$-halogenoalkyl, $C_1-C_4$-halogenoalkoxy, cyano or nitro, $R^4$ and $R^5$ independently of one another represent $C_1-C_8$-alkyl, $C_1-C_8$-alkoxy, $C_1-C_8$-alkylamino, di-($C_1-C_8$-alkyl)amino, $C_1-C_8$-alkylthio or $C_2-C_8$-alkenylthio, each of which is optionally substituted by halogen, or phenyl, phenoxy or phenylthio, each of which is optionally substituted by halogen, nitro, cyano, $C_1-C_4$-alkoxy, $C_1-C_4$-halogenoalkoxy, $C_1-C_4$-alkylthio, $C_1-C_4$-halogenoalkylthio, $C_1-C_4$-alkyl or $C_1-C_4$-halogenoalkyl, $R^6$ and $R^7$ independently of one another represent hydrogen, or $C_1-C_8$-alkyl, $C_3-C_8$-cycloalkyl, $C_1-C_8$-alkoxy, $C_3-C_8$-alkenyl or $C_1-C_8$-alkoxy-$C_2-C_8$-alkyl, each of which is optionally substituted by halogen, or phenyl or benzyl, each of which is optionally substituted by halogen, $C_1-C_8$-alkyl, $C_1-C_8$-halogenoalkyl or $C_1-C_8$-alkoxy or together represent a $C_3-C_6$-alkylene radical which is optionally substituted by $C_1-C_6$-alkyl and in which a methylene group is optionally replaced by oxygen or sulphur, $R^{13}$ represents hydrogen or $C_1-C_8$-alkyl or $C_1-C_8$-alkoxy, each of which is optionally substituted by halogen, or $C_3-C_8$-cycloalkyl which is optionally substituted by halogen, $C_1-C_4$-alkyl or $C_1-C_4$-alkoxy and in which a methylene group is optionally replaced by oxygen or sulphur, or phenyl, phenyl-$C_1-C_4$-alkyl or phenyl-$C_1-C_4$-alkoxy, each of which is optionally substituted by halogen, $C_1-C_6$-alkyl, $C_1-C_6$-alkoxy, $C_1-C_4$-halogenoalkyl, $C_1-C_4$-halogenoalkoxy, nitro or cyano, $R^{14}$ represents hydrogen or $C_1-C_8$-alkyl, or $R^{13}$ and $R^{14}$ together represent $C_4-C_6$-alkanediyl, $R^{15}$ and $R^{16}$ are identical or different and represent $C_1-C_6$-alkyl, or $R^{15}$ and $R^{16}$ together represent a $C_2-C_4$-alkanediyl radical which is optionally substituted by $C_1-C_6$-alkyl, $C_1-C_6$-halogenoalkyl or by phenyl which is optionally substituted by halogen, $C_1-C_6$-alkyl, $C_1-C_4$-halogenoalkyl, $C_1-C_6$-alkoxy, $C_1-C_4$-halogenoalkoxy, nitro or cyano, $R^{17}$ and $R^{18}$ independently of one another represent hydrogen, or $C_1-C_8$-alkyl which is optionally substituted by halogen or phenyl which is optionally substituted by halogen, $C_1-C_6$-alkyl, $C_1-C_6$-alkoxy, $C_1-C_4$-halogenoalkyl, $C_1-C_4$-halogenoalkoxy, nitro or cyano, or $R^{17}$ and $R^{18}$, together with the carbon atom to which they are bonded, represent a carbonyl group, or $C_5-C_7$-cycloalkyl which is optionally substituted by $C_1-C_4$-alkyl or $C_1-C_4$-alkoxy and in which a methylene group is optionally replaced by oxygen or sulphur, $R^{19}$ and $R^{20}$ independently of one another represent $C_1-C_{10}$-alkyl, $C_2-C_{10}$-alkenyl, $C_1-C_{10}$-alkoxy, $C_1-C_{10}$-alkylamino, $C_3-C_{10}$-alkenylamino, di-($C_1-C_{10}$-alkyl)amino or di-($C_3-C_{10}$-alkenyl)amino.

3. Compounds of the formula (I) according to claim 1, in which

X represents $C_1-C_4$-alkyl,

Y represents fluorine, chlorine, bromine or $C_1-C_4$-alkyl,

Z represents fluorine, chlorine, bromine or $C_1-C_4$-alkyl, in this case one of the radicals Y and Z always represents halogen and the other alkyl, Het represents one of the groups

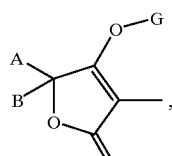

(2)

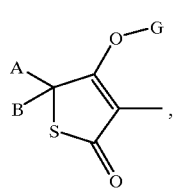, or (3)

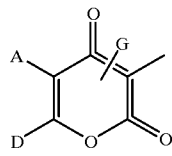, (5)

A represents hydrogen, or $C_1$–$C_{10}$-alkyl, $C_2$–$C_6$-alkenyl, $C_1$–$C_8$-alkoxy-$C_1$–$C_6$-alkyl, poly-$C_1$–$C_6$-alkoxy-$C_1$–$C_6$-alkyl or $C_1$–$C_8$-alkylthio-$C_1$–$C_6$-alkyl, each of which is optionally substituted by fluorine or chlorine, or $C_3$–$C_7$-cycloalkyl which is optionally substituted by fluorine, chlorine, $C_1$–$C_4$-alkyl or $C_1$–$C_4$-alkoxy and in which one or two methylene groups are optionally replaced by oxygen and/or sulphur, or phenyl, furanyl, pyridyl, imidazolyl, triazolyl, pyrazolyl, indolyl, thiazolyl, thienyl or phenyl-$C_1$–$C_4$-alkyl, each of which is optionally substituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano or nitro, B represents hydrogen, $C_1$–$C_{10}$-alkyl or $C_1$–$C_6$-alkoxy-$C_1$–$C_4$-alkyl or A, B and the carbon atom to which they are bonded represent $C_3$–$C_8$-cycloalkyl or $C_5$–$C_8$-cycloalkenyl, in which in each case a methylene group is optionally replaced by oxygen or sulphur and each of which is optionally substituted by $C_1$–$C_6$-alkyl, $C_3$–$C_8$-cycloalkyl, $C_1$–$C_3$-halogenoallyl, $C_1$–$C_6$-alkoxy, $C_1$–$C_6$-alkylthio, fluorine, chlorine or phenyl, or A, B and the carbon atom to which they are bonded represent $C_5$–$C_6$-cycloalkyl which is substituted by an alkylenediyl group optionally containing one or two oxygen or sulphur atoms or by an alkylenedioxyl group or by an alkylenedithioyl group and which, with the carbon atom to which it is bonded, forms a further 5- to 7-membered ring, or A, B and the carbon atom to which they are bonded represent $C_3$–$C_6$-cycloalkyl or $C_5$–$C_6$-cycloalkenyl, in which two substituents, together with the carbon atoms to which they are bonded, represent $C_3$–$C_5$-alkanediyl, $C_3$–$C_5$-alkenediyl or butadienediyl, each of which is optionally substituted by $C_1$–$C_5$-alkyl, $C_1$–$C_5$-alkoxy, fluorine, chlorine or bromine, and in which in each case a methylene group is optionally replaced by oxygen or sulphur, D represents hydrogen, or $C_1$–$C_{10}$-alkyl, $C_3$–$C_6$-alkenyl, $C_3$–$C_6$-alkinyl, $C_1$–$C_8$-alkoxy-$C_2$–$C_6$-alkyl, poly-$C_1$–$C_6$-alkoxy-$C_2$–$C_6$-alkyl or $C_1$–$C_8$-alkylthio-$C_2$–$C_6$-alkyl, each of which is optionally substituted by fluorine or chlorine, or $C_3$–$C_7$-cycloalkyl which is optionally substituted by fluorine, chlorine, $C_1$–$C_4$-alkyl, $C_1$–$C_4$-alkoxy or $C_1$–$C_2$-halogenoalkyl and in which one or two nondirectly adjacent methylene groups are optionally replaced by oxygen and/or sulphur, or phenyl, furanyl, imidazolyl, pyridyl, thiazolyl, pyrazolyl, pyrimidyl, pyrrolyl, thienyl, triazolyl or phenyl-$C_1$–$C_4$-alkyl, each of which is optionally substituted by fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, cyano or nitro, or A and D together represent a $C_3$–$C_5$-alkanediyl or $C_3$–$C_5$-alkenediyl group, in which in each case a carbon atom is optionally replaced by oxygen or sulphur and each of which is optionally substituted by fluorine, chlorine, hydroxyl, mercapto or by $C_1$–$C_6$-alkyl, $C_1$–$C_4$-alkoxy, $C_1$–$C_4$-alkylthio, $C_3$–$C_6$-cycloalkyl, phenyl or benzoyloxy, each of which is optionally substituted by fluorine or chlorine, or which in each case optionally contains one of the following groups:

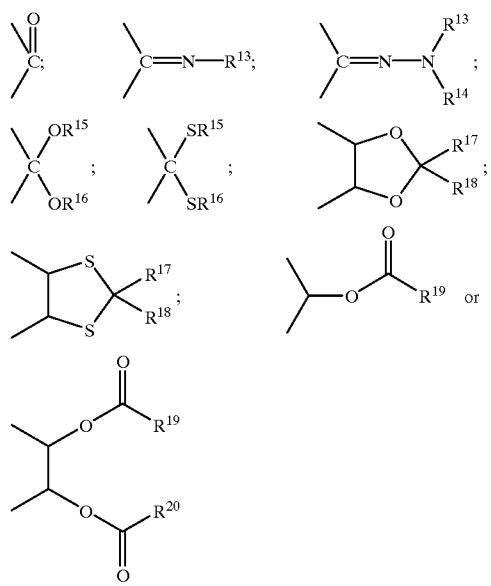

or A and D represent (in the case of the compounds of the formula (I-1)), together with the atoms to which they are bonded, one of the groups AD-1 to AD-27

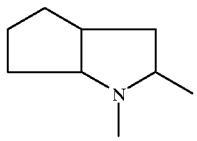

AD-1

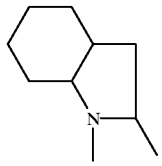

AD-2

-continued
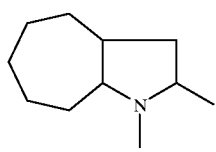
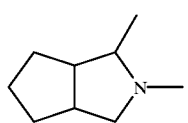
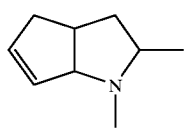
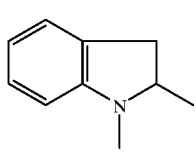
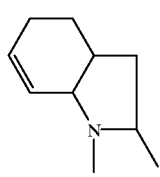
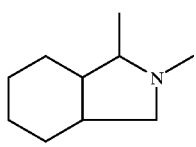
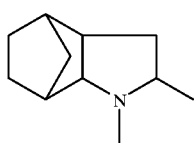
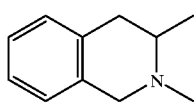
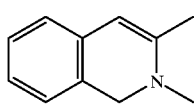
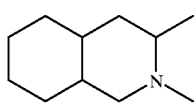
-continued
AD-3 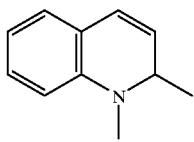
AD-4 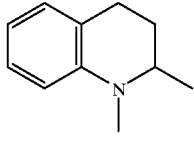
AD-5 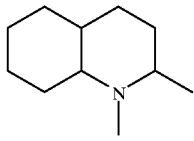
AD-6 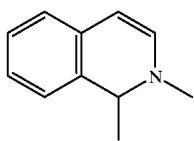
AD-7 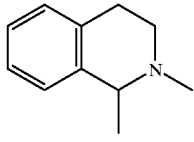
AD-8 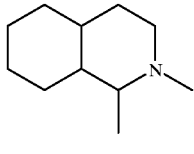
AD-9 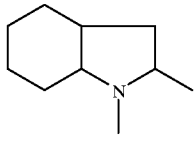
AD-10 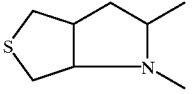
AD-11 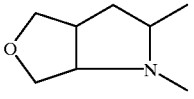
AD-12 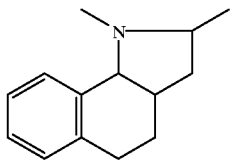
AD-13
AD-14
AD-15
AD-16
AD-17
AD-18
AD-19
AD-20
AD-21
AD-22

-continued

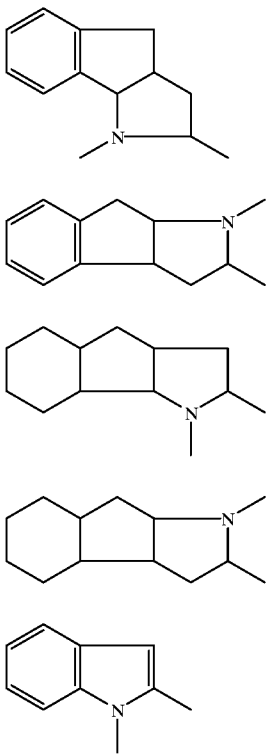

AD-23

AD-24

AD-25

AD-26

AD-27

G represents, in the case in which Het represents one of the radicals (2), (3), or (5) hydrogen (a) or, in the case in which Het represents one of the radicals (2), (3), or (5), one of the groups (b)
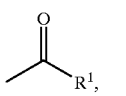

(c)
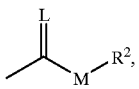

(d)
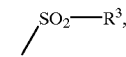

(e)

E or (f)

(g)
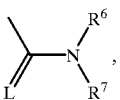

in which
E represents a metal ion equivalent or an ammonium ion,
L represents oxygen or sulphur and
M represents oxygen or sulphur, $R^1$ represents $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl, each of which is optionally substituted by fluorine or chlorine, or $C_3$–$C_7$-cycloalkyl which is optionally substituted by fluorine, chlorine, $C_1$–$C_5$-alkyl or $C_1$–$C_5$-alkoxy and in which one or two methylene groups are optionally replaced by oxygen and/or sulphur, phenyl which is optionally substituted by fluorine, chlorine, bromine, cyano, nitro, $C_1$–$C_4$-alkyl, $C_1$–$C_4$-alkoxy, $C_1$–$C_3$-halogenoalkyl, $C_1$–$C_3$-halogenoalkoxy, $C_1$–$C_4$-alkylthio or $C_1$–$C_4$-alkylsulphonyl, phenyl-$C_1$–$C_4$-alkyl which is optionally substituted by fluorine, chlorine, bromine, $C_1$–$C_4$-alkyl, $C_1$–$C_4$-alkoxy, $C_1$–$C_3$-halogenoalkyl or $C_1$–$C_3$-halogenoalkoxy, pyrazolyl, thiazolyl, pyridyl, pyrimidyl, furanyl or thienyl, each of which is optionally substituted by fluorine, chlorine, bromine or $C_1$–$C_4$-alkyl, phenoxy-$C_1$–$C_5$-alkyl which is optionally substituted by fluorine, chlorine, bromine or $C_1$–$C_4$-alkyl, or pyridyloxy-$C_1$–$C_5$-alkyl, pyrimidyloxy-$C_1$–$C_5$-alkyl or thiazolyloxy-$C_1$–$C_5$-alkyl, each of which is optionally substituted by fluorine, chlorine bromine, amino or $C_1$–$C_4$-alkyl, $R^2$ represents $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, each of which is optionally substituted by fluorine or chlorine, $C_3$–$C_7$-cycloalkyl which is optionally substituted by fluorine, chlorine, $C_1$–$C_4$-alkyl or $C_1$–$C_4$-alkoxy, or phenyl or benzyl, each of which is optionally substituted by fluorine, chlorine, bromine, cyano, nitro, $C_1$–$C_4$-alkyl, $C_1$–$C_3$-alkoxy, $C_1$–$C_3$-halogenoalkyl or $C_1$–$C_3$-halogenoalkoxy, $R^3$ represents $C_1$–$C_6$-alkyl which is optionally substituted by fluorine or chlorine, or phenyl or benzyl, each of which is optionally substituted by fluorine, chlorine, bromine, $C_1$–$C_5$-alkyl, $C_1$–$C_5$-alkoxy, $C_1$–$C_3$-halogenoalkyl, $C_1$–$C_3$-halogenoalkoxy, cyano or nitro, $R^4$ and $R^5$ independently of one another represent $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio or $C_3$–$C_4$-alkenylthio, each of which is optionally substituted by fluorine or chlorine, or phenyl, phenoxy or phenylthio, each of which is optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl, $R^6$ and $R^7$ independently of one another represent hydrogen, or $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, each of which is optionally substituted by fluorine or chlorine, or phenyl or benzyl, each of which is optionally substituted by fluorine, chlorine, bromine, $C_1$–$C_5$-halogenoalkyl, $C_1$–$C_5$-alkyl or $C_1$–$C_5$-alkoxy, or together represent a $C_3$–$C_6$-alkylene radical which is optionally substituted by $C_1$–$C_4$-alkyl and in which a methylene group is optionally replaced by oxygen or sulphur, $R^{13}$ represents hydrogen or $C_1$–$C_6$-alkyl or $C_1$–$C_6$-alkoxy, each of which is optionally substituted by fluorine or chlorine, or $C_3$–$C_7$-cycloalkyl which is optionally substituted by fluorine, $C_1$–$C_2$-alkyl or $C_1$–$C_2$-alkoxy and in which a methylene group is optionally replaced by oxygen or sulphur, or phenyl, phenyl-$C_1$–$C_3$-alkyl or phenyl-$C_1$–$C_2$-alkyloxy, each of which is optionally substituted by fluorine, chlorine, bromine, $C_1$–$C_5$-alkyl, $C_1$–$C_5$-alkoxy, $C_1$–$C_2$-halogenoalkyl, $C_1$–$C_2$-halogenoalkoxy, nitro or cyano, $R^{14}$ represents hydrogen or $C_1$–$C_6$-alkyl, or $R^{13}$ and $R^{14}$ together represent $C_4$–$C_6$-alkanediyl, $R^{15}$ and $R^{16}$ are identical or different and represent $C_1$–$C_4$-alkyl, or $R^{15}$ and $R^{16}$ together represent a $C_2$–$C_3$-alkanediyl radical which is optionally substituted by $C_1$–$C_4$-alkyl, $C_1$–$C_4$-halogenoalkyl or by phenyl which is optionally substituted by fluorine, chlorine, bromine, $C_1$–$C_4$-alkyl, $C_1$–$C_2$-halogenoalkyl, $C_1$–$C_4$-alkoxy, $C_1$–$C_2$-halogenoalkoxy, nitro or cyano, $R^{17}$ and $R^{18}$ independently of one another represent hydrogen, or $C_1$–$C_8$-alkyl which is optionally substituted by fluorine or chlorine, or phenyl which is optionally substituted by fluorine, chlorine, $C_1$–$C_4$-alkyl, $C_1$–$C_4$-alkoxy, $C_1$–$C_2$-halogenoalkyl, $C_1$–$C_2$-halogenoalkoxy, nitro or cyano, or $R^{17}$ and $R^{18}$ together with the carbon atom to which they are bonded, represent $C_5$–$C_6$-cycloalkyl which is optionally substituted by $C_1$–$C_3$-alkyl or
$C_1$–$C_3$-alkoxy and in which a methylene group is optionally replaced by oxygen or sulphur, $R^{19}$ and $R^{20}$ independently of one another represent $C_1$–$C_6$-alkyl, $C_2$–$C_6$-alkenyl, $C_1$–$C_6$-alkoxy, $C_1$–$C_6$-alkylamino, $C_3$–$C_6$-alkenylamino, di-($C_1$–$C_6$-alkyl)amino or di-($C_3$–$C_6$-alkenyl)amino.

4. Compounds of the formula (I) according to claim 1, in which

X represents methyl, ethyl, n-propyl or iso-propyl,

Y represents fluorine, chlorine, bromine, methyl, ethyl, n-propyl or iso-propyl, Z represents fluorine, chlorine, bromine, methyl, ethyl, n-propyl or iso-propyl, in this case one of the radicals Y and Z always represents halogen and the other alkyl, Het represents one of the groups

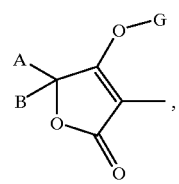
(2)

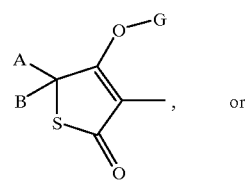
, or
(3)

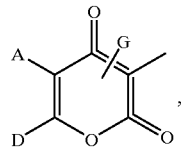
,
(5)

A represents hydrogen, or $C_1$–$C_8$-alkyl, $C_2$–$C_4$-alkenyl, $C_1$–$C_6$-alkoxy-$C_1$–$C_4$-alkyl, poly-$C_1$–$C_4$-alkoxy-$C_1$–$C_4$-alkyl or $C_1$–$C_6$-alkylthio-$C_1$–$C_4$-alkyl, each of which is optionally substituted by fluorine or chlorine, or $C_3$–$C_6$-cycloalkyl which is optionally substituted by fluorine, chlorine, methyl or methoxy and in which one or two methylene groups are optionally replaced by oxygen and/or sulphur, or phenyl, furanyl, thienyl, pyridyl or benzyl, each of which is optionally substituted by fluorine, chlorine, bromine, methyl, ethyl, n-propyl, iso-propyl, methoxy, ethoxy, trifluoromethyl, trifluoromethoxy, cyano or nitro, B represents hydrogen, $C_1$–$C_8$-alkyl or $C_1$–$C_4$-alkoxy-$C_1$–$C_2$-alkyl or A, B and the carbon atom to which they are bonded represent $C_3$–$C_8$-cycloalkyl or $C_5$–$C_8$-cycloalkenyl, in which in each case a methylene group is optionally replaced by oxygen or sulphur and each of which is optionally substituted by methyl, ethyl, n-propyl, iso-propyl, butyl, iso-butyl, sec-butyl, tert-butyl, cyclohexyl, trifluoromethyl, methoxy, ethoxy, n-propoxy, iso-propoxy, butoxy, iso-butoxy, sec-butoxy, tert-butoxy, methylthio, ethylthio, fluorine, chlorine or phenyl, or A, B and the carbon atom to which they are bonded very particularly preferably represent $C_5$–$C_6$-cycloalkyl which is substituted by an alkylenediyl group optionally containing an oxygen or sulphur atom or by an alkylenedioxyl group which, with the carbon atom to which it is bonded, forms a further five- or six-membered ring, or A, B and the carbon atom to which they are bonded represent $C_3$–$C_6$-cycloalkyl or $C_5$–$C_6$-cycloalkenyl, in which two substituents, together with the carbon atoms to which they are bonded, represent $C_3$–$C_4$-alkanediyl, $C_3$–$C_4$-alkenediyl or butadienediyl, in which in each case a methylene group is optionally replaced by oxygen or sulphur, D represents hydrogen, or $C_1$–$C_8$-alkyl, $C_3$–$C_4$-alkenyl, $C_3$–$C_4$-alkinyl, $C_1$–$C_6$-alkoxy-$C_2$–$C_4$-alkyl, poly-$C_1$–$C_4$-alkoxy-$C_2$–$C_4$-alkyl, $C_1$–$C_4$-alkylthio-$C_2$–$C_4$-alkyl or $C_3$–$C_6$-cycloalkyl, each of which is optionally substituted by fluorine or chlorine, and in which one or two non-directly adjacent methylene groups are optionally replaced by oxygen and/or sulphur, or phenyl, furanyl, pyridyl, thienyl or benzyl, each of which is optionally substituted by fluorine, chlorine, bromine, methyl, ethyl, n-propyl, iso-propyl, methoxy, ethoxy, trifluoromethyl, trifluoromethoxy, cyano or nitro, or A and D together represent a $C_3$–$C_5$-alkanediyl or $C_3$–$C_5$-alkenediyl group, in which in each case a methylene group is optionally replaced by oxygen or sulphur and each of which is optionally substituted by fluorine, chlorine, hydroxyl, mercapto or by $C_1$–$C_6$-alkyl, $C_1$–$C_4$-alkoxy, $C_1$–$C_4$-alkylthio, $C_3$–$C_6$-cycloalkyl, phenyl or benzyloxy, each of which is optionally substituted by fluorine or chlorine, or
which optionally contains one of the following groups

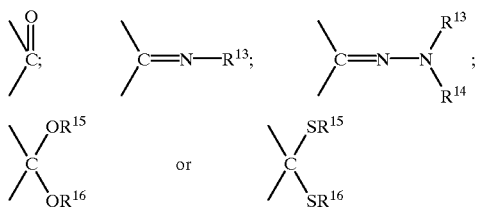

or A and D represent, in the case of the compounds of the formula (I-1), together with the atoms to which they are bonded, one of the following groups:

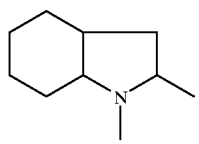
AD-1

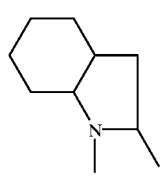
AD-2

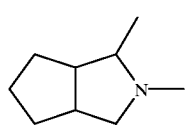
AD-4

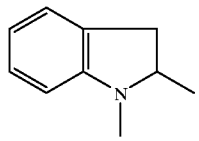
AD-6

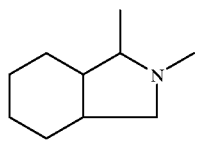
AD-8

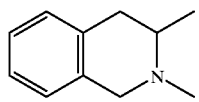
AD-10

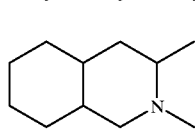
AD-12

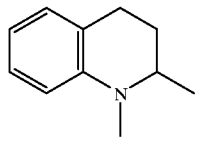
AD-14

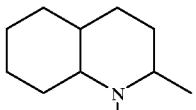
AD-15

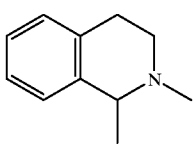
AD-17

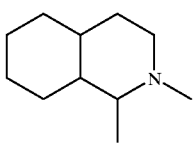
AD-18

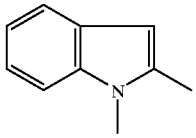
AD-27

G represents, in the case in which Het represents one of the radicals (2), (3), or (5) hydrogen (a) or, in the case in which Het represents one of the radicals (2), (3), or (5), one of the

(b)

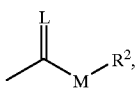
(c)

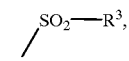
(d)

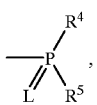
(e)

E   or
(f)

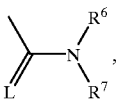
(g)

in which
    E represents a metal ion equivalent or an ammonium ion,
    L represents oxygen or sulphur and
    M represents oxygen or sulphur,
    $R^1$ represents $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, poly-$C_1$–$C_4$-alkoxy-$C_1$–$C_4$-alkyl, each of which is optionally substituted by fluorine or chlorine, or $C_3$–$C_6$-cycloalkyl which is optionally substituted by fluorine, chlorine, methyl, ethyl, n-propyl, i-propyl, n-butyl, i-butyl, tert-butyl, methoxy, ethoxy, n-propoxy or iso-propoxy and in which one or two methylene groups are optionally replaced by oxygen and/or sulphur, phenyl which is optionally substituted by fluorine, chlorine, bromine, cyano, nitro, methyl, ethyl, n-propyl, i-propyl, methoxy, ethoxy, trifluoromethyl, trifluoromethoxy, methylthio, ethylthio, methylsulphonyl or ethylsulphonyl, benzyl which is optionally substituted by fluorine, chlorine, bromine, methyl, ethyl, n-propyl, i-propyl, methoxy, ethoxy, trifluoromethyl or trifluoromethoxy, furanyl, thienyl or pyridyl, each of which is optionally substituted by fluorine, chlorine, bromine, methyl or ethyl, phenoxy-$C_1$–$C_4$-alkyl which is optionally substituted by fluorine, chlorine, methyl or ethyl, or pyridyloxy-$C_1$–$C_4$-alkyl, pyrimidyloxy-$C_1$–$C_4$-alkyl or thiazolyloxy-$C_1$–$C_4$-alkyl, each of which is optionally substituted by fluorine, chlorine, amino, methyl or ethyl, $R^2$ represents $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, each of which is optionally substituted by fluorine or chlorine, $C_3$–$C_6$-cycloalkyl which is optionally substituted by fluorine, chlorine, methyl, ethyl, n-propyl, iso-propyl or methoxy, or phenyl or benzyl, each of which is optionally substituted by fluorine, chlorine, cyano, nitro, methyl, ethyl, n-propyl, i-propyl, methoxy, ethoxy, trifluoromethyl or trifluoromethoxy, $R^3$ represents methyl, ethyl, propyl, isopropyl, each of which is optionally substituted by fluorine or chlorine, or phenyl or benzyl, each of which is optionally substituted by fluorine, chlorine, bromine, methyl, ethyl, propyl, iso-propyl, tert-butyl, methoxy, ethoxy, isopropoxy, tert-butoxy, trifluoromethyl, trifluoromethoxy, cyano or nitro, $R^4$ and $R^5$ independently of one another represent $C_1$–$C_4$-alkyl, $C_1$–$C_4$-alkoxy, $C_1$–$C_4$-alkylamino, di-($C_1$–$C_4$-akyl)amino or $C_1$–$C_4$-alkylthio, each of which is optionally substituted by fluorine or chlorine, or phenyl, phenoxy or phenylthio, each of which is optionally substituted by fluorine, chlorine, bromine, nitro, cyano, methyl, methoxy, trifluoromethyl or trifluoromethoxy, $R^6$ and $R^7$ independently of one another represent hydrogen, or $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, each of which is optionally substituted by fluorine or chlorine, or phenyl or benzyl, each of which is optionally substituted by fluorine, chlorine, bromine, methyl, methoxy or trifluoromethyl, or together represent a $C_5$–$C_6$-alkylene radical which is optionally substituted by methyl or ethyl and in which a methylene group is optionally replaced by oxygen or sulphur, $R^{13}$ represents hydrogen or $C_1$–$C_4$-alkyl or $C_1$–$C_4$-alkoxy, each of which is optionally substituted by fluorine or chlorine, $C_3$–$C_6$-cycloalkyl, or phenyl, phenyl-$C_1$–$C_2$-alkyl or benzyloxy, each of which is optionally substituted by fluorine, chlorine, bromine, methyl, ethyl, iso-propyl, tert-butyl, methoxy, ethoxy, iso-propoxy, tert-butoxy, trifluoromethyl, trifluoromethoxy, nitro or cyano, $R^{14}$ represents hydrogen or $C_1$–$C_4$-alkyl, or $R^{13}$ and $R^{14}$ together represent $C_4$–$C_6$-alkanediyl, $R^{15}$ and $R^{16}$ are identical or different and represent methyl or ethyl, or $R^{15}$ and $R^{16}$ together represent a $C_2$–$C_3$-alkanediyl radical which is optionally substituted by methyl, ethyl; n-propyl, iso-propyl, n-butyl, iso-butyl, sec-butyl, tert-butyl or by phenyl which is optionally substituted by fluorine, chlorine, methoxy, trifluorometeyl, trifluoromethoxy, nitro or cyano.

5. Process for the preparation of compounds of the formula (I) according to claim 1, characterized in that (A) compounds of the formula (I-1-a)

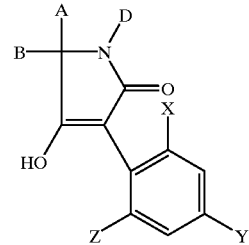

(I-1-a)

in which

A, B, D, X, Y and Z have the meanings given in claim 1, are obtained when compounds of the formula (II)

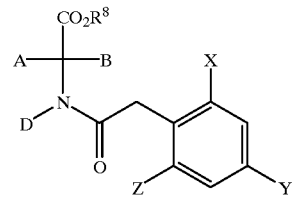

(II)

in which

A, B, D, X, Y and Z have the meanings given above, and $R^8$ represents alkyl, are intramolecularly condensed in the presence of a diluent and in the presence of a base, (B) compounds of the formula (I-2-a)

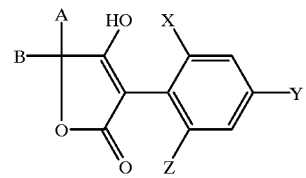

(I-2-a)

in which

A, B, X, Y and Z have the meanings given above, are obtained when compounds of the formula (III)

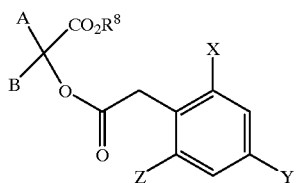
(III)

in which
A, B, X, Y, Z and $R^8$ have the meanings given above,
are intramolecularly condensed in the presence of a diluent and in the presence of a base, (C) compounds of the formula (I-3-a)

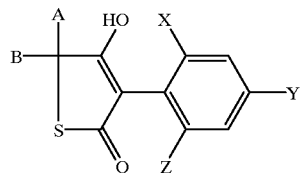
(I-3-a)

in which
A, B, X, Y and Z have the meanings given above,
are obtained when
compounds of the formula (IV)

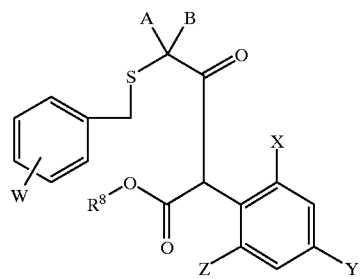
(IV)

in which
A, B, X, Y, Z and $R^8$ have the meanings given above and
W represents hydrogen, halogen, alkyl or alkoxy,
are cyclized, if appropriate in the presence of a diluent and in the presence of an acid, (E) the compounds of the formula (I-5-a)

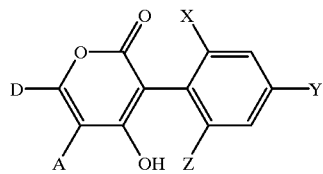
(I-5-a)

in which
A, D, X, Y and Z have the meanings given above,
are obtained when compounds of the formula (VIII)

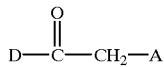
(VIII)

in which
A and D have the meanings given above,
are reacted with compounds of the formula (V)

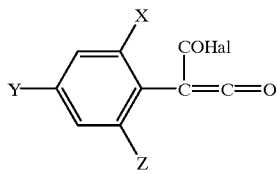
(V)

in which
X, Y and Z have the meanings given above and
Hal represents halogen,
if appropriate in the presence of a diluent and if appropriate in the presence of an acid acceptor, (F) the compounds of the formula (I-6-a)

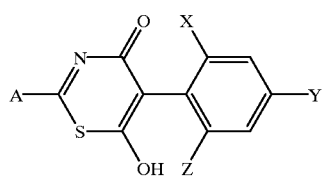
(I-6-a)

in which
A, X, Y and Z have the meanings given above,
are obtained when compounds of the formula (IX)

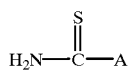
(IX)

in which
A has the meaning given above,
are reacted with compounds of the formula (V)

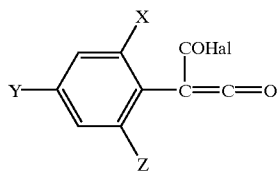
(V)

in which
Hal, X, Y and Z have the meanings given above,
if appropriate in the presence of a diluent and if appropriate in the presence of an acid acceptor, and optionally then the compounds thus obtained of the formulae (I-1-a) to (I-3-a), (I-5-a) and (I-6-a) shown above, compounds of the formula (I4-a)

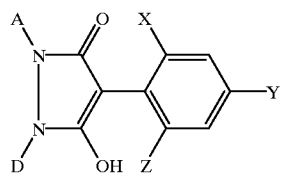
(I-4-a)

in which
A, D, X, Y and Z have the meanings given above, in each case are reacted (G)α) with acid halides of the formula (X)

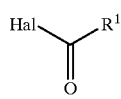
(X)

in which
R$^1$ has the meaning given above and
Hal represents halogen, or

β) with carboxylic anhydrides of the formula (XI)

R$^1$—CO—O—CO—R$^1$ (XI)

in which
R$^1$ has the meaning given above,
if appropriate in the presence of a diluent and if appropriate in the presence of an acid-binding agent, (H) with chloroformic acid esters or chloroformic acid thioesters of the formula (XII)

R$^2$—M—CO—Cl (XII)

in which
R$^2$ and M have the meanings given above,
if appropriate in the presence of a diluent and if appropriate in the presence of an acid-binding agent, or (I)α) with chloromonothioformic acid esters or chlorodithioformic acid esters of the formula (XIII)

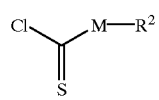
(XIII)

in which
M and R$^2$ have the meanings given above,
if appropriate in the presence of a diluent and if appropriate in the presence of an acid-binding agent or β) with carbon disulphide and then with compounds of the formula (XIV)

R$^2$—Hal (XIV)

in which
R$^2$ has the meaning given above and
Hal represents chlorine, bromine or iodine,
if appropriate in the presence of a diluent and if appropriate in the presence of a base, (J) with sulphonyl chlorides of the formula (XV)

R$^3$—SO$_2$—Cl (XV)

in which
R$^3$ has the meaning given above,
if appropriate in the presence of a diluent and if appropriate in the presence of an acid-binding agent, or (K) with phosphorus compounds of the formula (XVI)

(XVI)

in which
L, R$^4$ and R$^5$ have the meanings given above and
Hal represents halogen,
if appropriate in the presence of a diluent and if appropriate in the presence of an acid-binding agent, or (L) with metal compounds or amines of the formula (XVII) or (XVIII)

Me(OR$^{10}$)$_t$ (XVII)

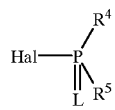
(XVIII)

in which
Me represents a mono- or divalent metal,
t represents the number 1 or 2 and
R$^{10}$, R$^{11}$, R$^{12}$ independently of one another represent hydrogen or alkyl,
if appropriate in the presence of a diluent, or (M)α) with isocyanates or isothiocyanates of the formula (XIX)

R$^6$—N=C=L (XIX)

in which
R$^6$ and L have the meanings given above,
if appropriate in the presence of a diluent and if appropriate in the presence of a catalyst, or β) with carbamoyl chlorides or thiocarbamoyl chlorides of the formula (XX)

(XX)

in which
L, R$^6$ and R$^7$ have the meanings given above,
if appropriate in the presence of a diluent and if appropriate in the presence of an acid-binding agent.

6. A pesticidal composition comprising a pesticidally effective amount of a compound according to claim 1 and an extender.

7. A method of combating unwanted pests which comprises administering to such pests or to a locus from which it is desired to exclude such pests a pesticidally effective amount of a compound according to claim 1.

8. A herbicidal composition comprising a herbicidally effective amount of a compound according to claim 1 and an extender.

9. A method of combating unwanted vegetation which comprises administering to such vegetation or to a locus from which it is desired to exclude such vegetation a herbicidally effective amount of a compound according to claim 1.

* * * * *

UNITED STATES PATENT AND TRADEMARK OFFICE
CERTIFICATE OF CORRECTION

PATENT NO. : 6,251,830 B1
DATED : June 26, 2001
INVENTOR(S) : Reiner Fischer et al.

It is certified that error appears in the above-identified patent and that said Letters Patent is hereby corrected as shown below:

Column 132,
Line 32, after "...one of the..." insert -- groups --

Signed and Sealed this

Seventh Day of October, 2003

JAMES E. ROGAN
*Director of the United States Patent and Trademark Office*